(12) United States Patent  (10) Patent No.: US 8,070,290 B2
Gille et al.  (45) Date of Patent: Dec. 6, 2011

(54) GONIOSCOPE FOR IMPROVED VIEWING

(75) Inventors: Henrick K. Gille, Oceanside, CA (US);
Leslie Dale Foo, Tucson, AZ (US);
James Patrick McGuire, Jr., Pasadena, CA (US)

(73) Assignee: Glaukos Corporation, Laguna Hills, CA (US)

( * ) Notice: Subject to any disclaimer, the term of this patent is extended or adjusted under 35 U.S.C. 154(b) by 0 days.

(21) Appl. No.: 12/639,928

(22) Filed: Dec. 16, 2009

(65) Prior Publication Data

US 2010/0265461 A1    Oct. 21, 2010

Related U.S. Application Data

(60) Provisional application No. 61/243,115, filed on Sep. 16, 2009, provisional application No. 61/185,144, filed on Jun. 8, 2009, provisional application No. 61/274,108, filed on Dec. 17, 2008.

(51) Int. Cl.
*A61B 3/00* (2006.01)
*G02C 7/02* (2006.01)
*G02C 7/04* (2006.01)

(52) U.S. Cl. ............ 351/219; 351/174; 351/160 R
(58) Field of Classification Search .......... 351/200–246, 351/174, 160 R
See application file for complete search history.

(56) References Cited

U.S. PATENT DOCUMENTS

| D166,597 S | 4/1952 | Filsinger |
| 3,112,570 A | 12/1963 | De Vasconcellos |
| 3,589,800 A | 6/1971 | Cardona |
| 3,753,611 A | 8/1973 | Ebbesen |
| 3,820,879 A | 6/1974 | Frisen |
| 4,033,679 A * | 7/1977 | Sussman ............... 351/221 |
| 4,067,646 A | 1/1978 | Nohda |
| 4,134,647 A | 1/1979 | Ramos-Caldera |
| 4,134,667 A | 1/1979 | Schnall et al. |
| 4,307,944 A | 12/1981 | Schirmer |
| 4,439,026 A | 3/1984 | Wilms |
| 4,469,413 A | 9/1984 | Shirayanagi |
| 4,568,157 A | 2/1986 | Kurwa |
| 4,598,984 A | 7/1986 | Rol |
| 4,627,694 A | 12/1986 | Volk |

(Continued)

FOREIGN PATENT DOCUMENTS

WO    WO 2009/158517    12/2009

OTHER PUBLICATIONS

Volk, "Aspheric Ophthalmic Lenses", Refraction, International Ophthalmology Clinics, vol. 5, No. 2, Jun. 1965.

(Continued)

*Primary Examiner* — Mohammed Hasan
(74) *Attorney, Agent, or Firm* — Knobbe, Martens, Olson & Bear, LLP

(57) ABSTRACT

Various embodiments relate to opthalmoscopic devices, systems and methods for viewing the anterior chamber, trabecular meshwork, iris root, scleral spur, and/or related nearby structures in the eye. In some embodiments, devices, systems and/or methods may employ a plurality of gonioscopic optical elements that form a virtual image that can be imaged by a microscope directly in front of a patient (e.g., without tilting the patient's head). Various embodiments described herein may be useful for ophthalmologic diagnoses, treatments, monitoring and/or surgical procedures. Some embodiments include a gonioscopic attachment configured to attach to a conventional gonioscope and redirect light emitted by the gonioscope. Various embodiments described herein can be incorporated into disposable, single-use gonioscopes.

52 Claims, 33 Drawing Sheets

U.S. PATENT DOCUMENTS

| | | | |
|---|---|---|---|
| 4,664,490 | A | 5/1987 | Rol |
| 4,682,866 | A | 7/1987 | Volk |
| 4,721,378 | A | 1/1988 | Volk |
| 4,728,183 | A | 3/1988 | Heacock et al. |
| 4,738,521 | A | 4/1988 | Volk |
| 4,799,784 | A | 1/1989 | Safir |
| 4,907,872 | A | 3/1990 | Schirmer et al. |
| 5,007,729 | A | 4/1991 | Erickson et al. |
| 5,024,518 | A | 6/1991 | Richards et al. |
| 5,046,836 | A | 9/1991 | Volk |
| 5,200,773 | A | 4/1993 | Volk |
| 5,216,456 | A | 6/1993 | Volk |
| 5,260,578 | A | 11/1993 | Bliton et al. |
| 5,309,187 | A | 5/1994 | Crossman et al. |
| 5,359,372 | A | 10/1994 | Kida et al. |
| 5,412,441 | A | 5/1995 | Tibbling et al. |
| 5,424,789 | A | 6/1995 | Volk |
| 5,479,222 | A | 12/1995 | Volk |
| 5,501,217 | A | 3/1996 | Ishiguro et al. |
| 5,535,060 | A | 7/1996 | Grinblat |
| 5,537,164 | A | 7/1996 | Smith |
| D394,704 | S | 5/1998 | Koepnick |
| 5,784,147 | A | 7/1998 | Volk |
| 5,805,269 | A | 9/1998 | Volk |
| 5,822,036 | A | 10/1998 | Massie et al. |
| 6,164,779 | A | 12/2000 | Volk |
| 6,183,085 | B1 | 2/2001 | Roggy et al. |
| 6,698,886 | B2 | 3/2004 | Pollack et al. |
| 6,767,098 | B2 | 7/2004 | Erickson et al. |
| 6,942,343 | B2 | 9/2005 | Farberov |
| 6,976,758 | B2 * | 12/2005 | Khaw et al. .................. 351/219 |
| D523,881 | S | 6/2006 | Edwards et al. |
| 7,125,119 | B2 | 10/2006 | Farberov |
| D534,194 | S | 12/2006 | Hines et al. |
| 7,144,111 | B1 | 12/2006 | Ross, III et al. |
| D549,326 | S | 8/2007 | Aparici et al. |
| 7,261,687 | B2 | 8/2007 | Yang ............................ 600/173 |
| 7,357,504 | B2 | 4/2008 | Fischer et al. |
| D574,867 | S | 8/2008 | Lewis |
| 7,419,262 | B2 * | 9/2008 | Whalen ........................ 351/174 |
| 7,766,480 | B1 | 8/2010 | Graham et al. |
| 2009/0137989 | A1 | 5/2009 | Kataoka |
| 2010/0118269 | A1 | 5/2010 | Shea et al. |
| 2010/0118270 | A1 | 5/2010 | Shea et al. |

OTHER PUBLICATIONS

Ocular Swan Autoclavable Gonioprism from at least as early as Jun. 29, 2007 in 3 pages, downloaded from http://ocularinc.com.

Ocular Hill Surgical Gonioprism from at least as early as Jun. 29, 2007 in 3 pages, downloaded from http://www.ocularinc.com.

Ocular Khaw Surgical Gonioprism from at least as early as Jun. 29, 2007 in 3 pages, downloaded from http://www.ocularinc.com.

International Search Report and Written Opinion for PCT Application No. PCT/US2009/068322, dated Mar. 11, 2010.

Haag-Streit Contact Glasses Brochure, retrieved Mar. 20, 2007.

Office Action for Design U.S. Appl. No. 29/352,588 dated Jan. 12, 2011.

Office Action for Design U.S. Appl. No. 29/352,589 dated Jan. 12, 2011.

"Beam Steering by Wedge Prisms," last updated Jun. 15, 2006, available at: http://micro.magnet.fsu. edu/primer/java/prismsandbeamsplitters/wedgeprisms/index.html.

* cited by examiner

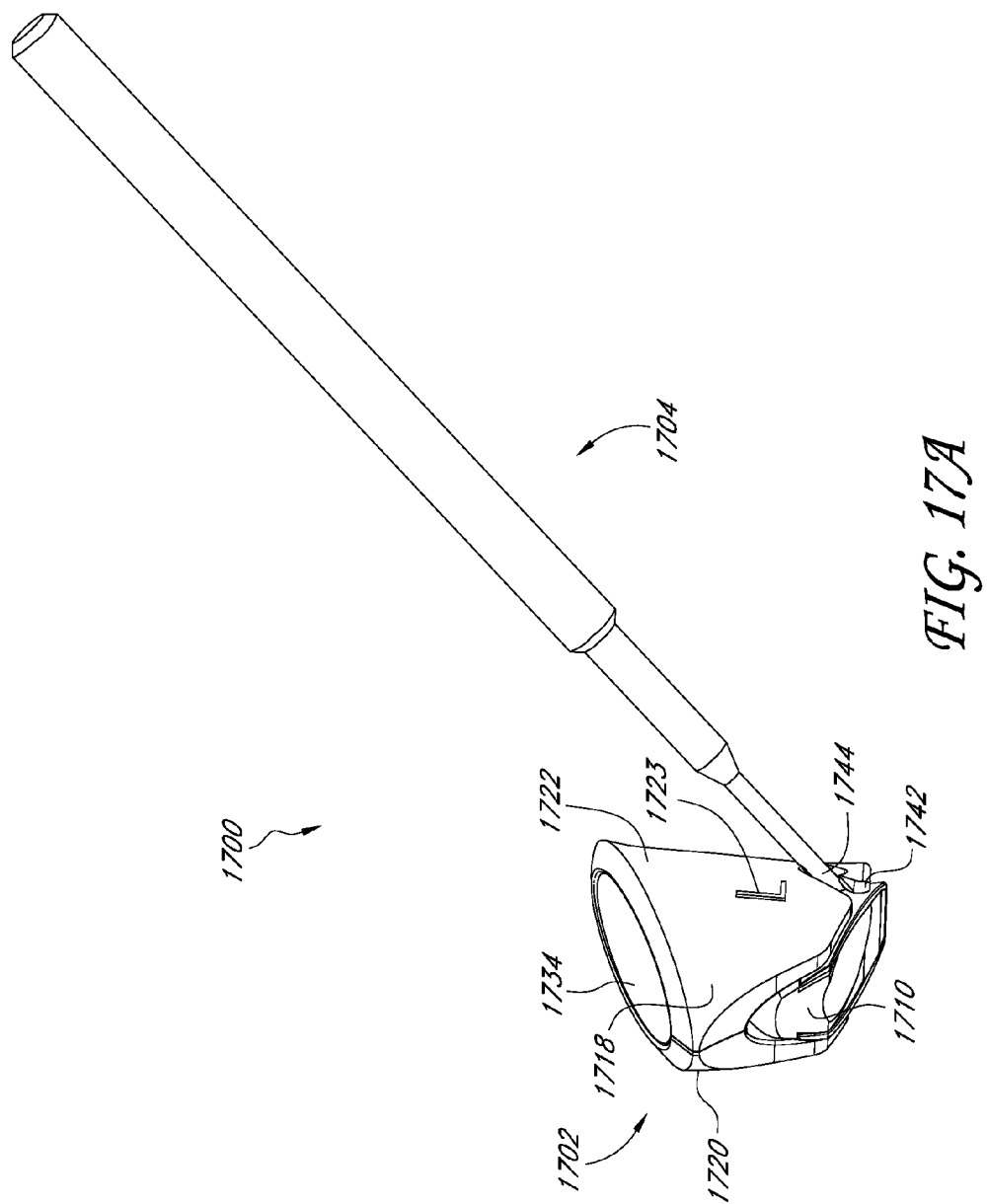

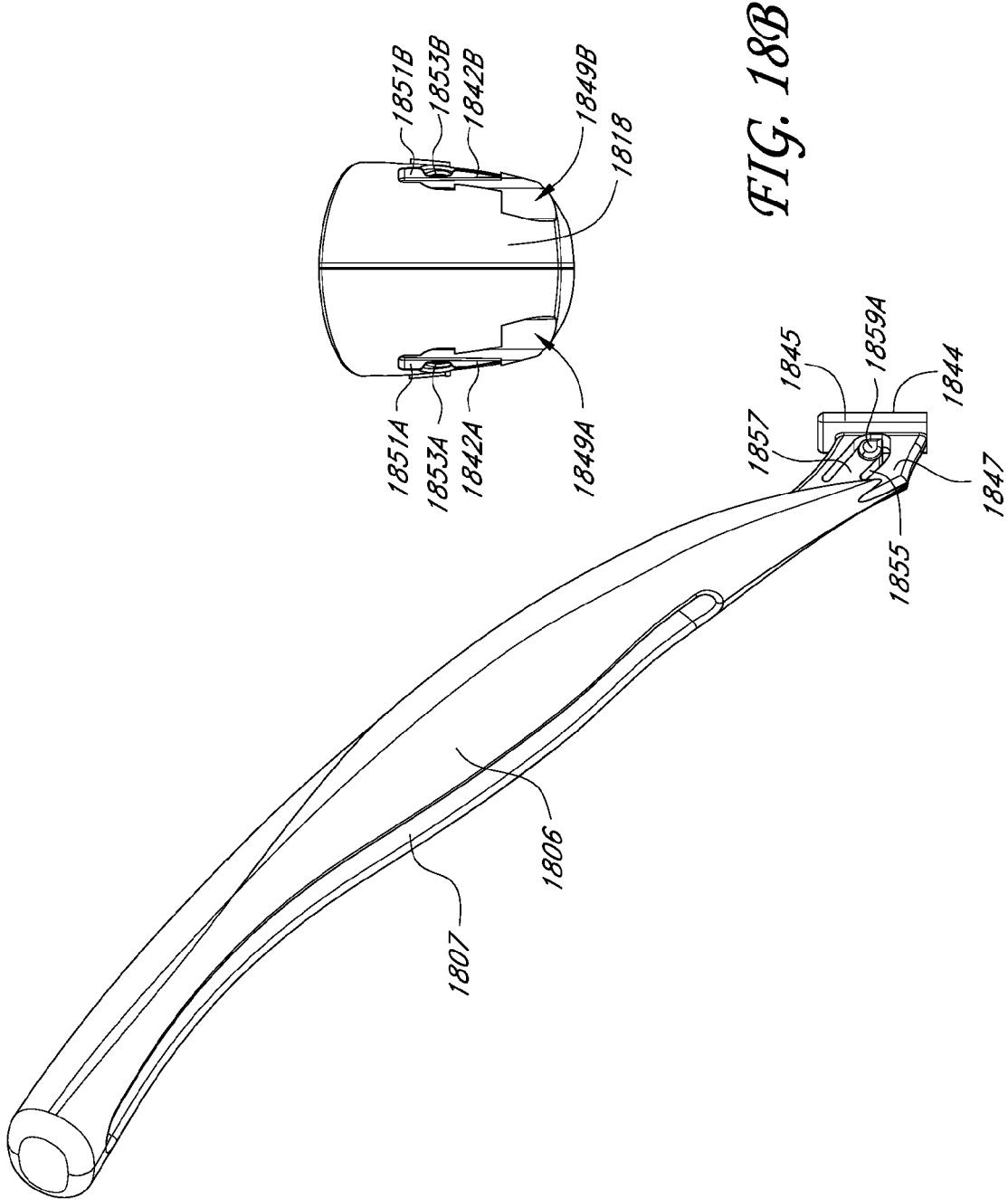

GONIOSCOPE FOR IMPROVED VIEWING

PRIORITY CLAIM

This application claims the priority benefit under 35 U.S.C. §119(e) of U.S. Provisional Patent Application No. 61/243,115, filed on Sep. 16, 2009; U.S. Provisional Patent Application No. 61/185,144, filed on Jun. 8, 2009; and U.S. Provisional Patent Application No. 61/274,108, filed on Dec. 17, 2008. Each of the above-identified patent applications is hereby incorporated by reference in its entirety.

BACKGROUND OF THE INVENTION

1. Field of the Invention

Various embodiments relate to opthalmoscopic devices, systems and methods useful for viewing structures including but not limited to the anterior chamber; trabecular meshwork, iris root, scleral spur, and/or related nearby anatomical structures in the eye. In some embodiments, devices, systems and/or methods may employ a plurality of gonioscopic optical elements that form a virtual image that can be imaged by a microscope directly in front of a patient. Various embodiments described herein may be useful for opthalmologic diagnoses, treatments, monitoring and/or surgical procedures.

2. Description of the Related Art

Gonioscopy is a technique used for viewing the inner parts of the eye, such as the retina and the anterior chamber angle of the eye for evaluation, management, and classification of normal and abnormal structures. Devices used for gonioscopy are known as gonioscopes. Observation of the anterior chamber and especially its angle areas, which are difficult or impossible to see with the use of simple microscopes, is commonly used for diagnosis of eye diseases. For example, the classification of glaucoma relies heavily upon knowledge of the anterior segment anatomy, particularly that of the anterior chamber angle. Additionally, some surgical procedures used to treat glaucoma involve placing a small tubular stent into the trabecular meshwork in the anterior chamber angle formed by the iris and the cornea. Proper placement of the stent may depend on visualization of the Trabeculum and the angle.

The anterior chamber of a human eye is commonly evaluated with an illuminated microscope (e.g., slit lamp sterero-microscopy), but the chamber angle is typically hidden from ordinary view because of total internal reflection of light rays emanating from the angle structures. A small optical device known to ophthalmologists as a gonioscope is used to enhance visibility of the Trabeculum and the angle. During surgical applications, it may be hand held by the surgeon in place over the patient's cornea while he/she is performing the surgical procedure.

SUMMARY OF THE INVENTION

Various embodiments disclosed herein include a gonioscopic attachment for redirecting light emitted by a gonioscope. The gonioscopic attachment can include a housing defining an interior chamber, and the housing can include a connector configured to allow the housing to be removably attached to a gonioscope. The gonioscopic attachment can also include an attachment optical element secured within the interior chamber, and the attachment optical element can be substantially wedge-shaped. The interior chamber can include a recess located below the attachment optical element, and the recess can be configured to receive at least a portion of a gonioscopic optical element of the gonioscope and position the gonioscopic optical element such that light emitted by the gonioscopic optical element is directed toward the attachment optical element.

The housing can be substantially tubular in shape. The connector can be configured to provide a snap-fit connection with an attachment region on a handle of the gonioscope. The attachment region can have a thickness, and the connector can include a cutout located at a base portion of said housing, with the cutout having a width wide enough to receive the attachment region of the gonioscope. The cutout can have a narrowed region having a narrowed width that is less than the thickness of the attachment region. The housing can include at least one right-handed connector configured to allow the housing to be removably attached to the gonioscope in a right-handed configuration and a left-handed connector configured to allow the housing to be removably attached to the gonioscope in a left-handed configuration.

The attachment optical element can include a transparent material, a distal surface to receive the light emitted by the gonioscopic optical element of the gonioscope, and a proximal surface to output the light transmitted through the transparent material. At least one of the distal surface and the proximal surface of the attachment optical element can be substantially planar. In some embodiments, both the distal surface and the proximal surface of the attachment optical element can be substantially planar.

The attachment optical element can be configured such that the light output by the proximal surface of the attachment optical element forms a virtual image viewable by a microscope. The attachment optical element can be configured such that the light output by the second surface of the attachment optical element forms an upright image viewable by a microscope.

The attachment optical element can be configured such that at least a portion of the light is transmitted through the transparent material without internal reflection and forms an image viewable by a microscope. The attachment optical element is configured such that at least a portion of the light is transmitted through the transparent material directly from the distal surface to the proximal surface without striking any other surfaces of the attachment optical element and forms an image viewable by a microscope.

In some embodiments, the housing can have a longitudinal axis, and the attachment optical element can be configured to receive the light emitted by the gonioscopic optical element and redirect the light such that the light output by the attachment optical element is directed with an average deviation of no more than 10° from parallel to the longitudinal axis. The attachment optical element can be configured to receive the light emitted by the gonioscopic optical element and redirect the light such that the light output by the attachment optical element is directed with an average deviation of no more than 5° from parallel to the longitudinal axis. The attachment optical element can be configured to receive the light emitted by the gonioscopic optical element and redirect the light such that the light output by the attachment optical element is directed with an average deviation of no more than 1° from parallel to the longitudinal axis.

The attachment optical element can be configured to redirect the light so as to form an image viewable by a microscope without the attachment optical element relying on reflections. The attachment optical element can be configured to redirect the light using refraction.

The recess can be configured to receive an upper portion of the gonioscopic optical element such that a lower portion of the gonioscopic optical element extends out below the housing. The recess can be configured to position the gonioscopic optical element such that an air gap is formed between the gonioscopic optical element and the attachment optical element.

The attachment optical element can include a transparent plastic material. The housing can include an opaque plastic material. The housing can have an interior surface, and at least a portion of the interior surface can be configured to reduce reflections. The interior surface can include a dark colored material.

Various embodiments disclosed herein include a gonioscopic assembly for intraocular observation. The gonioscopic assembly can include a first gonioscopic optical element that includes a transparent material and has a distal surface. The distal surface can be concave and can have a radius of curvature between about 5 mm and 11 mm. The gonioscopic assembly can also include a handle supporting the first gonioscopic optical element and a housing removably attached to the handle or the first gonioscopic optical element. The housing can define an interior chamber. The gonioscopic assembly can also include a second gonioscopic optical element positioned within the interior chamber.

The interior chamber can include a recess located below the second gonioscopic optical element, and the recess can be configured to receive at least a portion of the first gonioscopic optical element and position the first gonioscopic optical element such that light emitted by the first gonioscopic optical element is directed toward the second gonioscopic optical element. The first gonioscopic optical element can be substantially wedge-shaped having a narrow end closer to a first side of the housing and a wide end closer to a second side of the housing, and the second gonioscopic optical element can be substantially wedge-shaped having a narrow end closer to the first side of the housing and a wide end closer to the second side of the housing.

Various embodiments disclosed herein include a gonioscopic assembly for intraocular observation. The gonioscopic assembly can include a housing defining an interior chamber and an attachment optical element secured within the interior chamber. The interior chamber can include a recess located below the attachment optical element. The gonioscopic assembly can also include a gonioscope removably attached to the housing, and the gonioscope can include a gonioscopic optical element at least partially disposed in the recess. The gonioscopic optical element can have a concave distal surface with a radius of curvature between about 5 mm and 11 mm.

Various embodiments disclosed herein include a gonioscope for intraocular observation. The gonioscope can include a housing and a first gonioscopic optical element supported by the housing. The first gonioscopic optical element can include a transparent material and can have a distal surface that has a radius of curvature between about 5 mm and 11 mm. The gonioscope can also include a second gonioscopic optical element supported by the housing and positioned above the first gonioscopic optical element so that light emitted by the first gonioscopic optical element is directed toward the second gonioscopic optical element. The gonioscope can also include a handle configured to support the housing and be toggleable between a right-handed position and a left-handed position.

The housing can include a right-handed connection point and a left-handed connection point, and the handle can include an attachment region configured to removably mate with either of the right-handed connection point or the left-handed connection point. In some embodiments, the handle can be swivelably attached to the housing and can be secured in either the right-handed position or in the left-handed position. In some embodiments, the handle can be hingedly attached to the housing and can be secured in either the right-handed position or in the left-handed position.

In some embodiments, each of said first gonioscopic optical element, said second gonioscopic optical element, said housing, and said handle includes plastic material.

Various embodiments disclosed herein include a gonioscope for intraocular observation. The gonioscope can include a housing and a first gonioscopic optical element supported by the housing. The first gonioscopic optical element can include a transparent material and can have a concave distal surface with a radius of curvature between about 5 mm and 11 mm. The gonioscope can also include a second gonioscopic optical element supported by the housing and positioned above the first gonioscopic optical element so that light emitted by the first gonioscopic optical element is directed toward the second gonioscopic optical element, and a handle supporting the housing.

In some embodiments, each of the first gonioscopic optical element, the second gonioscopic optical element, the housing, and the handle includes plastic material.

Various embodiments include a gonioscope for intraocular observation of an eye. The gonioscope can include a first gonioscopic optical element that includes a transparent material, and has a distal surface to receive light from an object in the eye, and has a proximal surface to output the light transmitted through the transparent material. The distal surface can be concave and can have a radius of curvature sufficiently close to the radius of curvature of an average eye so as to fit over the eye. The object can be disposed laterally in a first direction with respect to the first gonioscopic optical element. The gonioscope can include a second gonioscopic optical element that includes a transparent material, and the second gonioscopic optical element can have a distal surface to receive the light output from the proximal surface of the first gonioscopic element and a proximal surface to output the light transmitted through the transparent material of the second gonioscopic element. The first gonioscopic optical element and the second gonioscopic optical element can be configured such that light output by the gonioscope forms an uninverted image of the object viewable by a microscope without the gonioscope reflecting more than 50% of the light. The uninverted image can be disposed laterally in a second direction with respect to the first gonioscopic optical element, and the second direction can be opposite the first direction. At least a portion of the distal surface of the second gonioscopic optical element used to form said image of the object can be spaced apart from the proximal surface of the first gonioscopic optical element, and an air gap can be located therebetween.

In some embodiments, at least a portion of the distal surface of the second gonioscopic optical element used to form said image of the object can be spaced apart from the proximal surface of the first gonioscopic optical element by at least 0.1 mm. In some embodiments, no additional optical elements are located between the first gonioscopic optical element and the second gonioscopic optical element.

The object can be in an object plane that is within a range of between about 0.5 millimeters and 10 millimeters from the distal surface of the first gonioscopic optical element. The image can be distal to the first gonioscopic optical element. The object can be in an object plane and said image can be tilted with respect to said object plane by no more than 10°. In some embodiments, the image can be tilted with respect to said object plane by no more than 5°. In some embodiments, the image can be tilted with respect to said object plane by no more than 1°. The gonioscope can provide magnification such that said image is magnified with respect to said object.

The distal surface of the first gonioscopic optical element can have a radius of curvature between about 5 mm and 11 mm. In some embodiments, at least one of said first gonioscopic optical element and second gonioscopic optical elements can have a tapered thickness with an average thickness on a first side that is thicker than the average thickness on a second side. In some embodiments, both the first gonioscopic optical element and second gonioscopic optical elements have tapered thicknesses, each with an average thickness on a first side that is thicker than the average thickness on a second side. In some embodiments, at least one of said proximal surface or said distal surface of said second gonioscopic optical element is substantially planar.

The gonioscope can also include a recess in a perimeter of the distal surface of first gonioscopic optical element. The recess can be at least about 1.5 mm deep. The recess can be at least about 10 mm wide.

The transparent material of at least one of the first and second gonioscopic optical elements can include acrylic. The transparent material of at least one of the first and second gonioscopic optical elements can include glass.

The gonioscope can also include a housing having openings for input and output of the light from said object in said eye and a handle attached to said housing. The housing can have a longitudinal axis, and the first and second gonioscopic optical elements can be disposed along said longitudinal axis such that light from said object in said eye exiting said proximal surface of said second gonioscopic optical element is directed with an average deviation therefrom of no more than 10° from parallel to said longitudinal axis. The first and second gonioscopic optical elements can be disposed along said longitudinal axis such that said virtual image is less degraded when viewed from an angle of less than 10° with respect to said longitudinal axis than when viewed at an angle greater than 10° with respect to said longitudinal axis.

Various embodiments include a gonioscope for intraocular observation of an eye. The gonioscope can include a first gonioscopic optical element that includes transparent material, and has a distal surface to receive light from an anterior chamber of the eye, and has a proximal surface to output the light transmitted through the transparent material. The distal surface can be concave and can have a radius of curvature sufficiently close to the radius of curvature of an average eye so as to fit over the eye. The anterior chamber can be disposed laterally in a first direction with respect to the first gonioscopic optical element. The gonioscope can also include a second gonioscopic optical element that includes transparent material and has a first index of refraction. The second gonioscopic optical element can have a distal surface to receive the light output from the proximal surface of the first gonioscopic element and a proximal surface to output the light transmitted through the transparent material of the second gonioscopic element. The first gonioscopic optical element and the second gonioscopic optical element can be configured such that light output by the gonioscope forms a virtual image of the anterior chamber viewable by a microscope without said gonioscope reflecting more than 50% of the light. The virtual image can be disposed laterally in a second direction with respect to said first gonioscopic optical element, and the second direction can be opposite the first direction. In some embodiments, at least a portion of the distal surface of the second gonioscopic optical element used to form said image of the anterior chamber can be spaced apart from the proximal surface of the first gonioscopic optical element defining a space therebetween. The space can include a medium having a second index of refraction that is lower than the first index of refraction. The medium can be air.

Various embodiments include a gonioscope for intraocular observation of an eye. The gonioscope can include a first gonioscopic optical element that includes transparent material, and has a distal surface to receive light from an anterior chamber of the eye, and has a proximal surface to output the light transmitted through the transparent material. The distal surface can be concave and can have a radius of curvature sufficiently close to the radius of curvature of an average eye so as to fit over the eye. The eye can define an optical axis, and said anterior chamber can be disposed laterally in a first direction with respect to the optical axis of said eye. The gonioscope can also include a second gonioscopic optical element that includes transparent material having a first index of refraction. The second gonioscopic optical element can have a distal surface to receive the light output from the proximal surface of the first gonioscopic element and a proximal surface to output the light transmitted through the transparent material of the second gonioscopic element. The optical axis can intersect the proximal surface of the second gonioscopic optical element at a location where the proximal surface of the gonioscopic optical element is non-perpendicular to the optical axis. The first gonioscopic optical element and the second gonioscopic optical element can be configured such that light output by the gonioscope forms an image of the anterior chamber viewable by a microscope without said gonioscope reflecting more than 50% of the light. The image can be disposed laterally in a second direction with respect to the optical axis of the eye, and said second direction can be opposite said first direction. In some embodiments, at least a portion of the distal surface of the second gonioscopic optical element used to form said image of the anterior chamber can be spaced apart from the proximal surface of the first gonioscopic optical element defining a space therebetween. The space can include a medium having a second index of refraction that is lower than the first index of refraction.

Various embodiments include a gonioscope for intraocular observation of an eye. The gonioscope can include a first gonioscopic optical element that includes transparent material, and has a distal surface to receive light from an object, and has a proximal surface to output the light transmitted through the transparent material. The distal surface can be concave and can have a radius of curvature sufficiently close to the radius of curvature of an average eye so as to fit over the eye. The object can be disposed laterally in a first direction with respect to the first gonioscopic optical element. The gonioscope can also include a second gonioscopic optical element that includes transparent material having a first index of refraction. The second gonioscopic optical element can have a distal surface to receive the light output from the proximal surface of the first gonioscopic element and a proximal surface to output the light transmitted through the transparent material of the second gonioscopic element. The second gonioscopic optical element can be substantially-wedge shaped. The first gonioscopic optical element and the second gonioscopic optical element can be configured such that light output by the gonioscope forms an image of the object viewable by a microscope without said gonioscope reflecting more than 50% of the light. The image can be disposed laterally in a second direction with respect to the first gonioscopic optical element, and the second direction can be opposite said first direction. In some embodiments, at least a portion of the distal surface of the second gonioscopic optical element used to form said image of the object can be spaced apart from the proximal surface of the first gonioscopic optical element defining a space therebetween. The space can include a material having a second index of refraction that is lower than the first index of refraction.

Various embodiments include a gonioscope for intraocular observation. The gonioscope can include a first gonioscopic optical element that includes transparent material, and has a distal surface to receive light from an anterior chamber of the eye, and has a proximal surface to output the light transmitted through the transparent material. The distal surface can be concave and can have a radius of curvature sufficiently close to the radius of curvature of an average eye so as to fit over the eye. The anterior chamber can be disposed laterally in a first direction with respect to the first gonioscopic optical element. The gonioscope can also include a second gonioscopic optical element that includes transparent material having a first index of refraction. The second gonioscopic optical element can have a distal surface to receive the light output from the proximal surface of the first gonioscopic element and a proximal surface to output the light transmitted through the transparent material of the second gonioscopic element. The first gonioscopic optical element and the second gonioscopic optical element can be rotationally asymmetric and can be configured such that light output by the gonioscope forms an image of the anterior chamber without reflecting more than 50% of the light. The image can be viewable by a microscope. The image can be disposed laterally in a second direction with respect to said first gonioscopic optical element, and said second direction ca be opposite said first direction. In some embodiments, at least a portion of the distal surface of the second gonioscopic optical element used to form said image of the anterior chamber can be spaced apart from the proximal surface of the first gonioscopic optical element defining a space therebetween. The space can include a medium having a second index of refraction that is lower than the first index of refraction.

Various embodiments include a gonioscope for intraocular observation. The gonioscope can include a first gonioscopic optical element that includes transparent material, and has a distal surface to receive light from an object at an object plane, and has a proximal surface to output the light transmitted through the transparent material. The distal surface can be concave and can have a radius of curvature between about 5 mm and 11 mm. The gonioscope can also include a second gonioscopic optical element that includes transparent material. The second gonioscopic optical element can have a distal surface to receive the light output from the proximal surface of the first gonioscopic element and a proximal surface to output the light transmitted through the transparent material of the second gonioscopic element. The second gonioscopic optical element can be substantially wedge-shaped. The first gonioscopic optical element and the second gonioscopic optical element can be configured such that light output by the gonioscope forms an image of the object viewable by a microscope without said gonioscope reflecting more than 50% of the light. In some embodiments, at least a portion of the distal surface of the second gonioscopic optical element used to form said image of the object can be spaced apart from the proximal surface of the first gonioscopic optical element, and an air gap can be located therebetween.

Various embodiments include a gonioscope for intraocular observation. The gonioscope can include a first gonioscopic optical element that includes transparent material, and has a distal surface to receive light from an object, and has a proximal surface to output the light transmitted through the transparent material. The distal surface can be concave and can have a radius of curvature between about 5 mm and 11 mm. The first gonioscopic optical element can be substantially wedge-shaped having a thick end and a narrow end, and the thick end can be disposed closer to the object than the narrow end. The gonioscope can also include a second gonioscopic optical element that includes transparent material. The second gonioscopic optical element can have a distal surface to receive the light output from the proximal surface of the first gonioscopic element and a proximal surface to output the light transmitted through the transparent material of the second gonioscopic element. The second gonioscopic optical element can be substantially wedge-shaped having a thick end and a narrow end, can the thick end being can be disposed closer to the object than the narrow end. The gonioscope can also include an air gap located between the first gonioscopic optical element and the second gonioscopic optical element. The first gonioscopic optical element and the second gonioscopic optical element can be configured such that light output by the gonioscope forms an image of the object viewable by a microscope.

The thick end of the second gonioscopic optical element can be disposed substantially above the thick end of the first gonioscopic optical element, and the narrow end of the second gonioscopic optical element can be disposed substantially above the narrow end of the first gonioscopic optical element.

BRIEF DESCRIPTION OF THE DRAWINGS

The foregoing and other features, aspects and advantages of the present invention are described in detail below with reference to the drawings of various embodiments, which are intended to illustrate and not to limit the invention. The drawings comprise the following figures in which:

FIGS. 17A-17E schematically show various components of a gonioscopic optical system comprising a gonioscopic attachment configured to attach to a gonioscope.

FIGS. 18A-18F schematically show various components of a gonioscopic optical system comprising two gonioscopic optical elements secured by a housing and an ergonomic handle.

DETAILED DESCRIPTION OF THE PREFERRED EMBODIMENT

Embodiments of the invention will now be described with reference to the accompanying figures, wherein like numerals refer to like elements throughout. The terminology used in the description presented herein is not intended to be interpreted in any limited or restrictive manner, simply because it is being utilized in conjunction with a detailed description of certain specific embodiments of the invention. Furthermore, embodiments of the invention may comprise several novel features, no single one of which is solely responsible for its desirable attributes or which is essential to practicing the inventions herein described.

Figure 1:
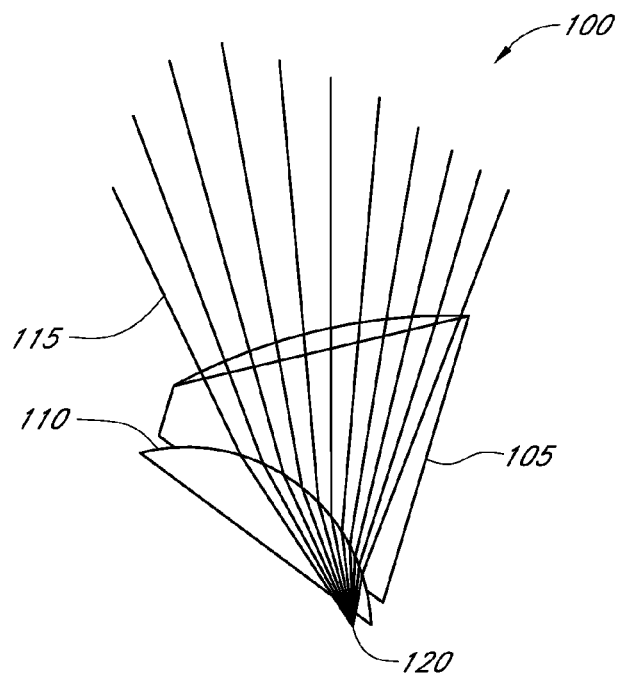
FIG. 1 schematically illustrates an example of a Hill Gonioprism.

A number of disadvantages are associated with various gonioscopic designs. Use of some gonioscopes involves positioning a subject's head and/or a microscope to a particular angle. For example, FIG. 1 shows an example of a Hill Gonioprism 105 positioned on a subject's eye 110. During surgery, the subject's head is typically tilted about 30 degrees so that light 115 forming an image of the anterior chamber 120 is visible by using a microscope. Such positioning can be inconvenient and can limit the equipment and/or procedures that can be used while the subject is in this position. Surgical procedures, for example, are drastically different when a subject is positioned as described as compared to other ophthalmic surgeries, such as cataract surgery, where a patient may be supine without the patient's head tilted at 30°. Therefore, if the subject requires a stent for glaucoma treatment at the time of cataract surgery, the subject may need to be repositioned between the procedures, which can be inconvenient and inefficient.

In some embodiments, systems and methods are provided to image an ocular structure (e.g., an anterior chamber, an anterior chamber angle and/or a Trabeculum) of a subject. The systems may comprise two or more gonioscopic optical elements (e.g., wedge shaped prisms, toroidal or spherical lens, etc.) configured to refract light reflected by the subject's ocular structure. Light is collected that is initially reflected by the structure at an angle with respect to the optical axis of the subject's eye. However, each of the gonioscopic optical elements may refract the light more parallel to the eye's optical axis. Accordingly, tilting the head by 30° may not be needed.

Additionally, the gonioscopic optical elements may be configured to reduce light dispersion and chromatic aberration. The system may be configured to provide a short, direct optical path between a source and the structure, thereby improving an image of the region. Additionally, the system may be configured such that there are not multiple images of the structure formed, that there is no image inversion, that there is little or reduced anamorphic distortion and/or that correct color is provided across a visible spectrum.

Figure 2:
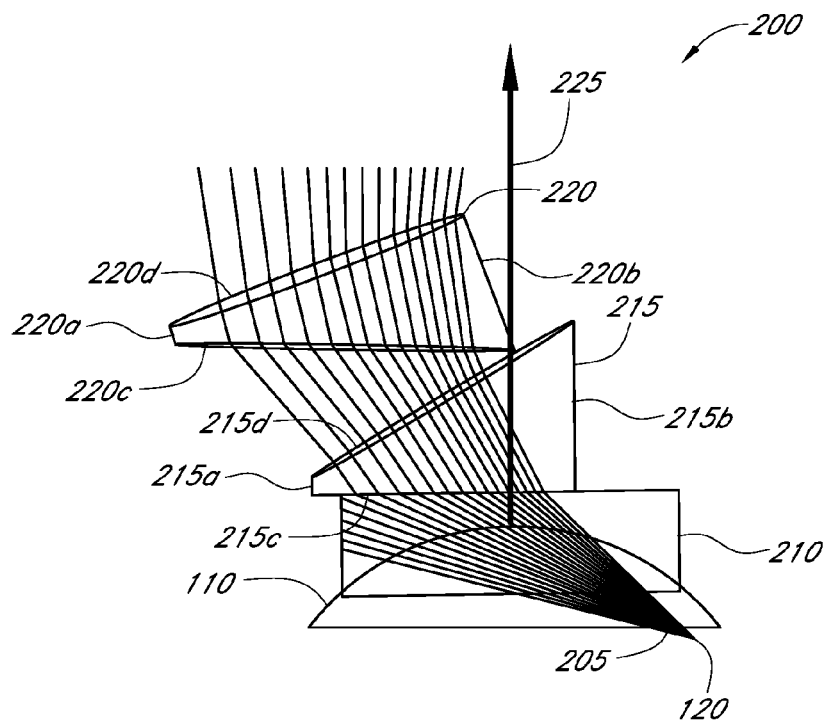
FIGS. 2 and 3 schematically illustrate gonioscopic optical systems comprising three gonioscopic optical elements, two of which are wedge-shaped.

FIG. 2 shows an example of a gonioscopic optical system 200 configured to direct light 205 reflected from a subject's anterior chamber 120 or nearby structure. The light 205 may exit the subject's eye 110 (e.g., via the cornea) and be received by a first gonioscopic optical element 210. In some instances, such as those in which light is reflected at the anterior chamber or nearby structure 120, light 205 enters the first gonioscopic optical element 210 at a non-zero input angle $\theta_{1,i}$ compared to an optical axis 225 of the subject's eye and exits the first gonioscopic optical element 210 at an output angle $\theta_{1,o}$ compared to the optical axis. In some embodiments, the first gonioscopic optical element 210 does not substantially refract the light 205 ($\theta_{1,i}=\theta_{1,o}$), while in other embodiments, it does ($\theta_{1,i}\neq\theta_{1,o}$). The input and output angles for the first gonioscopic optical element 210 may differ, for example, by less than about 30, 20, 10, 5, 4, 3, 2, 1, or 0.5 degrees.

The first gonioscopic optical element 210 may comprise or consist of, for example, a lens or a prism. In some instances, the first gonioscopic optical element 210 includes a curved or concave distal surface. (The surface is referred to as distal because of its orientation with respect to the user who may peer through the gonioscope system at the eye, the distal surface being closer to the subject eye, and farther from the user. Alternatively, the surface may be referred to as posterior.) The distal surface may comprise a shape substantially corresponding to, for example, the shape of a cornea, for example, the shape of an average cornea. In some embodiments, for example, the curved distal surface may have a radius of curvature between about 5 mm and 11 mm although curvatures outside these ranges are also possible. In some embodiments, the first gonioscopic optical element 210 includes a substantially flat or flat proximal lens surface. (The surface is referred to as proximal because of its orientation with respect to the user who may peer through the gonioscope system at the eye, the proximal surface being closer to the user's eye, and farther from the subject's eye, in comparison to the distal surface. Alternatively, the surface may be referred to as anterior.) The proximal surface may be configured to receive light from the distal surface that is transmitted through the first gonioscopic optical element, i.e., through transparent material between the proximal and distal surface of the first gonioscopic optical element. Accordingly, the first gonioscopic optical element 210 may comprise a plano-concave lens.

In some embodiments, the first gonioscopic optical element 210 comprises a recess, relief, or undercut. The first gonioscopic optical element 210 may be manufactured to include the recess, relief, or undercut, or the recess, relief, or undercut may subsequently be made (e.g., by a user) in the element. The recess, relief, or undercut may, for example, increase the accessibility and introduction of tools to the cornea, the limbus, or the adjacent scleral or conjunctive tissue. The length of the recess, relief, or undercut may vary depending on, for example, the tools to be used in a procedure, but in some instances is greater than about 1 mm, 3 mm, 6 mm, or 9 mm and may be less than about 2 mm, 5 mm, or 10 mm in various embodiments. Similarly, the depth of the recess, relief, or undercut into the distal surface may vary depending on, for example, the tools to be used in a procedure, but in some instances is greater than about 1 mm, 3 mm, or 5 mm and may be less than about 2 mm, 4 mm, or 6 mm in various embodiments.

By applying a light coating of fluid matching a refractive index of an ocular structure (e.g., the cornea) to the bottom of the first gonioscopic optical element 210, optical effects of the cornea may be reduced or eliminated. The fluid may comprise, for example, a gel such as a viscoelastic gel.

The first gonioscopic optical element 210 may direct light towards a second gonioscopic optical element 215. The second gonioscopic optical element 215 may be disposed with respect to the first gonioscopic optical element 210 for capturing and refracting the light rays (e.g., reflected by the anterior chamber or nearby structure and) transmitted by the first gonioscopic optical element 210. In some instances, the second gonioscopic optical element 215 is positioned on the first gonioscopic optical element 210.

In some instances, light 205 enters the second gonioscopic optical element 215 at a non-zero input angle $\theta_{2,i}$ compared to the optical axis 225 and exits the second gonioscopic optical element 215 at an output angle $\theta_{2,o}$ compared to the optical axis 225. The second gonioscopic optical element 215 may refract the light 205, such that the second gonioscopic optical element output angle is smaller than the corresponding input angle ($\theta_{2,o} < \theta_{2,i}$). The difference between the second gonioscopic optical element input angle $\theta_{2,i}$ and output angle $\theta_{2,o}$ may be, for example, at least about or less than about 1, 2, 3, 5, 10, 15, 20, 25, 30, 35, 40, 45, 50 or 60 degrees. The second gonioscopic optical element 215 may refract input light at an input (e.g., distal) surface interface 215c. The input surface interface 215c may comprise, for example, an interface between the second gonioscopic optical element 215 and air.

A third gonioscopic optical element 220 may be optically aligned with the second gonioscopic optical element 215 for capturing and refracting the light rays transmitted through the second gonioscopic optical element 215. In some instances, light 205 enters the third gonioscopic optical element 220 at a non-zero input angle $\theta_{3,i}$ compared to a normal vector 225 and exits the third gonioscopic optical element 220 at an output angle $\theta_{3,o}$ compared to the normal vector 225. The third gonioscopic optical element 220 may refract the light 205, such that the third gonioscopic optical element output angle is smaller than the corresponding input angle ($\theta_{3,o} < \theta_{3,i}$). The difference between the third gonioscopic optical element input angle $\theta_{3,i}$ and output angle $\theta_{3,o}$ may be, for example, at least about or less than about 1, 2, 3, 5, 10, 15, 20, 25, 30, 35, 40, 45, 50 or 60 degrees. In some instances, the average angle of all light 205 output from the third gonioscopic optical element or the average of all the light reflected at the anterior chamber or nearby structure 120 that is output by the gonioscope is less than about 20, 15, 10, 8, 6, 5, 4, 3, 2, 1 or 0.5 degrees with respect to the optical axis. Thus, the light output from the third gonioscopic optical element 220 or gonioscope may be in a direction substantially parallel to an optical axis of a surgical microscope. The third gonioscopic optical element 220 may refract input light at an input (e.g., distal) interface 220c. The input surface interface 220c may comprise, for example, an interface between the third gonioscopic optical element 220 and air.

In some embodiments, the object imaged by the gonioscopic optical image, e.g., the Trabeculum is located medially or nasally with respect to the first gonioscopic optical element 210 or the optical axis 225. In various embodiments, the second and/or third gonioscopic optical element and/or the light collected by the second and/or third gonioscopic optical element is on average located laterally or temporally with respect to the first gonioscopic optical element or the optical axis 225. Additionally, the second and third gonioscopic optical elements shown in FIG. 2 have tapered thickness, the thickness being reduced in the lateral or temporal direction. Although some embodiments disclosed herein discuss the gonioscope positioned to image an object in the nasal side of the eye, they can also be used to image an object on the temporal side of the eye. Thus in some embodiments, the second and/or third gonioscopic optical element can be located laterally or medially or nasally to the first gonioscopic optical element, and the second and third gonioscopic optical elements can have a reduced thickness in the medial or nasal direction.

Figure 3:
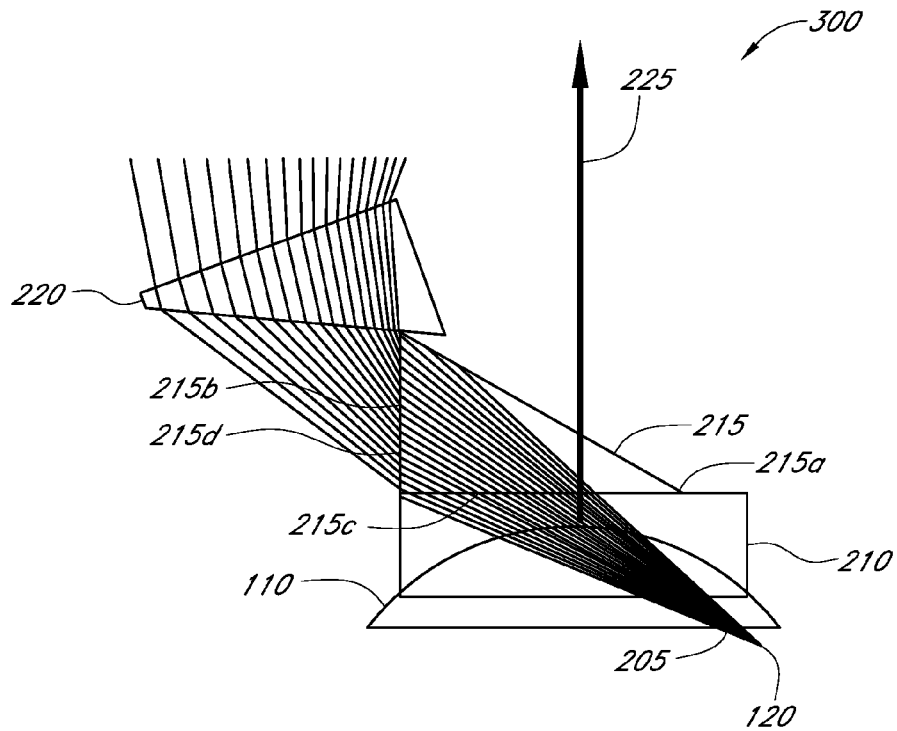

FIG. 3 shows a system 300, in which one of the optical elements—in this instance the second gonioscopic optical element 215 has a tapered thickness, the thickness being reduced in the medial or nasal direction. This second gonioscopic optical element refracts light at an output surface interface 215d.

Figure 4:
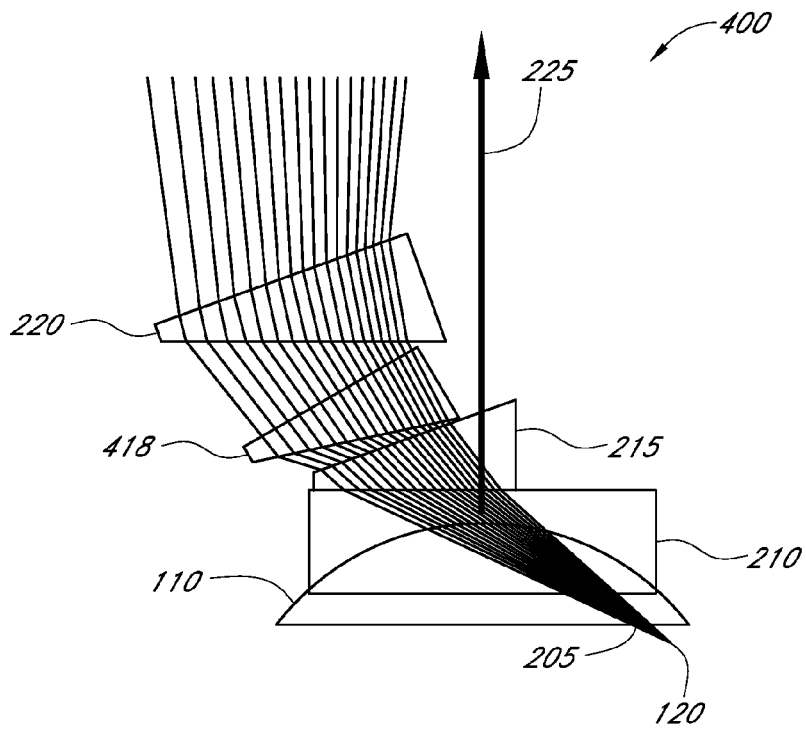
FIG. 4 schematically illustrates a gonioscopic optical system comprising four gonioscopic optical elements, three of which are wedge-shaped.

As shown in FIG. 4, in some instances, more gonioscopic optical elements are provided. In FIG. 4, a gonioscopic optical system 400 comprises four gonioscopic optical elements 210, 215, 220 and 418. Additional gonioscopic optical elements (e.g., third gonioscopic optical element 418) may have any properties or characteristics as described with respect to the second and fourth gonioscopic optical elements 215 and 220. For example, the third gonioscopic optical element 418 may be configured to refract input light such that an output angle is smaller than an input angle.

In some instances, the number of gonioscopic optical elements is less than 10, 5, 4, or 3. Additional gonioscopic optical elements may lead to increased cost, increased manufacturing complexity, more chromatic aberration and/or increased difficulty in transmitting large cones of light from a source to a subject's eye. However, because ray deviation is shared across elements, the additional elements may decrease anamorphic distortion. In certain embodiments, the additional elements may, however, increase anamorphic distortion. Furthermore, chromatic aberration may be offset by additional elements having different (e.g., opposing) dispersion characteristics.

In some embodiments, the number, shape and positions of one or more elements of a system disclosed herein may be configured such that the system comprises a short, direct optical path. This path may increase the field of view or improve the visibility of a field of view and/or remove confusing multiple reflections. For example, the system may be designed such that the virtual image is formed by using no reflective elements and likewise no reflections (e.g., of greater than 50%, 60%, 70%, 80%, 90%, 95% reflectivity) may occur within the gonioscopic optical system. Additionally, the elements may be configured such that there is no image inversion. For example, zero reflections of greater than 50%, 60%, 70%, 80%, 90%, 95% reflectivity may occur within the system. The elements may be configured to reduce anamorphic distortion and/or to provide substantially correct color across a visible spectrum (e.g., 0.4-0.7 microns). Additionally, the elements may be configured such that lateral and/or longitudinal image shift (the distance from the object to the virtual image) is less than about 15, 10, 8, 6, 5, 4, 3, 2 or 1 mm.

Gonioscopic optical elements may be separated by a medium. The medium may have a refractive index $n_3$, the medium's refractive index being different than (e.g., less than) the refractive indices of the gonioscopic optical elements being separated. In some instances, the refractive indices of the gonioscopic optical elements being separated are substantially equal. The medium may comprise air, and thus, the medium's refractive index may be about 1.

As described above, the thickness of one or more gonioscopic optical elements may vary along a dimension. In some instances, the dimension is that characterized as a medial-lateral dimension when the gonioscopic system is in use. The thickness may monotonically change along the dimension. As shown in an embodiment of FIG. 2, a gonioscopic optical element (e.g., 215 or 220) may have a small-thickness side 215a and 220a and a large-thickness side 215b and 220b opposite to the small-thickness side. The large-thickness side 215b or 220b may be closer to the optical axis 225 of a subject's eye than is the small-thickness side 215a or 220a. In other embodiments, such as the embodiment shown in FIG. 3, a small-thickness side 215a is closer to the optical axis 225 than is the large-thickness side 215b. Accordingly, in some instances, a gonioscopic optical element comprises at least part of a wedge or comprises a wedge. In some embodiments, one or more of the gonioscopic optical elements can be rotationally asymmetric (such as, for example, a wedge). In conditions in which the element comprises a wedge, such as that shown in FIG. 3, the small-thickness side 215a refers to the point opposite the large-thickness side 215b. The wedge may comprise a toroidal or spherical wedge. A gonioscopic optical element may comprise a toroidal or spherical surface, which may reduce, minimize or eliminate chromatic, astigmatic, and/or anamorphic aberrations.

A gonioscopic optical element may comprise a prism. An apex angle of the prism at the intersection of the two surfaces through which light enters and exits a prism may be configured based on desired beam deviation. In various embodiments, the amount of beam deviation is proportional to the prism apex angle. In some instances, the prism is immersed in a refractive media. Immersing the prism in refractive media, however, may increase apex angle. Increasing apex angle can result in total internal reflection at the exit surface of the prism. The prism may comprise an achromatic prism comprising refractive materials with different dispersive properties. The achromatic prism may be associated with smaller lateral chromatic errors than is a chromatic prism, larger overall volume than is a chromatic prism, larger astigmatism than is a chromatic prism, and/or total internal reflection at an output face (thereby limiting maximum deviation).

Optical complications may arise from configurations comprising planar surfaced prisms, as they may be associated with aberrations that may adversely affect image quality. Prisms may introduce residual chromatic aberrations and/or introduce anamorphic distortion, which may cause the image to shorten in one axis. To reduce these aberrations, independent radii of curvature may be added to proximal (anterior) surfaces (e.g., surfaces 215d or 220d in FIG. 2) of a gonioscopic optical element. The radii may be different in different directions thereby producing a toroidal optical surface and an anamorphic optical element. The independent radii of curvature may reduce or minimize astigmatism. Optical ray trace simulations, such as those using Code V® available from Optical Research Associates Pasadena, Calif., optics engineering software, may be used to determine the specification of the prescription for gonioscopes.

In some embodiments, a gonioscopic optical element comprises a center that is offset from, does not intersect and/or does not nearly intersect the optical axis 225. The center may comprise, for example, a center of a proximal surface or a center of a distal surface. The center may comprise a center of mass or may be based on the area of the optical surfaces (e.g., may be an average location of the centroids of the distal or proximal surfaces). In some embodiments, at least one of the gonioscopic optical elements is configured, shaped, aligned and/or positioned such that most, all, substantially all, or an average of the light 205 reflected at the anterior chamber or nearby structure 110 and input into the at least one of the at least one gonioscopic optical elements is directed, e.g., refracted, in the same dimension (e.g., more parallel to the optical axis 225). The substantially all light may comprise, for example, at least about 80%, 90%, 95%, 99%, 99.5%, or 99.9%.

A gonioscopic optical element may be tilted with respect to the optical axis 225. The tilt may be indicated, for example, by a proximal surface, a distal surface, and/or a midway line comprised of points half-way between the proximal and distal surface that is non-perpendicular to the optical axis 225. In some embodiments, one gonioscopic optical element (e.g., 215) is tilted with respect to another gonioscopic optical element (e.g., 220). The tilt may by indicated, for example, by a proximal surface, a distal surface, and/or a midway line of the one gonioscopic optical element that is non-parallel to a corresponding line or surface of the other gonioscopic optical element.

A gonioscopic optical element may comprise an optically transparent material and/or may be optically transparent. A gonioscopic optical element may comprise, for example, glass, quartz or silica, a transparent plastic, acrylic (e.g., poly(methyl methacrylate)), or other transparent compounds (e.g., ZnS or ZnSe). In some instances, acrylic is used due to its low cost, optical properties, light weight, and/or moldability. In some instances, silica is used, as in a system including one or more silica components that may be associated with less chromatic aberration as to comparable components including a different material.

In some instances, a material of one or more components or elements is light weight. Additionally, one or more components or elements may be small relative to components or elements of other gonioscopic systems (e.g., two mirror designs). Thus, the system may be convenient to use. In some instances, a system disclosed herein does not comprise any mirror surfaces.

In some instances, a material of one or more components or elements may be one which has a refractive index substantially different than air. A difference between a refractive index of the material and air may be, for example, at least about 0.2, 0.4, 0.6, 0.8, 1 or more. High-index materials may provide smaller prism angles, shorter geometrical paths and/or more compact designs. In some instances, a material of one or more components or elements comprises a refractive index of at least about 1.2, 1.4, 1.6, 1.8, 2.0, 2.2 or more.

In some embodiments, some components or elements (e.g., the second gonioscopic optical element 215) are made from a different material than other components or elements (e.g., the third gonioscopic optical element 220). For example, one element may be made of acrylic and another of quartz or Schott PLaSF47. In another example, one element is made of Schott NFk5 glass and another of Schott PLaSF47 glass. Such glass may be moldable. Accordingly, moldable glass may be employed. The optical prescriptions of the optical element can be recalculated to accommodate the refractive indices of these new materials. High refractive index glasses such as Schott NFk5 and PlaSF47 may reduce the chromatic and astigmatic aberrations below those of plastics, such as acrylic.

A gonioscopic optical element may comprise a material that transmits at least about 50%, 60%, 70%, 80%, 90%, 95%, 98%, 99%, 99.5%, or 99% of visible light and/or may produce a reflection of no more than about 10%, 8%, 6%, 4%, 3%, 2% or 1% from each of its surfaces. The material may be readily molded. In one embodiment, the second gonioscopic optical element 215 and the third gonioscopic optical element 220 comprise Schott PLaSF47 glass and the first gonioscopic optical element 210 comprises Schott NFk5 glass.

In some embodiments, one or more components or elements comprise an antireflective coating. The antireflective coating may, for example, coat air-exposed surfaces of the optical elements to improve light throughput and possibly image contrast.

The gonioscopic system may comprise a diffractive optical element. The second gonioscopic optical element 215, for example, may comprise a diffractive element or surface. The diffractive element or surface may reduce chromatic and/or astigmatic aberrations. The aberrations may be reduced, for example, to a level lower than a design that does not include a diffractive optical element. A proximal surface 215d of the second gonioscopic optical element, for example, may comprise and/or be bonded to the diffractive surface or element. The diffractive surface or element may be made by optical lithography, E-beam etching or other fabrication techniques. The diffractive element or surface may be made on the second gonioscopic optical element 215 or it may be made on a separate (e.g., thin) element that is attached or bonded to the second gonioscopic optical element 215. The diffractive element or surface may reduce aberrations. A diffractive element may be mathematically described by a $3^{rd}$ order XY polynomial and may have only bi-lateral symmetry. A diffractive element may be made, for example, by etching a depth (phase) profile comprising fine step or 'sawtooth' features into a flat surface (e.g., using photolithography). Plastic injection molding may also be used.

In certain embodiments, the first and second gonioscopic optical elements comprise diffractive optical elements. In some embodiments, each of the gonioscopic optical elements comprises a diffractive optical element. In certain embodiments, only diffractive optical elements are used.

A system may or may not include an output lens (e.g., after an nth gonioscopic optical element). Vergence considerations (e.g., relating to a microscope) may affect whether a lens is included. The lens may be round and may cause the exit beams of the gonioscope to diverge to enhance illumination light capturing.

One or more optical components or elements described herein may be supported by a supporting structure. The supporting structures may, for example, control relative positions and/or optical alignment of the components and/or elements. The supporting structure may define a longitudinal axis. The gonioscopic optical elements may be arranged along an axis parallel to this longitudinal axis.

Figure 5B:
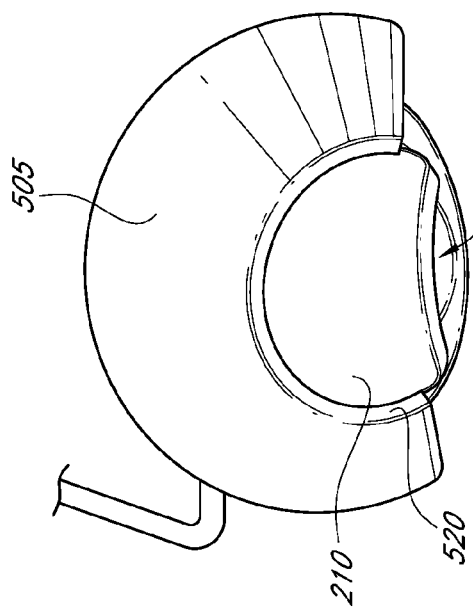
FIGS. 5A-5D schematically illustrate a gonioscopic optical system comprising a housing and handle.
Figure 5D:
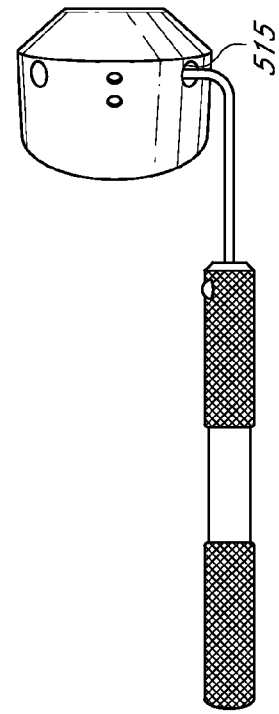
Figure 5A:
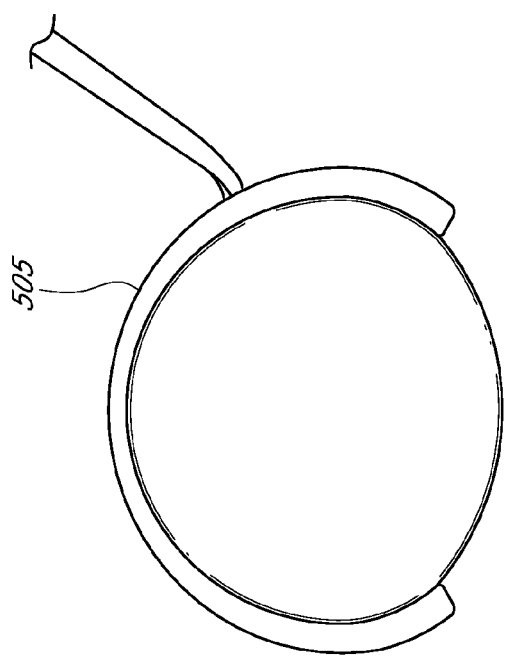
Figure 5C:
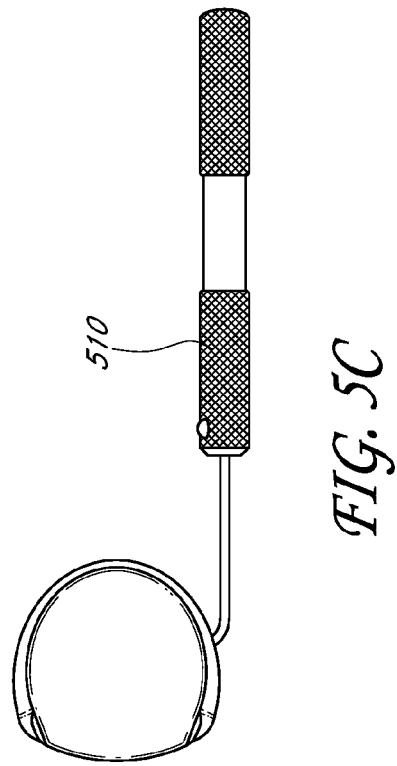

As shown in FIGS. 5A-5D, a system disclosed herein may comprise a housing 505. The housing 505 may comprise, for example, a tube, a case, a cylinder or a box. Other types of lens retainers may be employed. The housing 505 may comprise an open housing having opening or apertures therein, such that, for example, the first gonioscopic optical element 210 is accessible (e.g., to be placed on a subject's eye). Light can thus enter and exit the housing 505 passing through the gonioscopic optical elements therebetween. As shown in FIGS. 5C-D, the housing 505 may be attached to a handle 510 or grip, configured to allow a user to lift the housing and components and/or elements contained within and move it, for example, towards a subject's eye. The handle 510 or grip may comprise, for example, a pivot connection 515 such as a hinge, configured such that an orientation of the handle 510 or grip may be changed (e.g., depending on whether a user uses his right or left hand). A material of the housing 505 and/or the handle 510 or grip may include, for example, a metal (e.g. steel, titanium, or stainless steel), plastic, and/or acrylic. In some embodiments, a system disclosed herein comprises a housing 505 (e.g., a lens retainer) and/or a handle 510 that can be sterilized or is designed with inexpensive material such as plastic and is disposable after a single use.

The housing 505 may comprise a first dimension (e.g., a length dimension) of at least about, about or less than about 50, 40, 30, 20, 15, 12, 10, 8, 6, or 4 mm. The housing 505 may comprise a second dimension (e.g., a diameter dimension) of at least about, about or less than about 50, 40, 30, 20, 15, 12, 10, 8, 6, 5, 4, 3 or 2 mm.

As shown in FIG. 5B, the housing 505 may comprise a subject-contact portion 520. The subject-contact portion 520 may be positioned on an ocular structure of a subject (e.g., a cornea surface) or a subject's skin (e.g., skin surrounding the subject's eye). The subject-contact portion 520 may comprise a rounded and/or smooth surface, which may reduce injury or scratching of the cornea surface. As described above, this surface may have a curvature substantially the same as that of the cornea. In some embodiments, for example, the radius of curvature ranges between about 5 mm and 11 mm. In some embodiments, the subject-contact portion 520 comprises, for example, a (e.g., greatly rounded) ridge or foot, which, when it comes in contact with the cornea, can be gently pressed into the cornea, providing a degree of anchorage and/or stabilization for a system disclosed herein. A' recess 525 is also shown. This recess 525 may provide access for a tool or applicator to be inserted between the surface and the cornea, for example, to insert hardware such as a stent into the eye. If the subject-contact portion 520 is pressed into the region next to the cornea, it may be possible to "open" the angle to increase the view into the angle. Various materials can be used between the first gonioscope optical element and the patient's eye to reduce reflection of light as it passes from the patient's eye to the first gonioscope optical element. In some embodiments, an index matching fluid (e.g., a viscoelastic gel) and/or index matching film may be used between the cornea and the surface of the first gonioscope optical element.

A system disclosed herein may be packaged in a container (e.g., a plastic container). The container may comprise a peel-away lid. The lid may comprise, for example, polyethylene, such as flashspun high-density polyethylene fibers registered under the trademark of Tyvek®.

The entire package may be sterilized by, for example, ethylene oxide gas or Gamma radiation at a suitable level to assure that the contents are sterile. In some embodiments (e.g., those comprising plastic components or elements or those comprising an all plastic design), a system may be presterilized. This may reduce or eliminate the need to sterilize the system before use, using, for example, autoclave, ethylene oxide, or soaking in gluteraldehyde. As sterilizations can be messy and/or time consuming, a presterilized gonioscopic system provided herein may reduce time, preparation time, costs and/or inconvenience associated with gonioscopic procedures. A presterilized gonioscopic system provided herein may, for example, be more convenient than other gonioscopic systems for a surgeon because it is furnished sterile, in a proper sterile barrier package like other single use medical devices. In some embodiments, a kit is provided comprise a gonioscopic system (e.g., a presterilized gonioscopic system) and other surgical tools (e.g., to create procedure trays).

Figure 6:
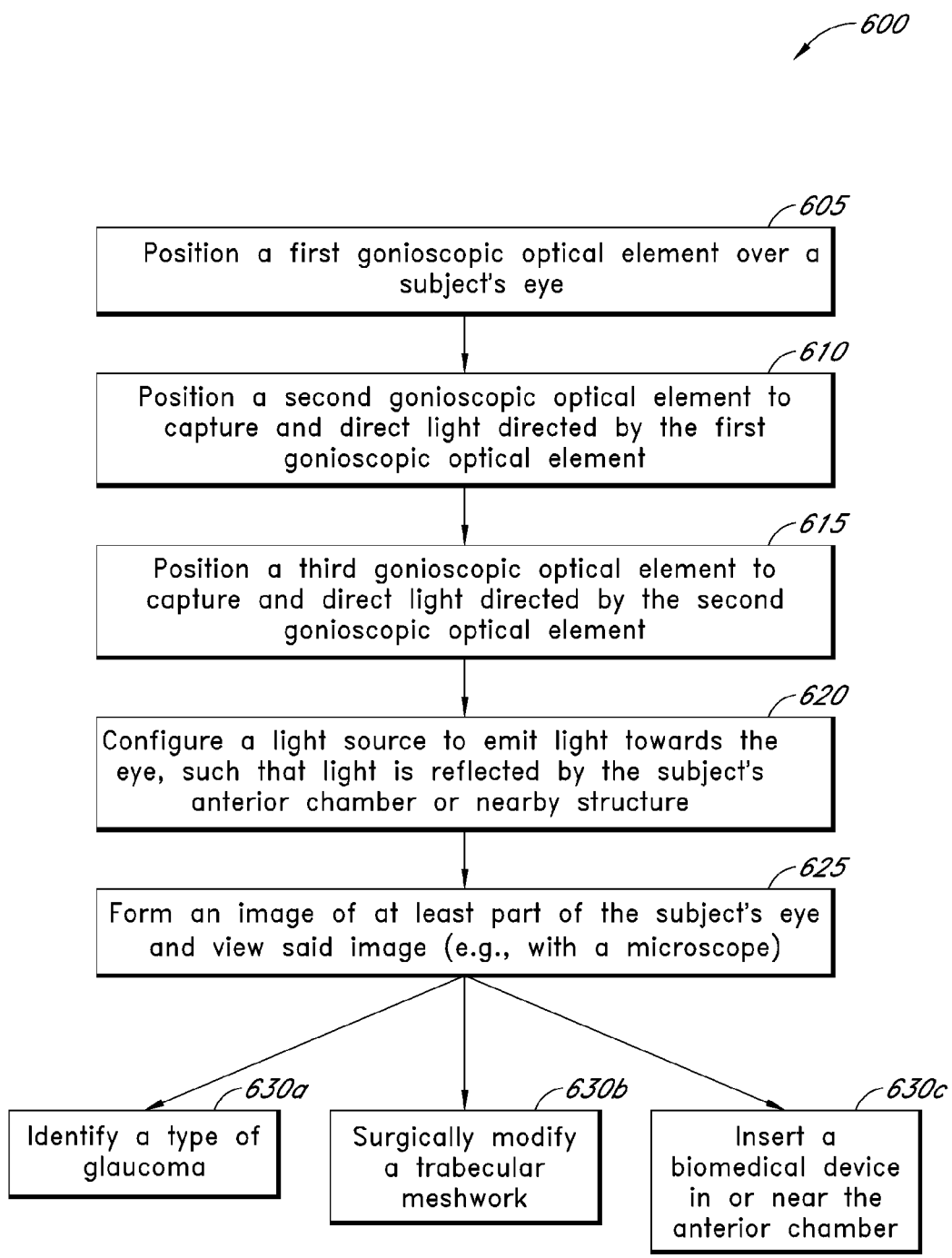
FIG. 6 shows a process for imaging an anterior chamber, an anterior chamber angle and/or a Trabeculum.

FIG. 6 shows a process 600 for imaging an anterior chamber, an anterior chamber angle and/or a Trabeculum of a subject's eye. The user may initially position the head of the subject. This step is not shown by a separate block in FIG. 6. At step 605, first gonioscopic optical element 210 is positioned over or on the subject's eye (e.g., a cornea of the subject's eye). At step 610, a second gonioscopic optical element 215 is positioned to capture and redirect light directed by the first gonioscopic optical element 210. At step 615, a third gonioscopic optical element 220 is positioned to capture and redirect light directed by the second gonioscopic optical element 215. In some embodiments, each of these elements 210, 215 and 220 are individually positioned. In other embodiments, the elements are arranged within a system, such that the relative locations of the elements with respect to each other and to other system elements or components, are substantially fixed following the arrangement. Thus, by positioning the system or a single element or component of the system, the elements 210, 215 and 220 are all positioned. As described above, the distal surface of the first gonioscopic optical element may be shaped to fit over the cornea of the eye. In some embodiments, the positioning steps 605, 610 and 615 comprise positioning a subject-contact portion of the system on a subject's eye or positioning a ridge or foot of the system on the subject's eye. In some embodiments, by positioning a system component on the subject's skin (e.g., skin surrounding the subject's eye), the elements are positioned.

In some embodiments, the subject's head is positioned substantially looking vertical, for example, with the subject in a supine position. For example, implantation of a stent into the trabecular meshwork can be performed after a cataract procedure, which is also done with the subject's head oriented such that the optical axis is directed vertically. Thus, systems provided herein that allow viewing of the trabecular meshwork while the subject's head is oriented such that the optical axis of the eye is directed vertical may be more convenient over other gonioscopic systems, for which a subject's head is typically tilted (e.g., by about 30 degrees) and/or for which a microscope is tilted.

At step 620 of process 600, a light source is configured to emit light towards the subject's eye. The light source may be configured such that light from the source illuminates the subject's eye, anterior chamber, and/or a structure near the anterior chamber (e.g., Trabecular meshwork) or such that one or more of these structures reflects light from the source.

In various embodiments, the light source may comprise, for example, one or more light emitters such as light emitting diodes (LEDs) mounted to a microscope. In some embodiments, for example, the light source comprises are a ring disposed, for example, about the input aperture of the microscope. Other types of light sources may be employed.

In some instances, light from the light source traverses one or more optical components or elements before reaching the subject's eyes. The optical components or elements may change the path of the light, in which case, directing the light source may include directing the source itself toward the eye such that light originating from the source and output at the eye will illuminate the subject's eye or specific ocular structure such as the Trabeculum.

In some embodiments, a system described herein is configured such that a substantial portion of light from the source illuminates the eye. This may be accomplished due to the size and/or alignment of the components or elements of the system. In some microscopes, a coaxial illumination illuminates up to 100% of the surgical visual field. In other microscopes, a ring illuminator can illuminate 100% of the surgical field but with less intensity than a coaxial illuminator. The intensity of the light can be adjusted from 0 to 100% of maximum as desired by the surgeon. In some instances, the proportion of light originating from the source that reaches the eye is greater than for other gonioscopic systems, such as dual-mirror designs and the Mori gonioprism. Thus, a system configured herein may be associated with brighter, higher contrast images.

The light source and elements 210, 215 and/or 220 may be configured such that light from the source is reflected by the subject's eye or specific ocular structure, traverses the first gonioscopic optical element, is redirected, e.g., refracted, diffracted, by any one of or combination of the gonioscopic optical elements. At step 625 of process 600, an image is formed of at least part of the subject's eye. This image is upright (uninverted). This image may be a virtual (not real) image. This virtual image may be viewed using the microscope. The microscope may comprise optics disposed at a distance and lateral position to reimage the virtual image in the viewer or user's eye.

The at least part of the subject's eye may include, for example, an anterior chamber, an anatomic structure near the anterior chamber, such as a Trabecular meshwork, or an artificial structure placed in or near the anterior chamber (e.g., a stent). In some instances, a user can see the image through a microscope as the object is changing or being operated on. The image may be recorded by a camera and be output (e.g., to a computer or to a display) and/or may be stored (e.g., on a storage component, such as a computer storage unit, compact disc, or USB drive).

In some instances, the first and second gonioscopic optical elements 215 and 220 are positioned such that there is a short, direct optical path through the two elements. The optical path may be, for example, shorter than an optical path through other dual mirror or Mori prism gonioscope designs. The optical path may be less than about 10 mm or 15 mm. This may improve, for example, the surgical field of view. The short direct optical path may provide a wide field of view and may remove the confusing multiple reflections from the mirror surfaces associated with other gonioscopic designs. The elements may be configured such that there is no image inversion. Zero or an even number of reflections are to be used to form the image of the object in the eye, thereby preserving the handedness or parity of the image. In some instances, the image formed is shifted laterally by a distance less than about 1 to 2 mm and longitudinally by a distance of less than 2 to 15 mm.

Various method steps may be performed using the image produced at step 625. The image may be used, for example, to identify or diagnose a medical condition, assess a treatment, perform a surgery, and/or identify a location to insert a biomedical device. At step 630*a*, a type of glaucoma is identified based at least partly on the image formed. In some instances, a depth of the subject's anterior chamber is determined based on the image. The identified glaucoma type may be one that the subject is likely suffering from or one that the subject has a risk of suffering from. The glaucoma type may include, for example, narrow-angle glaucoma.

At step 630*b*, a trabecular meshwork is surgically modified based at least partly on the image. In these instances, the image may comprise an image of at least part of the trabecular meshwork. The surgical modification may comprise a trabeculectomy. In some instances, at least part of the trabecular meshwork is removed, which may thereby create an opening that allows aqueous humor to drain from the subject's eye. This step may be performed, for example, for subjects suffering from glaucoma (e.g., open-angle glaucoma).

At step 630*c*, a biomedical device is inserted in or near the anterior chamber based at least partly on the image formed. The biomedical device may comprise, for example, a stent and/or a drug eluting implant (with or without draining capabilities). The biomedical device may be positioned through a trabecular meshwork or implanted at other locations (e.g., near the scleral spur to drain to the suprachoriodal space). Thus, the image formed at step 625 may comprise an image of at least part of the trabecular meshwork or other anatomical structures.

In some instances, the subject is suffering from or is at risk of suffering from an ophthalmic condition. The ophthalmic condition may be related to the anterior chamber, the trabecular meshwork and/or the aqueous humor. The ophthalmic condition may comprise cataracts or glaucoma. In some instances, the subject has been and/or is being treated for the ophthalmic condition. The subject may have recently (e.g., within about a week, a day, an hour, 30 minutes, 15 minutes, 5 minutes or less) undergone cataract surgery. The subject may be resistant to one or more treatments. The subject may have one or more visual impairments. In some instances, the subject is not known to be suffering from any ophthalmic conditions.

EXAMPLES

Example 1

Figure 7:
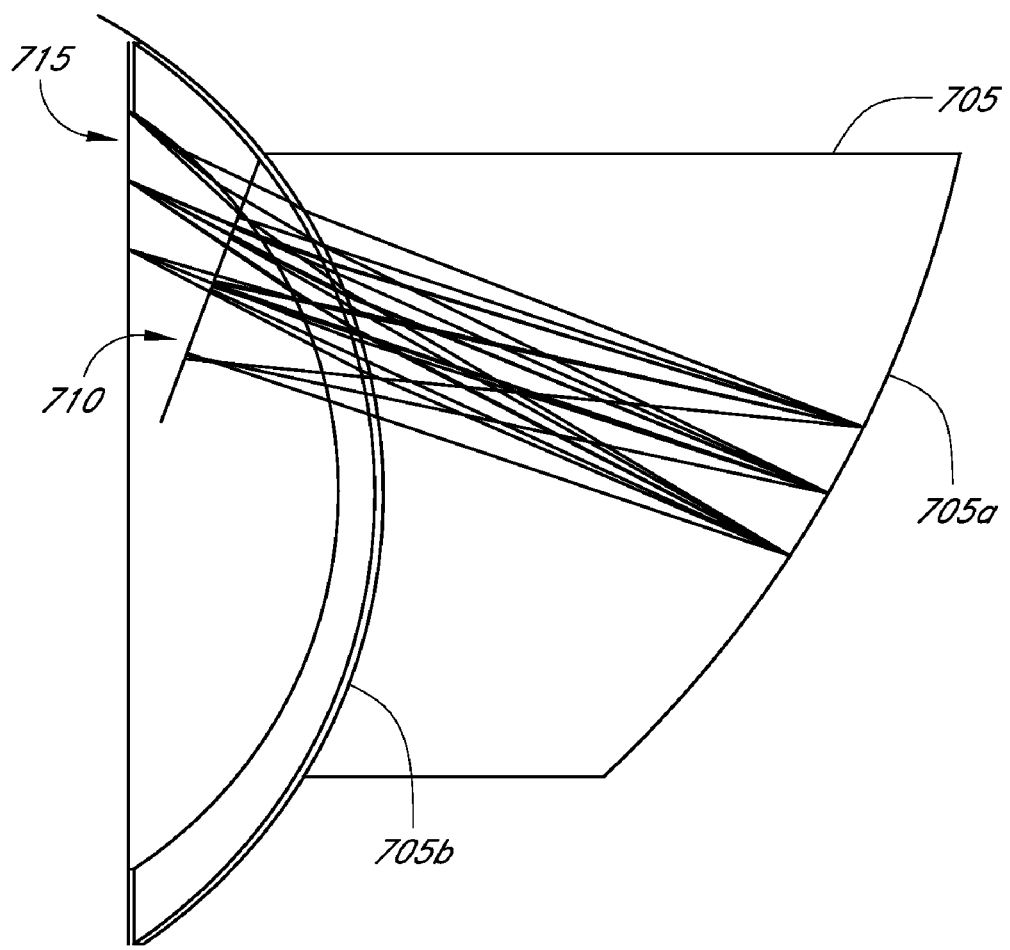
FIG. 7 shows a ray trace of an example gonioscopic optical system comprising a Hill Gonioscope.

FIG. 7 shows a ray trace of an example gonioscopic optical system comprising one single gonioscopic optical element 705, such as the system 100 shown in FIG. 1. The gonioscopic optical element comprises a toroidal proximal surface 705a and a spherical distal surface 705b, the spherical distal surface substantially matching the shape of the cornea to fit over the eye.

The object is in a plane referred to as the object plane and the image is generally in a correspondingly plane referred to as the image plane. The image plane 710 is tilted with respect to the object plane 715. This tilt may be about 5 to 15 degrees. Due to this tilt, subjects and/or microscopes may need to be tilted during, for example, surgical operations in order to allow visualization of structures at or near the angle.

Example 2

Figure 8A:
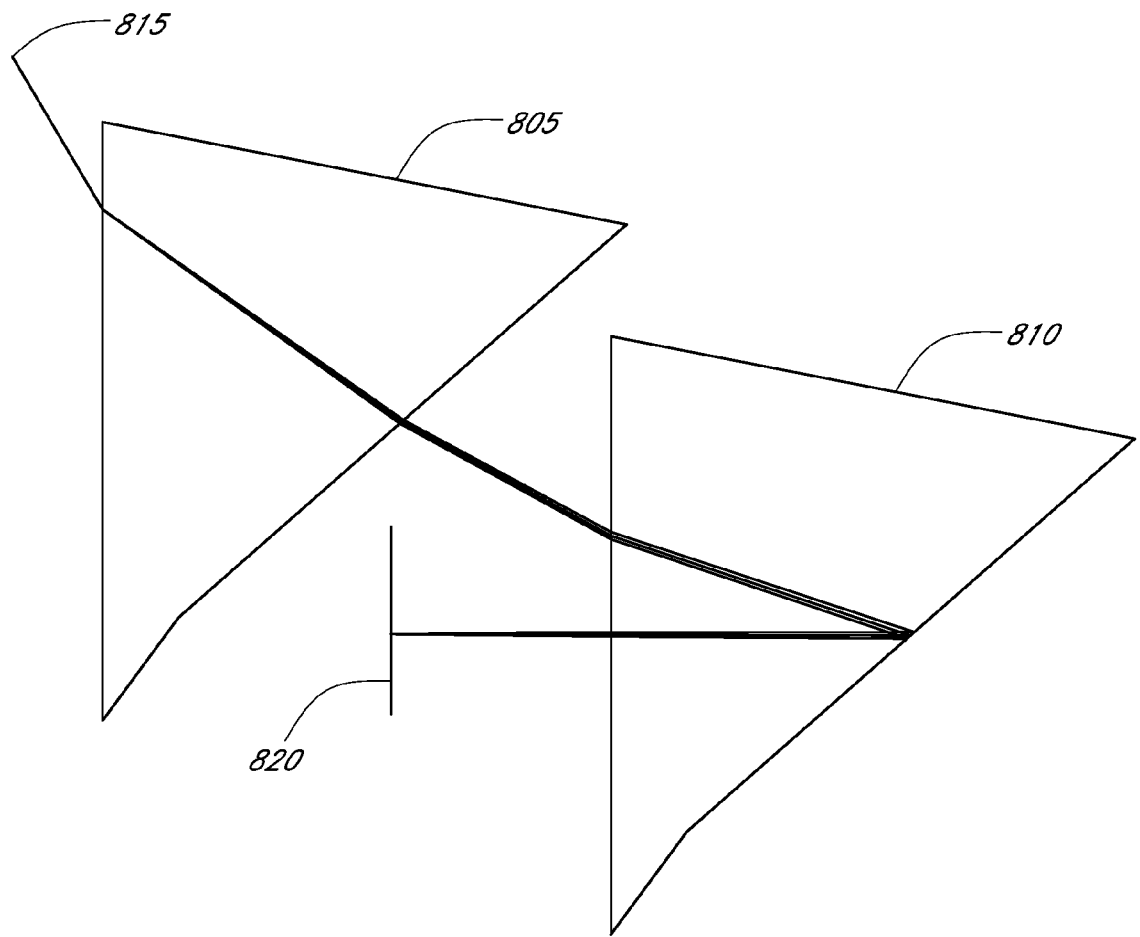
FIGS. 8A and 8B show ray traces for a gonioscopic optical system comprising a plurality of wedge shaped prisms.
Figure 8B:
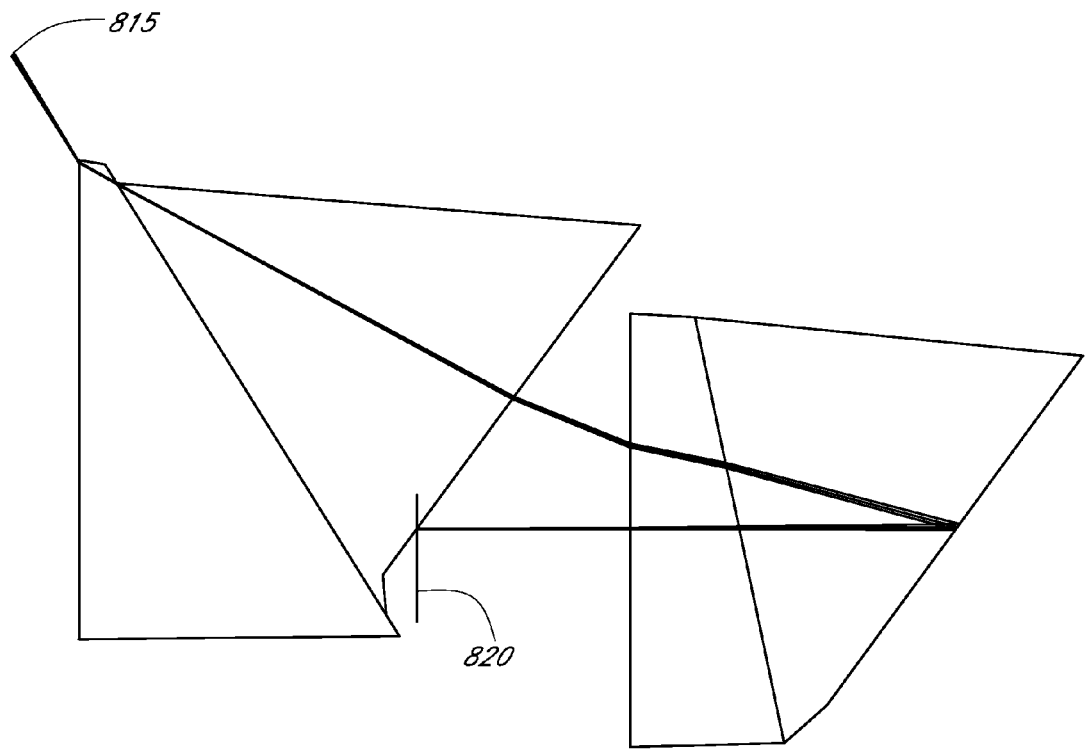

With other designs, light reflected from the object plane 715 such as shown in FIG. 7 may be directed, such that the image plane is parallel to the object plane. FIGS. 8A and 8B show ray traces for systems comprising a plurality of prisms configured to turn light reflected from the object 815 (e.g., trabeculum) at the object plane such that an image (e.g., virtual image) is produced on an image plane 820 that is parallel with the object plane. The prism components may then make unnecessary tilting the head of the subject and/or the microscope while viewing the ocular structure.

FIG. 8A shows a ray trace of an example optical system comprising two prisms. Prisms 805 and 810 comprise large apex angles in order to turn the light by a large angle. Such large prism sizes may be undesirable for gonioscopic systems. This configuration may be undesirable because with certain apex angles and prism material refractive indices, the image may be lost because of total internal reflection in the prism. Additionally, lateral color and astigmatism is induced by the prism pair.

By using prism pairs with differing indices of refraction, chromatic aberrations can be reduced. The astigmatism, however, may be increased. (Chromatic aberration may cause image spectral "streaking" in one direction that can impair image visualization.).

FIG. 8B shows a ray trace when multiple prisms are included comprising glasses with different dispersive properties. The beams are substantially achromatized, but the larger prisms are still used to turn the beam. For example, the prisms are larger than those in FIG. 8A. Additionally, although the lateral color has been reduced, an anamorphism and astigmatism is increased compared to that in FIG. 8A because the glass is thicker.

Thus, using the prisms of FIGS. 8A and 8B alone or integrating these prisms with the system shown in FIG. 7, includes possible drawbacks such as larger size of the components, and/or larger anamorphism and lateral color associated with one or more of the configurations.

Example 3

Figure 9:
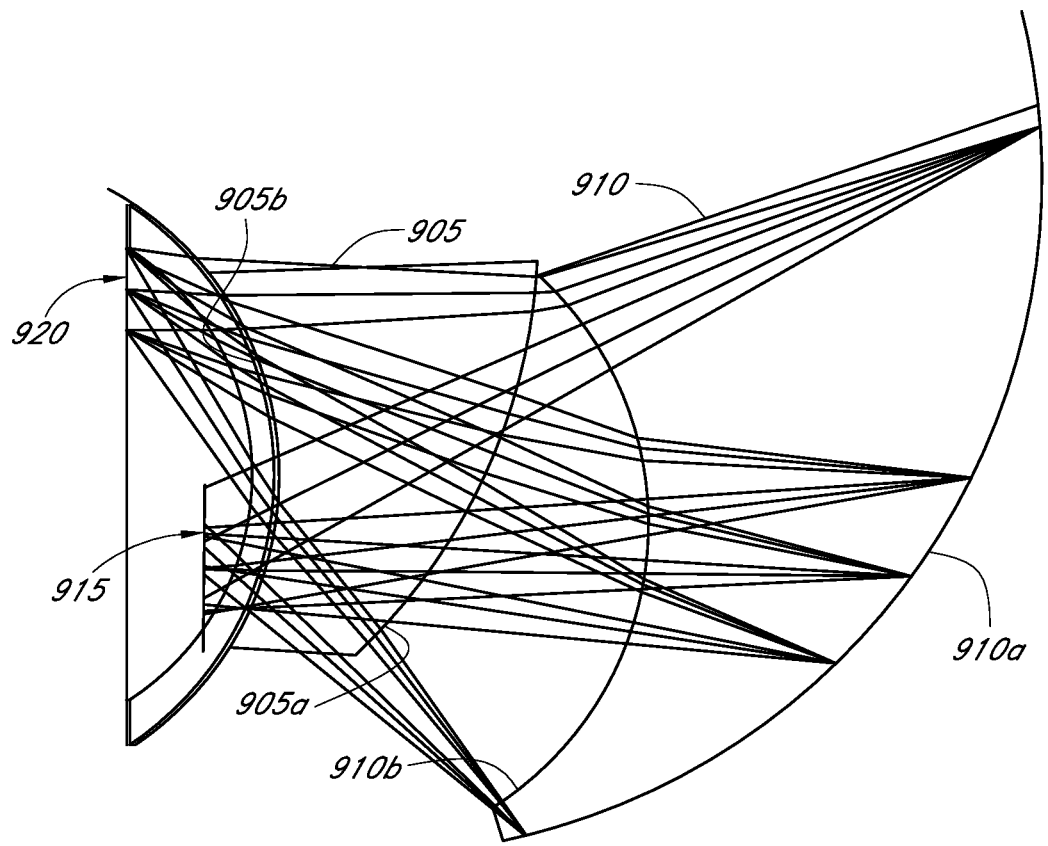
FIG. 9 shows a ray trace of an example gonioscopic optical system comprising two acrylic toroidally shaped gonioscopic optical elements.

FIG. 9 shows a ray trace of an example gonioscopic optical system such as the system 200 shown in FIG. 2 comprising gonioscopic optical elements 905 and 910 comprising curved surfaces. In particular, the two acrylic toroidal gonioscopic optical elements 905 and 910 each having toroidal surfaces. Such toroidal surfaces can have different radii of curvature in different orthogonal directions. A corresponding optical prescription in Code V® by Optical Research Associates Pasadena, California, is shown in Tables 1A-C. Injection molded plastic may be used to fabricate such as system. In this instance, optical element 905 comprises a distal surface having a spherical shape substantially matching the shape and size of the cornea of an eye so as to provide a good fit with the subject's eye. The elements 905 and 910 are made of acrylic. Additionally, the proximal surfaces 905a and 910a of the elements, as well as the distal surface 910b of the second gonioscopic optical element 910 comprise toroidal surfaces. These surfaces are off-axis (tilted and/or decentered) with respect to the optical axis of the eye. In this instance, the orientation of the image plane 915 is nearly at parallel to the orientation of the object plane 920. The image plane 915 is displaced longitudinally about 3 millimeters from the object plane and is posterior to or more distal than the first gonioscopic optical element. However, lateral color associated with this system may degrade the polychromatic resolution of the gonioscopic optical system.

Example 4

Figure 10:
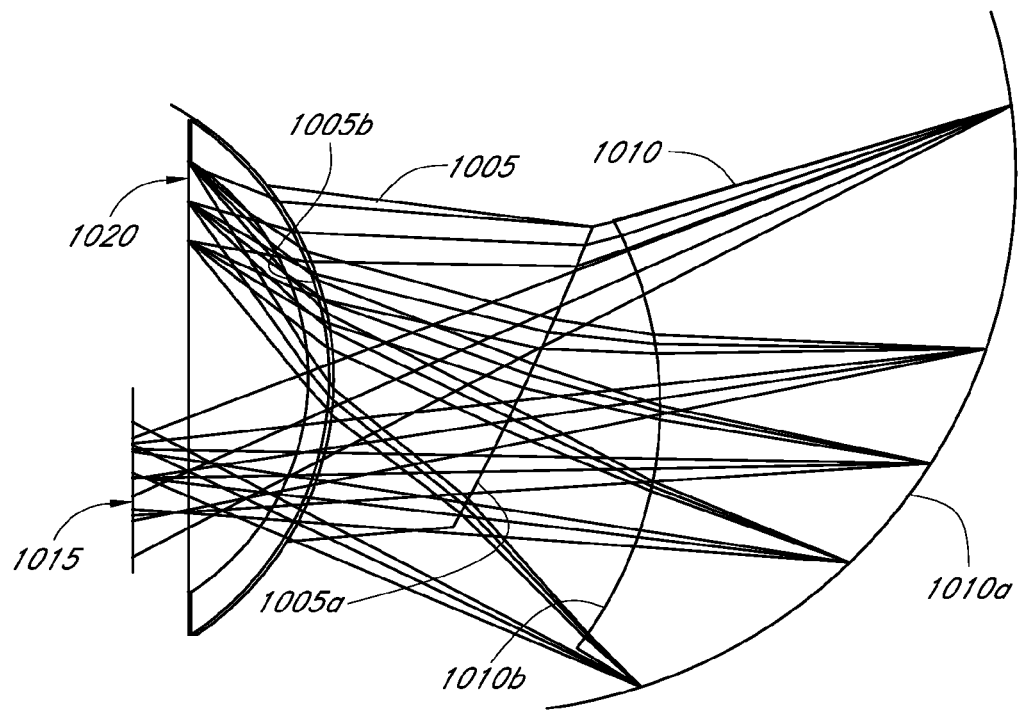
FIG. 10 shows a ray trace of an example gonioscopic optical system comprising two glass gonioscopic optical elements.

FIG. 10 shows a ray trace of an example gonioscopic optical system comprising two glass gonioscopic optical elements 1005 and 1010. A corresponding optical prescription in Code V® by Optical Research Associates Pasadena, California, is shown in Tables 2A-C. In this instance, optical element 1005 comprises a distal surface having a spherical shape substantially matching the shape and size of the cornea of an eye so as to provide a good fit with the subject's eye. The gonioscopic optical element 1005 is made of Schott NFk5 glass and the gonioscopic optical element 1010 is made of Schott PLaSF47 glass. The proximal surfaces 1005a and 1010*a* of the elements, as well as the distal surface 1010*b* of the second gonioscopic optical element 1010 comprise spherical surfaces. These surfaces are off-axis (tilted and/or decentered) with respect to the optical axis of the eye. In this instance, the orientation of the image plane 1015 is nearly at parallel to the orientation of the object plane 1020, and the image plane 1015 is about 2 millimeters to the object plane 1020. In the embodiment shown, the image plane 1015 is displaced longitudinally about 3 millimeters from the object plane and is posterior to or is more distal than the first gonioscopic optical element as well as posterior to the object plane. However, lateral color associated with this system may degrade the polychromatic resolution of the optics. The lateral color associated with this system may, however, improve the polychromatic resolution as compared to other embodiments (e.g., where a single material is used for both gonioscopic optical elements 1005, 1010).

Example 5

Figure 11:
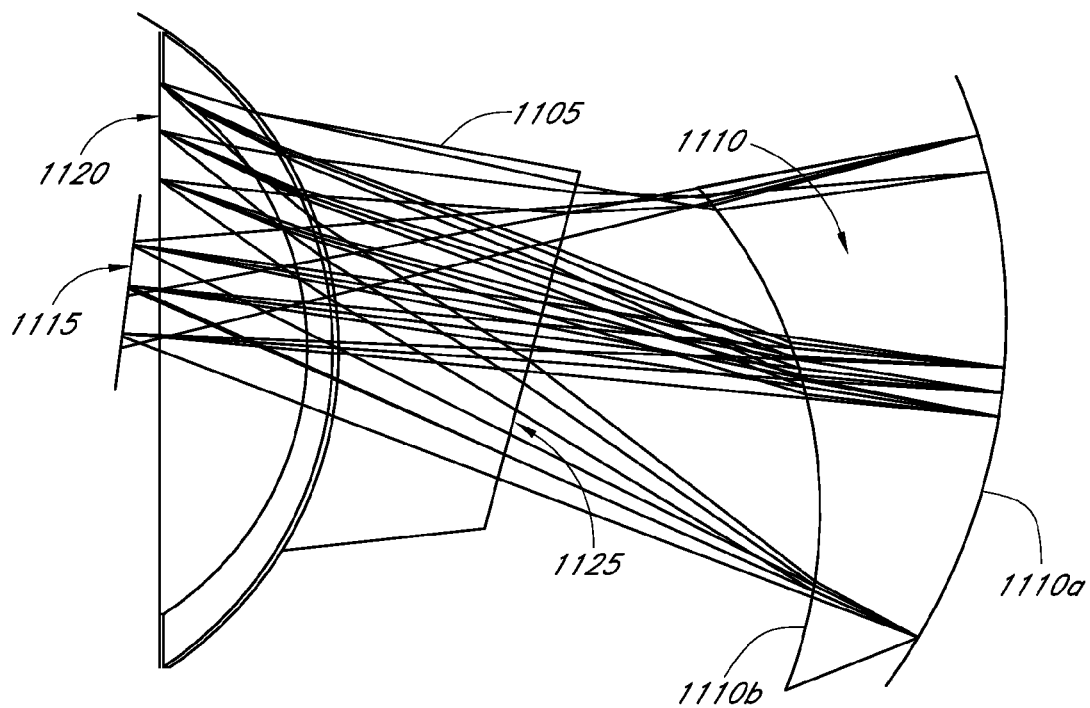
FIG. 11 shows a ray trace of an example gonioscopic optical system comprising two gonioscopic optical elements, one of which includes a diffractive surface.

FIG. 11 shows a ray trace of an example gonioscopic optical system comprising two toroidal gonioscopic optical elements 1105 and 1110, one of which comprises a diffractive surface 1125. A corresponding optical prescription in Code V® by Optical Research Associates Pasadena, California, is shown in Tables 3A-D. In this instance, optical element 1105 comprises a distal surface having a spherical shape substantially matching the shape and size of the cornea of an eye so as to provide a good fit with the subject's eye. Additionally, optical element 1105 comprises a diffractive surface 1125 disposed on a silica substrate. The diffractive optical element has dispersion that reduces chromatic aberration otherwise produced by said first and second gonioscopic optical elements. The optical element 1110 is made of acrylic. The proximal and distal surfaces 1110*a* and 1110*b* of the second gonioscopic optical element 1110 comprise toroidal surfaces. These surfaces are off-axis (tilted and/or decentered) with respect to the optical axis of the eye. In this instance, the orientation of the image plane 1115 is tilted with respect to the orientation of the object plane 1120. This tilt is between about 6 to 7°. In the embodiment shown, the image plane 1115 is displaced longitudinally about 2 millimeters from the object plane and is posterior to or is more distal than the first gonioscopic optical element as well as posterior to the object plane. Reduced lateral color is observed and high optical resolution is obtained.

Figure 12A:
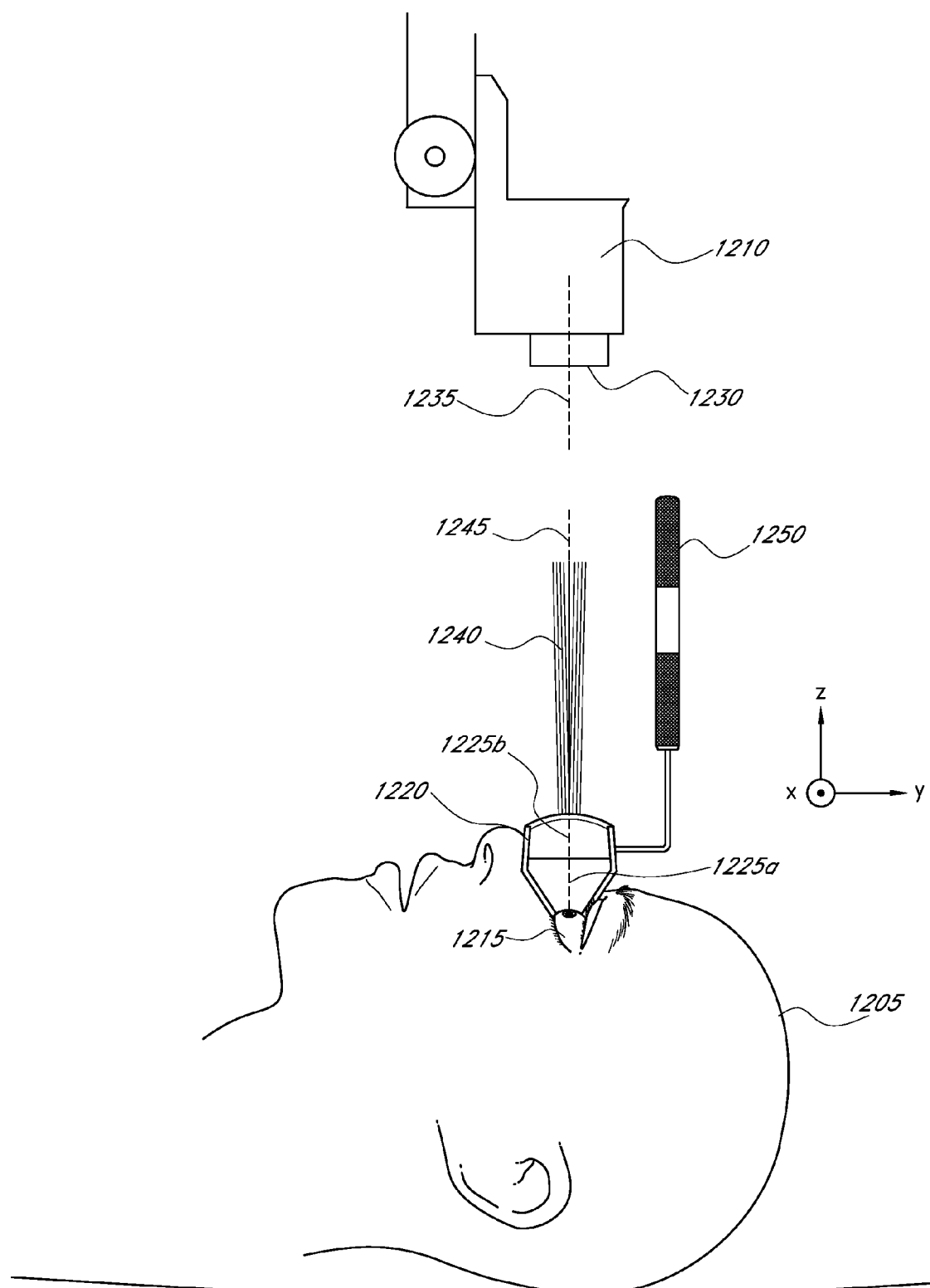
FIGS. 12A and 12B schematically illustrate a patient supine beneath a surgical microscope and having a gonioscope optical element disposed over the patient's eye.
Figure 12B:
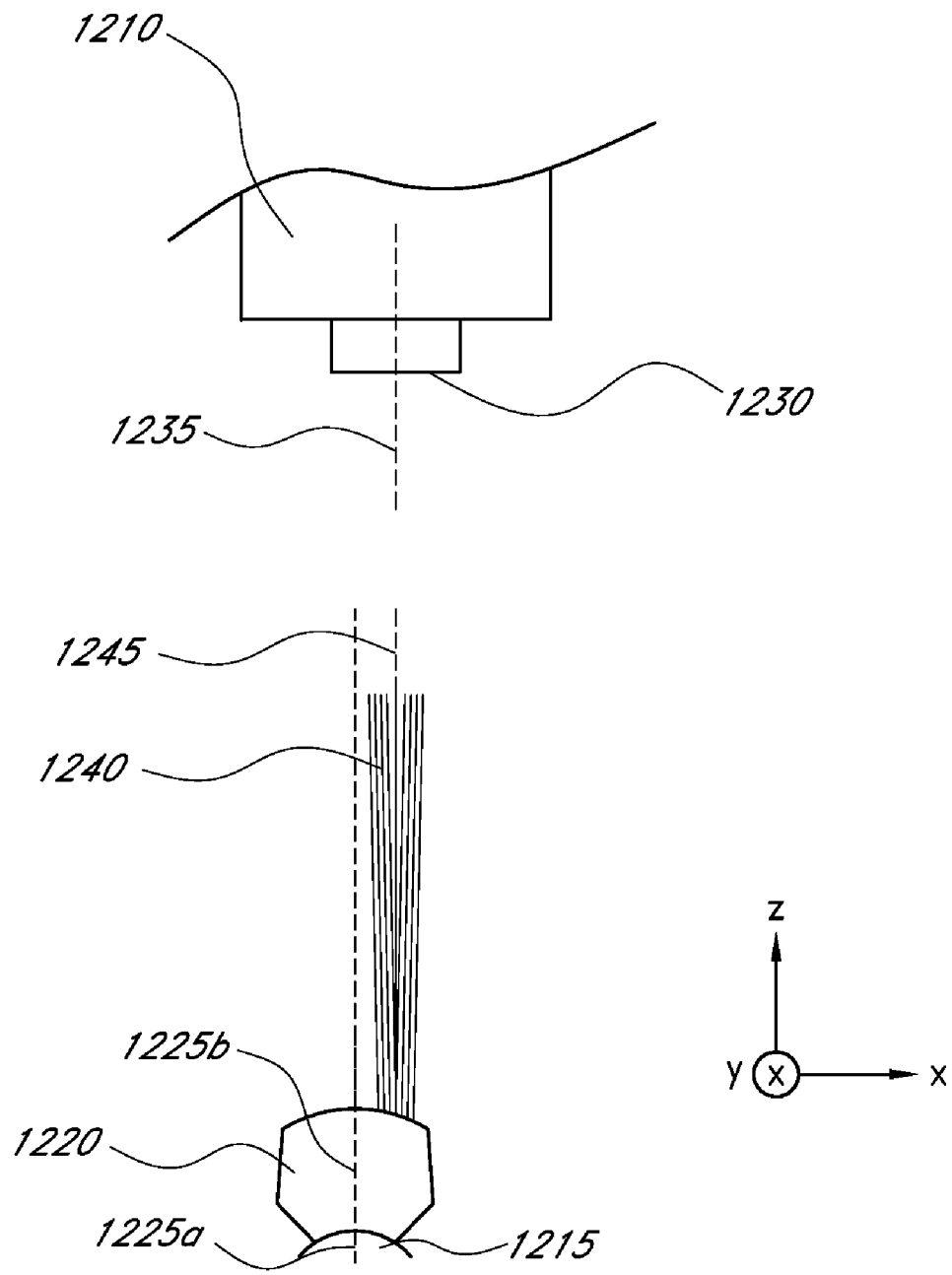

Accordingly, various embodiments include gonioscopic optical systems that form an image that is viewable by a microscope. FIGS. 12A and 12B show a subject 1205 in supine position. FIG. 12A is a view of the subject 1205 from the side showing mainly the subject's head. FIG. 12B is a view as seen when looking superiorly (toward top of the subject's head) showing the front portion of the subject's eye 1215.

A microscope 1210 is disposed above the subject's head and moreover, above the subject's eye 1215 for viewing into the eye. A gonioscope 1220 is positioned on the eye 1215. The optical axis 1225*a* of the eye 1215 and the optical axis 1225*b* of the gonioscope 1220 are aligned. Rays of light are shown exiting the gonioscope 1220 and entering an input aperture 1230 of the microscope 1210. The microscope 1210 has an optical axis 1235 that is generally aligned with the beam 1240 exiting the gonioscope 1220 as indicated by the alignment of the optical axis 1235 of the microscope 1210 and the axis 1245 through the center of the beam 1240. FIG. 12B shows that the beam 1240 of light is displaced laterally (e.g., temporally, when imaging an object on the nasal side of the eye) with respect to the optical axes 1225*a*, 1225*b* of the eye 1215 and of the gonioscope 1220. The gonioscope 1220 includes a handle 1250. The placement of the handle 1250 need not be limited to that shown in FIG. 12A. (This handle 1250 is not shown in FIG. 12B for clarity.)

This image formed by the gonioscopic optical systems that is viewable by a microscope may be of an object at a region lateral to the optical axis of the eye. In various embodiments, for example, this object is nasal to the optical axis, by about 0 mm to 10 millimeters. This object may also be displaced longitudinally 0 mm to 10 millimeters from the apex of the cornea. This object may be displaced longitudinally 0.5 mm to 10 millimeters from the apex of the cornea as the thickness of the average cornea is about 0.5 mm. Similarly, the object may be lateral to the optical axis of the gonioscopic optical system and distal to the distal surface of the first gonioscopic optical element. In some embodiments, for example, the object is about 0 mm to 10 millimeters lateral to the optical axis of the gonioscopic optical system and about 0.5 mm to 10 millimeters distal to the most proximal point (e.g., apex) of the curved distal surface of the first gonioscopic optical element or between about 500 microns to 10,000 microns from the closest portion of the distal surface of the first gonioscopic optical element. The object may be disposed on the perimeter of the first gonioscopic optical element or the distal surface thereof. In some embodiments, for example the object may be disposed within 1, 2, 3, 4, 5, 6, 7, 8, 9, or 10 millimeters of the perimeter of the first gonioscopic optical element or the distal surface thereof. As described above, the object may be in a plane referred to as the object plane and the image may generally be in a plane referred to as the image plane.

This image may be an uninverted virtual image. In various embodiments this gonioscopic optical system has negative optical power. The magnification may be greater than about 0.7× and may be between about 0.5× and 0.99×. The gonioscopic optical system may provide magnification such that the image of the object is larger than the object. The image may be tilted with respect to the object plane by no more than 20°, 15°, 10°, 5°, 1°, 0.5° or may not be tilted at all with respect to the object plane.

In various embodiments, the subject is in a supine position with the person's head neither inclined nor declined at an angle greater than 20°, 10°, 5°, 3°, or 1°. In certain embodiments, the person's head neither inclined nor declined. Likewise, the eye is viewed with a microscope at an angle of no more than 20°, 15°, 10°, 5°, 3°, or 1°. In certain embodiments, the image is viewed by a microscope from directly in front of the image or head, not at an angle with respect to the image or head. Similarly, the optics of the microscope may define an optical axis, and the optical axis of the microscope and the optical axis of the eye are angled with respect to each other by no more than 20°, 15°, 10°, 5°, 3°, or 1°. In certain embodiments, the optical axis of the microscope and the optical axis of the eye are parallel.

Similarly, in various embodiments, the first and second gonioscopic optical elements define an optical axis and the image is less degraded when viewed from an angle of less than 20°, 15°, 10°, 5°, 2°, or 1° with respect to the optical axis of the gonioscope optical elements than when viewed at an angle greater than 20°, 15°, 10°, 5°, 2°, or 1° with respect to the optical axis. The image may be less degraded when viewed parallel to the optical axis than when viewed at an angle with respect to the optical axis.

In some embodiments, the gonioscopic optical elements are disposed in a housing that defines a longitudinal axis such that light from the object in the eye exiting most proximal of the gonioscopic optical elements is directed substantially parallel to the longitudinal axis with an average deviation therefrom of no more than 20°, 15°, 10°, 5°, 2°, or 1° from parallel to the longitudinal axis. In some embodiments, the virtual image is less degraded when viewed from an angle of less than 20°, 15°, 10°, 5°, 2°, or 1° with respect to the longitudinal axis than when viewed at an angle greater than 20°, 15°, 10°, 5°, 2° or 1° with respect to the longitudinal axis.

In some embodiments, light from the object in the eye exiting the gonioscopic optical system or the proximal most gonioscopic optical element is directed substantially parallel to the optical axis of the eye or the optical axis of the gonioscopic optical system with an average deviation therefrom of no more than 15°, 10°, 5°, 2°, or 1° from parallel to the longitudinal axis. In some embodiments, the image is less degraded when viewed from an angle of less than 15°, 10°, 5°, 2°, or 1° with respect to the optical axis of the gonioscopic optical system or the plurality of gonioscopic optical elements than when viewed at an angle greater than 15°, 10°, 5°, 2°, or 1° with respect to the optical axis.

In some embodiments, the distal surface of the first gonioscopic optical element is curved. In certain embodiments, it is spherical. In various embodiments, distal surface of the first gonioscopic optical element has a radius of curvature between about 5 mm and 11 mm.

In some embodiments, the proximal surface of the first gonioscopic optical element is substantially planar. In other embodiments, the proximal surface of the first gonioscopic optical element is curved.

In some embodiments, at least one of (i) the proximal surface of the first gonioscopic optical element and (ii) the proximal or distal surfaces of the second gonioscopic optical element is substantially toroidal. In certain embodiments, the both proximal and distal surfaces of the second gonioscopic optical element are substantially toroidal.

In some embodiments, at least one of the proximal surface of the first gonioscopic optical element and the proximal or distal surfaces of the second gonioscopic optical element is substantially spherical. In certain embodiments, the both proximal and distal surfaces of the second gonioscopic optical element are substantially spherical.

In some embodiments, neither the distal nor proximal surfaces of the second gonioscopic optical element have an optical axis that coincides with a rotational axis of symmetry of the distal surface of the first gonioscopic optical element. In some embodiments, the distal surface of the first gonioscopic optical element does not have an axis of symmetry that both intersects the distal surface of the second gonioscopic optical element and is collinear with an axis of symmetry of distal surface of the second gonioscopic optical element. In certain embodiments, at least one of the distal and proximal surfaces on the second gonioscopic optical element does not have an optical axis that is coincident with the optical axis of the eye. In some embodiments, both the distal and proximal surface on the second gonioscopic optical element do not have optical axes coincident with the optical axis of the eye. In some embodiments, the proximal surface on the first gonioscopic optical element does not have an optical axis coincident with the optical axis of the eye.

In some embodiments, at least one of the first and second gonioscopic optical elements has a tapered thickness with an average thickness on a first half that is thicker than the average thickness on a second half. In some certain embodiments, both the first and second gonioscopic optical elements have tapered thicknesses, each with an average thickness on a first half that is thicker than the average thickness on a second half. In some embodiments, the gonioscope can be used to image an object on the nasal side of the eye, and the thick halves of the first and/or second gonioscopic optical elements can be positioned nasal of the thin halves. In other embodiments, the gonioscope can be used to image an object on the temporal side of the eye, and the thick halves of the first and/or second gonioscopic optical elements can be positioned temporal of the thin halves.

In some embodiments, at least one of the first gonioscopic optical element and second gonioscopic optical elements have a tapered thickness with an average thickness on a first side of the optical axis of the eye that is thicker than the average thickness on a second side of the optical axis. In certain embodiments, both the first gonioscopic optical element and second gonioscopic optical elements have tapered thicknesses each with an average thickness on a first side of the optical axis of the eye that is thicker than the average thickness on a second side of the optical axis.

In various embodiments the gonioscope comprises 4, 3, or 2 lens elements. In some embodiments, the gonioscope has a focal length between −150 and −50 millimeters. In certain embodiments, the first and second goniosopic optical elements have an effective focal length between −150 and −50 millimeters.

Certain embodiments include a diffractive optical element comprising a plurality of diffractive features. These diffractive features may have non-linearly varying spacing. These diffractive features may comprise a plurality of ring-shaped features. These ring-shaped features may be elliptical or elongated. The diffractive optical features may comprise spatially varying refractive indices or spatially varying surface topography. The diffractive optical features may comprise, for example, a saw tooth shaped surface or index of refraction profile. The variation in spacing and/or width may be non-linear. The diffractive feature may reduce chromatic aberration or distortion introduced by the anamorphic effect of the prisms (e.g., the first and second gonioscopic optical elements).

Accordingly, certain embodiments comprise a method of viewing an anterior chamber of an eye of a subject, wherein the eye has an optical axis. In this method, a subject's head is positioned for viewing into the eye. A gonioscope comprising at least first and second gonioscopic optical elements is positioned on the eye. In some embodiments, an uninverted virtual image of a portion of the eye is imaged with a beam of light output from the gonioscope that is directed less than 30° with respect to the optical axis of the eye, and this uninverted virtual image is viewed with a microscope. In some embodiments, an uninverted virtual image of a portion of the eye is formed, and the uninverted virtual image is imaged with a microscope having an optical axis that is not angled with respect to the optical axis of the eye by more than 10°.

In some embodiments, the gonioscopic optical elements allow a large amount of overhead light from the surgical microscope to illuminate the patient's eye. Some prior designs (e.g., two mirror designs) block some of the light from the surgical microscope, producing a dimmer image. By allowing more light to enter the eye, some of the embodiments disclosed herein provide improved visibility of the interior of the patient's eye.

Figure 13A:
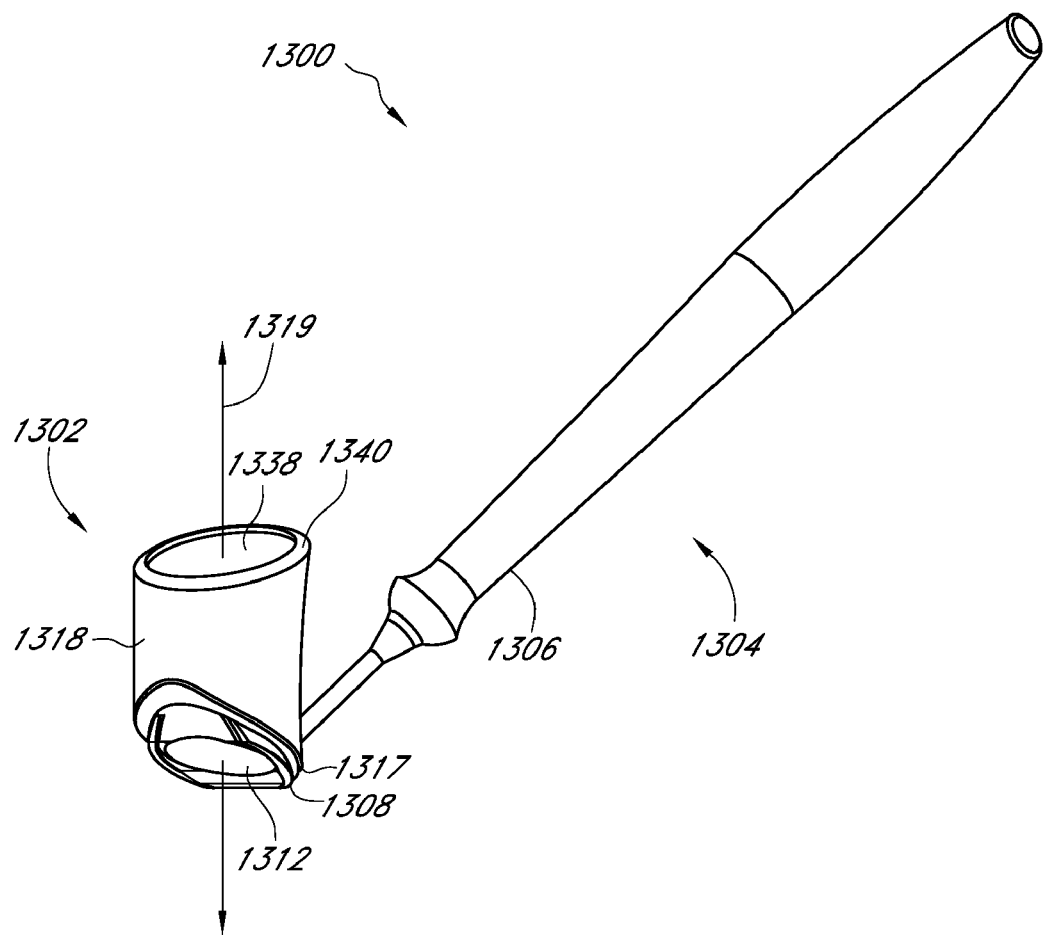
FIGS. 13A-13B schematically illustrate a gonioscopic optical system comprising a gonioscopic attachment configured to attach to a gonioscope.
Figure 13B:
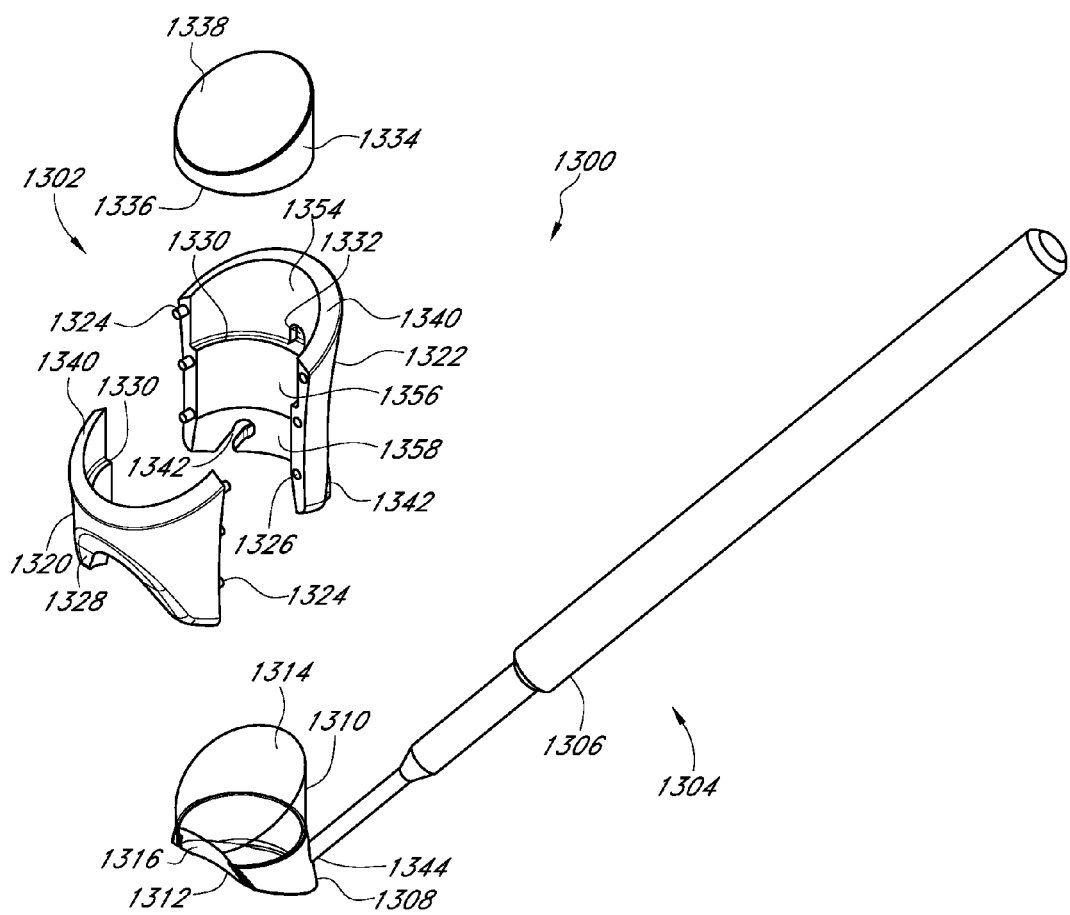

FIGS. 13A and 13B show a gonioscopic assembly 1300 that includes a gonioscopic attachment 1302 that is removably attachable to a gonioscope 1304. FIG. 13A shows the assembly 1300 in its assembled form, and FIG. 13B shows various components of the assembly 1300 separated from each other. The gonioscope 1304 can be a conventional gonioscope, such as the Trabecular Bypass Gonioprism sold by Ocular Instruments located in Bellevue, Wash. The gonioscope 1304 can include a handle 1306 attached to a mounting ring 1308 and a first gonioscopic optical element 1310 secured by the mounting ring 1308. The first gonioscopic optical element 1310 can, for example, be similar to the gonioscopic optical elements 105, 210, 705, 905, 1005, or 1105. The first gonioscopic optical element 1310 can be a contact lens and can include a distal surface 1312 having a spherical shape substantially matching the shape and size of the cornea of an average eye so as to provide a good fit with the subject's eye. In some embodiments, for example, the curved distal surface 1312 may have a radius of curvature between about 5 mm and 11 mm although curvatures outside these ranges are also possible. The first gonioscopic optical element 1310 can also include a proximal surface 1314, which can be planar or have a curved (e.g., toroidal) shape.

The first gonioscopic optical element 1310 can be made of a substantially transparent material (e.g., glass, plastic, silica, or other materials as discussed above) so that light from the subject's eye can be received by the distal surface 1312, propagate through the transparent material, and be emitted by the proximal surface 1314. In some embodiments, the first gonioscopic optical element 1310 includes a recess, relief, or undercut 1316 (as described above), to increase the accessibility and introduction of tools to the cornea, the limbus, or the adjacent scleral or conjunctive tissue of the eye.

The assembly 1300 also includes a gonioscopic attachment 1302 for altering the light emitted by the proximal surface 1314 of the first gonioscopic optical element 1310. The gonioscopic attachment can include a housing 1318 which can be generally tubular in shape, defining an interior chamber. In some embodiments, the housing can also define a longitudinal axis 1319. In some embodiments, the housing 1318 can be configured so that the longitudinal axis 1319 is substantially parallel to the optical axis of the patient's eye when in use with an angle of deviation, for example, of no more than 20°, 15°, 10°, 5°, 2°, or 1° from parallel to the optical axis of the eye.

The housing 1318 can be a two-piece housing including a first piece 1320 and a second piece 1322. The first piece 1320 and the second piece 1322 can include mating structures, such as pins 1324 and bores 1326, configured to allow the first piece 1320 and the second piece 1322 to mate with each other. In some embodiments, the mating structures can be snap-fit structures. In some embodiments, an adhesive can be used to securely mate the first piece 1320 to the second piece 1322. In some embodiments, the housing 1302 can be formed from a single piece. Other configurations are possible. The first piece 1820 can include a tapered surface 1328 configured to align with, or otherwise associated with, the recess, relief, or undercut 1316. The first piece 1320 and the second piece 1322 can include a shoulder 1330, and the second piece 1322 can include a recess 1332 for securing a second optical element 1334 therein. The housing 1318 can be made from a variety of materials, such as metal (e.g. steel, titanium, or stainless steel) or plastic (e.g., polycarbonate, polyethersulfone (PES), acrylonitrile-butadiene-styrene (ABS), or other injection moldable plastics). In some embodiments, an opaque plastic can be used.

The gonioscopic attachment 1302 can include a second gonioscopic optical element 1334 which, for example, can be similar to the gonioscopic optical elements 215, 220, 910, 1010, or 1110. The second gonioscopic optical element 1334 can include a distal surface 1336 (hidden from view in FIG. 13B) and a proximal surface 1338. The distal surface 1336 and the proximal surface 1338 can assume a variety of shapes (e.g., planar, spherical, aspherical, toroidal, etc.), as discussed above. In some embodiments, both the distal surface 1336 and the proximal surface 1338 are planar surfaces. In some embodiments, the proximal surface can be substantially flush with the upper surface 1340 of the housing 1318. In some embodiments, at least a portion of the proximal surface 1338 extends out past the upper surface 1340 of the housing 1318. In some embodiments, the at least a portion of the proximal surface is positioned inside the internal chamber. The second gonioscopic optical element 1334 can be made from a variety of materials, such as glass, plastic, silica or other transparent materials, as discussed above. In some embodiments, the second gonioscopic optical element 1334 can be made from a clear injection moldable plastic such as Polymethyl methacrylate (PMMA), styrene, or Zeonor. The gonioscopic optical elements 1310, 1334 may be made from the same material or from different materials. For example, in some embodiments, the first gonioscopic optical element 1310 can be made from glass while the second gonioscopic optical element can be made from plastic 1334 (or vise versa).

The distal surface 1336 of the second gonioscopic optical element 1334 can be wide enough so that the peripheral portion 1367 of the distal surface 1336 can rest on the shoulder 1330. The second gonioscopic optical element 1334 can also include a protrusion 1368 (shown in FIG. 13D) which is configured to fit into the recess 1332 to prevent the second gonioscopic optical element 1334 from rotating or becoming dislodged from the housing 1318. The gonioscopic attachment 1302 can be assembled by first positioning the second gonioscopic optical element 1334 onto the shoulder 1330 of the second piece 1322 with the protrusion 1368 disposed inside the recess 1332. Then the shoulder 1330 of the first piece 1320 can be slid under the distal surface 1336 of the second gonioscopic optical element 1334 as the first piece 1320 and the second piece 1322 are mated together.

Other configurations can be used to maintain the second gonioscopic optical element 1334 in the proper orientation inside the housing 1318. For example, the interior chamber defined by the housing 1318 and the second gonioscopic optical element 1334 can have elliptical cross-sections, preventing the second gonioscopic optical element 1334 from rotating within the interior chamber. In some embodiments, the housing can have a flange extending radially inward near the upper surface 1340 of the housing 1318, so that, when assembled, the flange extends over a portion of the proximal surface 1338 and holds the second gonioscopic optical element 1334 in place. Other configurations are possible.

In some embodiments, the housing 1318 is configured to removably attach to the handle 1306 of the gonioscope 1304. For example, the second piece 1322 can include one or more connectors 1342 configured to engage the handle 1306 at an attachment region 1344. It should be noted that in some embodiments the attachment region 1344 is not specially designed or configured to be engaged by the connectors 1342. For example, the attachment region 1344 can be merely the portion of the handle 1304 nearest the first gonioscopic optical element 1310. In some embodiments, the one or more connectors 1342 provide a snap-fit connection to the attachment region 1344 of the handle 1306. Other connection types are also possible. For example, the housing 1318 and connectors 1442 can be configured to attach the gonioscopic attachment 1302 to the first gonioscopic optical element 1310 (such as by using a screw, as discussed in more detail below), or to the mounting ring 1308, or to other portions of the gonioscope 1304.

Figure 13C:
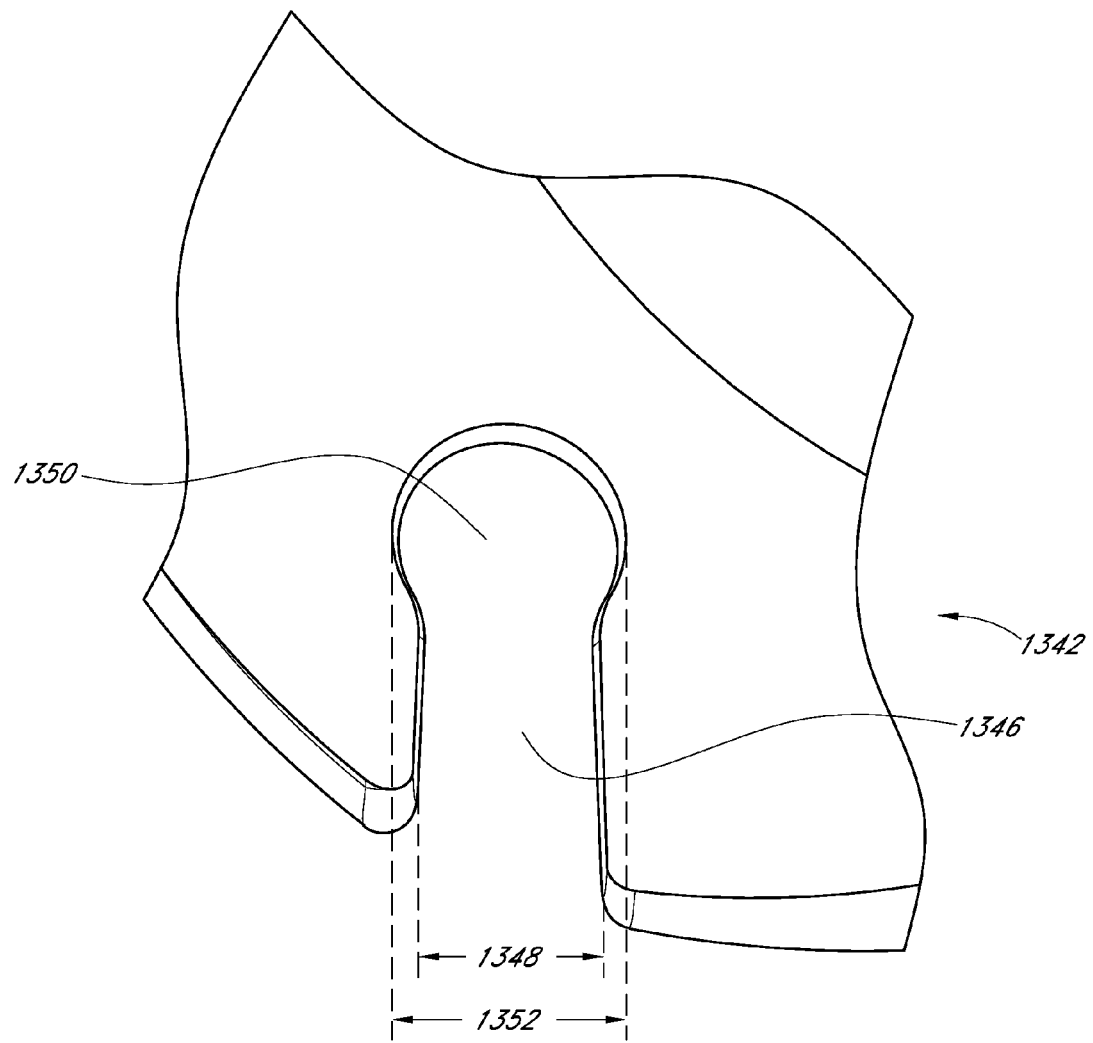
FIG. 13C shows a close up view of a connector configured to attach a gonioscopic attachment to a gonioscope.

A close-up view of a connector 1342 is shown in FIG. 13C. The connector 1342 can include a lower region 1346 having a first width 1348 and an upper region 1350 having a second width 1352. The first width 1348 can be smaller than the thickness of the attachment region 1344 of the handle 1306, and the second width 1352 can be greater than the first width 1348. Thus, when the attachment region 1344 of the handle 1306 is inserted into the lower region 1346 and slid toward the upper region 1350, the housing 1318 flexes so that the lower region 1346 widens to receive the attachment region 1344. In some embodiments, the lower region 1346 is tapered and is narrowest close to the upper region 1350, so that the housing flexes more as the attachment region 1344 slides closer to the upper region 1350. When the attachment region 1344 reaches the upper region 1350, the housing 1318 snaps back to its unflexed position securing the attachment region 1344 of the handle 1306 in the upper region 1350 of the connector 1342. In some embodiments, the upper region 1350 is shaped similarly to the cross-sectional shape of the attachment region 1344 (e.g., a circular shape as shown in FIG. 13C). In some embodiments, the second width 1352 is substantially equal to the thickness of the attachment region 1344 of the handle 1306. In some embodiments, the second width 1352 is slightly smaller than the thickness of the attachment region 1344 of the handle 1306, so that the housing 1318 remains partially flexed when the attachment region 1344 is engaged by the upper region 1350. This prevents the gonioscopic attachment 1302 from moving with respect to the gonioscope 1304 when the two are attached. In some embodiments, the upper region 1350 includes a resilient piece (not shown) formed on the inside of the upper region 1350. When engaged, the resilient piece compresses around the attachment region 1344 to prevent the gonioscopic attachment 1302 from moving with respect to the gonioscope 1304 while also allowing the housing 1318 to return to its fully unflexed position. The resilient piece can also allow the connector 1342 to securely engage handles having a range of attachment region thicknesses.

Figure 14:
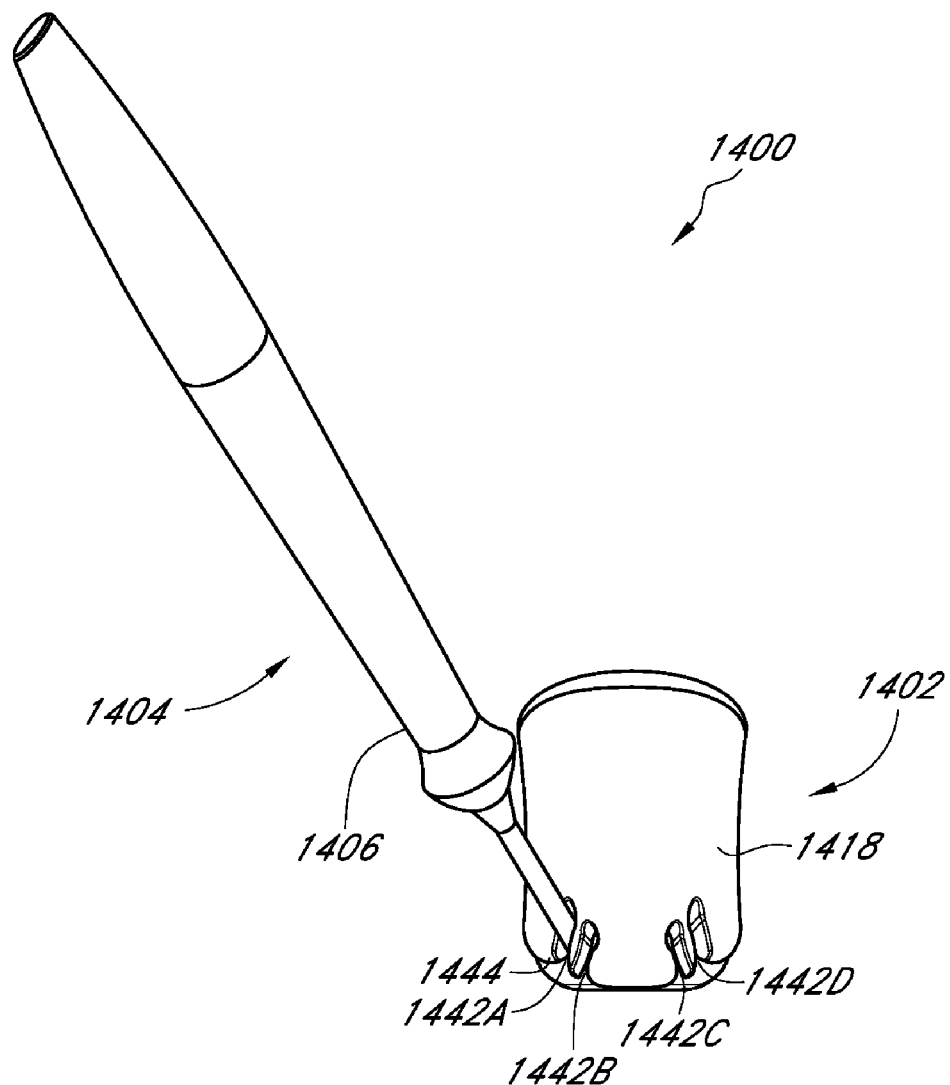
FIG. 14 schematically shows a gonioscopic optical system comprising a gonioscopic attachment having multiple connection points.

In some embodiments, the gonioscopic attachment 1302 can include a plurality of connectors 1342. For example, gonioscopic attachment 1302 may include at least one connector for attaching the gonioscopic attachment 1302 to a right-handed gonioscope and a different connector for attaching the gonioscopic attachment 1302 to a left-handed gonioscope. In some embodiments, the gonioscopic attachment 1302 can include multiple connectors that allow the gonioscopic attachment 1302 to be attached to different types of gonioscopes. Turning now to FIG. 14, a gonioscopic assembly 1400 is shown that is similar in many aspects to the gonioscopic assembly 1300. The gonioscopic attachment 1402 includes a housing 1418 that includes multiple connectors 1442A, 1442B configured to attach to the attachment region 1444 of a handle 1406 of a gonioscope 1404. In some embodiments, connectors 1442A and 1442B are configured to respectively connect to left-handed and right-handed gonioscopes. Therefore, a single gonioscopic attachment 1402 can be compatible with multiple types of gonioscopes. Thus, a single gonioscopic attachment 1402 can be configured to attach to a gonioscope in different configurations depending, for example, on the user's preference or on the surgical procedure to be performed. In some embodiments, the gonioscopic attachment 1402 can include one or more stress relief cutouts 1443A, 1443B to facilitate attachment of the gonioscopic attachment 1402 to the gonioscope 1404.

Returning now to FIGS. 13A and 13B, the housing 1318 can have an upper area 1354 configured to engage the second gonioscopic optical element 1334 (as discussed above) and a lower area 1356 configured to slidably receive at least a portion of the first gonioscopic optical element 1310 into the recess formed below the second gonioscopic optical element 1334. In some embodiments, the recess has a height measured from the lowest portion of the housing 1318 to the distal surface of the second gonioscopic optical element 1334 of greater than about 0 mm and/or less than about 10 mm. In some embodiments a portion of the first gonioscopic optical element extends out of the bottom of the housing 1318 (as shown in FIG. 13A). The lower area 1356 can include an outwardly sloping portion 1358 configured to receive the tapered mounting ring 1308.

Figure 13D:
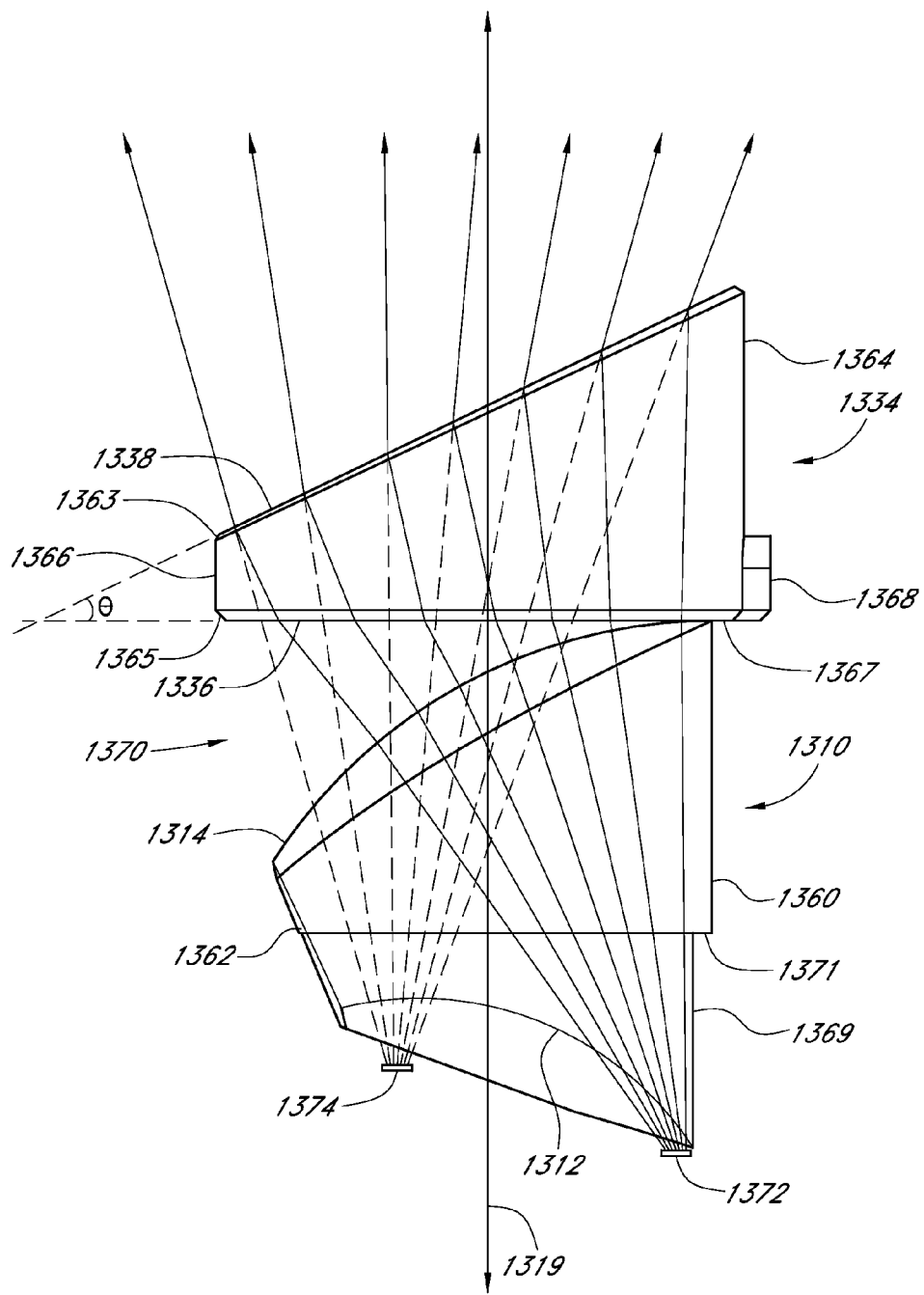
FIG. 13D schematically shows a gonioscopic optical system comprising two gonioscopic optical elements.

Turning now to FIG. 13D, the first gonioscopic optical element 1310 and the second gonioscopic optical element 1334 are shown in one possible configuration. In some embodiments, both the first gonioscopic optical element 1310 and the second gonioscopic optical element 1334 can be substantially wedge-shaped. The first gonioscopic optical element 1310 can include a thick end 1360 and a narrow end 1362. Similarly, the second gonioscopic optical element can include a thick end 1364 and a narrow end 1366. In some embodiments, both of the thick ends 1360, 1364 can be positioned closer to one side of the gonioscope (e.g., closer to the handle), or closer to the object being imaged, than the respective narrow ends 1362, 1366. For example, both of the thick ends 1360, 1364 can be positioned against the second piece 1322 of the housing 1318, and both of the narrow ends 1362, 1366 can be positioned against the first piece 1320 of the housing 1318. In some embodiments, the thick end 1364 of the second gonioscopic optical element 1334 can be positioned substantially above the thick end 1360 of the first gonioscopic optical element 1310, and the thin end 1366 of the second gonioscopic optical element can be positioned substantially above the thin end 1362 of the first gonioscopic optical element 1310. In some embodiments, a line drawn from the thick end 1360 to the thin end 1362 of the first gonioscopic optical element 1310 points in substantially the same direction as a line drawn from the thick end 1364 to the thin end 1366 of the second gonioscopic optical element 1334, having an angle of deviation therefrom of no more than 20°, 15°, 10°, 5°, 2°, or 1°.

In some embodiments, a portion of the second gonioscopic optical element 1334 extends radially past the first gonioscopic optical element 1310 creating a peripheral portion 1367 configured to engage the shoulder 1330. The second gonioscopic optical element 1334 can also include a protrusion 1368 configured to fit into the recess 1332 to secure the second gonioscopic optical element in the housing (as discussed above). The first gonioscopic optical element 1310 can include a narrow region 1369 defining a ridge 1371. The narrow regions 1369 and ridge 1371 can be configured to mate with the mounting ring 1308 to connect the first gonioscopic optical element 1310 to the handle 1306.

In some embodiments, the distal surface 1336 of the second gonioscopic optical element 1334 can be planar and can be substantially perpendicular to the longitudinal axis 1319 of the housing 1318, while the proximal surface 1338 of the second gonioscopic optical element 1334 can also be planar but not perpendicular to the longitudinal axis 1319 of the housing 1318. The second gonioscopic optical element 1334 can be wedge shaped, and the proximal surface 1338 can have an angle of deviation θ with respect to the distal surface 1336. The angle of deviation θ can be greater than about 0° and/or less than about 60°. In some embodiments, the second gonioscopic optical element 1334 can include beveled or angled edges 1363 and 1365 around the peripheries of the proximal surface 1338 and the distal surface 1336 respectively. Various other configurations are possible. For example, the proximal surface 1338 and the distal surface 1336 of the second gonioscopic optical element 1334 can be spherical, aspherical, toroidal, etc., as discussed above. In some embodiments, the distal surface 1336 of the second gonioscopic optical elements 1334 can be angled, and in some embodiments, both the distal surface 1336 and the proximal surface 1338 can be angled, so that the second gonioscopic optical element 1334 is a double angled prism. For example, in some embodiments, both the distal surface 1336 and the proximal surface 1338 are not perpendicular to the optical axis of the eye and/or not perpendicular to the longitudinal axis of the housing.

When the gonioscopic attachment 1302 is attached to the gonioscope 1304, the first gonioscopic optical element 1310 can be slidably inserted into the recess formed below the second gonioscopic optical element 1334 until a portion of the proximal surface 1314 of the first gonioscopic optical element 1310 contacts a portion of the distal surface 1336 of the second gonioscopic optical element 1334. In some embodiments, the gonioscopic attachment 1302 can be configured to receive the first gonioscopic optical element 1310 without it contacting the second gonioscopic optical element 1334. In some embodiments, at least a portion of the proximal surface 1314 of the first gonioscopic optical element 1310 used to create the image is space apart from the distal surface 1336 of the second gonioscopic optical element 1334, such that a space (e.g., an air gap) 1370 is disposed therebetween. In some embodiments, the space 1370 between the first and second gonioscopic optical elements 1310, 1334 is greater than about 0 mm and/or no more than about 10 mm. The gonioscopic optical elements 1310, 1334 preferably are positioned so that the space 1370 is relatively small so as to create a compact tool. But the space 1370 can be large enough so that light propagating from the first gonioscopic optical element 1310 to the second gonioscopic optical element 1334 refracts a first time as it transitions from the first gonioscopic optical element 1310 to the space 1370, and so that the light refracts a second time as it transitions from the space 1370 to the second gonioscopic optical element 1334. For example, the space 1370 can be at least about 0.1 mm wide (e.g., about 0.5 mm wide or about 1.0 mm wide). In some embodiments, the width of the space 1370 can vary such that the proximal surface 114 of the first gonioscopic optical element 1310 can be closer to the second gonioscopic optical element 1334 at a one end than at the opposite end (as can be seen in FIG. 13D). In some embodiments, no additional optical elements (e.g., no additional lenses or prisms) are disposed in the space 1370 between the first and second gonioscopic optical elements 1310, 1334. In some embodiments the space 1370 includes a medium that has an index of refraction that is lower than one or both of the gonioscopic optical elements 1340, 1334. For example, the space can be filled with air or can include an optical element made from a low index material. In some embodiments, air can be used to provide an interface with the first gonioscopic optical element and/or the second gonioscopic optical element that has a large index contrast (e.g., air/plastic or air/glass) to refract light. For example, the gonioscopic optical elements 1310, 1334 can be made from plastic or glass having an index of refraction of at least about 1.4 and/or no more than about 2.5.

When assembled, the first gonioscopic optical element 1310 can be positioned so that light emitted by its proximal surface 1314 is directed toward the second gonioscopic optical element 1334, and the second gonioscopic optical element 1334 can be configured to redirect the light. In some embodiments, the second gonioscopic optical element 1334 redirects the light to form an image viewable with a surgical microscope position that is positioned substantially directly above the patient's eye without tilting the patient's head, as shown, for example, in FIG. 12. In some embodiments, the second gonioscopic optical element is configured to bend the light by refraction at both its distal surface 1336 and proximal surface 1338. The second gonioscopic optical element 1334 can be configured to bend the light emitted by the first gonioscopic optical element 1310 between 12° and 20°, and more specifically between 14° and 16°. Configurations that bend the light by other amounts are also possible. For example, by changing the index of refraction of the second gonioscopic optical element 1334 or the angle of deviation θ, the amount that the light is bent can be adjusted.

FIG. 13D shows a schematic ray trace of one possible configuration. The distal surface 1312 of the first gonioscopic optical element is placed on the patient's eye (not shown) and light from an object at an object plane 1372 inside the patient's eye is transmitted from the eye and into the transparent material of the first gonioscopic optical element 1310. During use, various materials can be used between the distal surface 1312 of the first gonioscope optical element 1310 and the patient's eye to reduce reflection of light as it passes from the patient's eye to the first gonioscope optical element 1310. In some embodiments, an index matching fluid (e.g., a viscoelastic gel) and/or index matching film may be used between the cornea and the surface of the first gonioscope optical element. The light passes through the proximal surface 1314 of the first gonioscopic optical element 1310 and into the air gap 1370. In some embodiments, the light can be refracted at the transition from the first gonioscopic optical element 1310 to the air gap 1370. The light emitted from the proximal surface 1314 of the first gonioscopic optical element 1310 is received by the distal surface 1336 of the second gonioscopic optical element 1334, and the light can be refracted at the transition from the air gap 1370 to the transparent material of the second gonioscopic optical element 1334. The light can again be refracted as it exits the second gonioscopic optical element 1334 through its proximal surface 1338. The light emitted by the second gonioscopic optical element 1334 can form an image at an image plane 1374. The image can be a virtual and uninverted (i.e., upright) image, as discussed above. As shown in FIG. 13D, in some embodiments, the gonioscopic optical elements 1310, 1334 do not focus the light emitted from the object. Rather, the light emitted by the second gonioscopic optical element 1334 diverges.

In some embodiments, the object at the object plane 1372 is disposed laterally in a first direction with respect to the longitudinal axis 1319 of the housing 1318 (or the centerline through the housing 1318), and the image at the image plane 1374 is disposed laterally in a second direction with respect to the longitudinal axis 1319 of the housing 1318 (or the centerline through the housing 1318), wherein the second direction is opposite the first direction. Thus, the object plane 1372 and the image plane 1374 can be disposed on opposite sides of the longitudinal axis 1319 of the housing 1318 (or the centerline through the housing 1318). In some embodiments, the object plane 1372 can be disposed laterally in a first direction with respect to the centerline through the first gonioscopic optical element 1310, and the image plane 1374 can be disposed laterally in a second direction with respect to the centerline through the first gonioscopic optical element 1310, wherein the second direction is opposite the first direction. Thus, the object plane 1372 and the image plane 1374 can be disposed on opposite sides of the centerline through the first gonioscopic optical element 1310. In some embodiments, the object plane 1372 can be disposed laterally in a first direction with respect to the centroid of the first gonioscopic optical element 1310, and the image plane 1374 can be disposed laterally in a second direction with respect to the centroid of the first gonioscopic optical element 1310, wherein the second direction is opposite the first direction. Thus, the object plane 1372 and the image plane 1374 can be disposed on opposite sides of the centroid of the first gonioscopic optical element 1310. In some embodiments, the object plane 1372 can be disposed laterally in a first direction with respect to the optical axis of the eye, and the image plane 1374 can be disposed laterally in a second direction with respect to the optical axis of the eye, wherein the second direction is opposite the first direction. Thus, the object plane 1372 and the image plane 1374 can be disposed on opposite sides of the optical axis of the eye. In some embodiments, the object is closer to the thick end 1360 of the first gonioscopic optical element 1310 than to the narrow end 1362, and the image is closer to the narrow side 1362 of the first gonioscopic optical element 1310 than the object. Thus, the object can be closer to the thick end 1360 than the image, and the image can be closer to the narrow end 1362 than the object.

In some embodiments, at least a portion of the light forming the image is transmitted through the second gonioscopic optical element 1334 without relying on internal reflection for image formation. At least a portion of the light can be transmitted from the distal surface 1336 to the proximal surface 1338 without striking any side surfaces of the second gonioscopic optical element 1334, and contribute to formation of the image. Likewise, the first gonioscopic optical element 1310 can also be configured to transmit light from its distal surface 1312 to its proximal surface 1314 without relying on internal reflection for image formation. In some embodiments, at least a portion of the interior surface of the housing 1318 is configured to reduce reflection of light that strikes the side surfaces of the gonioscopic optical elements 1310, 1334. For example, at least a portion of the interior surface can be made a textured material (e.g., matt) or a dark material (e.g., gray or black). In some embodiments, an absorptive material can be coated onto at least a portion of the interior surface.

The gonioscopic optical elements 1310, 1334 can assume various other shapes and sizes and can be arranged in various other configurations, such as those discussed above in connection with FIGS. 2-4 and 8-11. In some embodiments, the gonioscopic attachment 1302 can include multiple optical elements (such as multiple wedge-shaped prisms) for redirecting light. Many other variations are possible.

In some embodiments, the gonioscopic attachment 1302 is made from light weight materials (e.g., plastic). Because the user holds the gonioscope into contact with the patient's eye during use, adding significant weight to the gonioscope can be undesirable. In some embodiments, the gonioscopic attachment 1302 weighs at least about 1 gram and/or no more than about 10 grams.

In some embodiments, the gonioscopic attachment 1302 can be made from economic materials (as discussed above) and can be a disposable, single-use unit. In some embodiments, the gonioscopic attachment 1302 can be made from all plastic materials. The gonioscopic attachment 1302 may be pre-sterilized (e.g., gamma sterilized) and furnished in a sealed package (e.g., a blister pack). The gonioscopic attachment 1302 can be packaged with other tools, such as a stent, an aqueous shunt, and/or an applicator for inserting a device into the trabecular meshwork for treating glaucoma, etc. The gonioscopic attachment 1302 can be removed from its packaging before surgery and attached to a conventional gonioscope such as the Ocular Instruments Trabecular Bypass Gonioprism. Because the gonioscopic attachment 1302 can be configured to attach to a conventional gonioscope, a medical practitioner can use it in conjunction with a gonioscope he/she already owns and is accustomed to using. The gonioscopic attachment 1302 allows the surgery to be performed without tilting the patient's head, as would be required if the conventional gonioscope were used without the gonioscopic attachment 1302. After the surgery, the gonioscopic attachment 1302 can be removed from the gonioscope and discarded.

In some embodiments, the gonioscopic attachment 1302 can attach to a disposable, single-use gonioscope that can be discarded after use. For example, the gonioscope can be made from low cost, light weight materials such as the plastics discussed herein. In some embodiments, the gonioscope is reusable and can be sterilized after use. In some embodiments, the gonioscopic attachment 1302 can be reusable. For example, the gonioscopic attachment 1302 can be made from autoclavable metal and glass materials and be sterilized along with the gonioscope after surgery. Other variations are possible.

Figure 15:
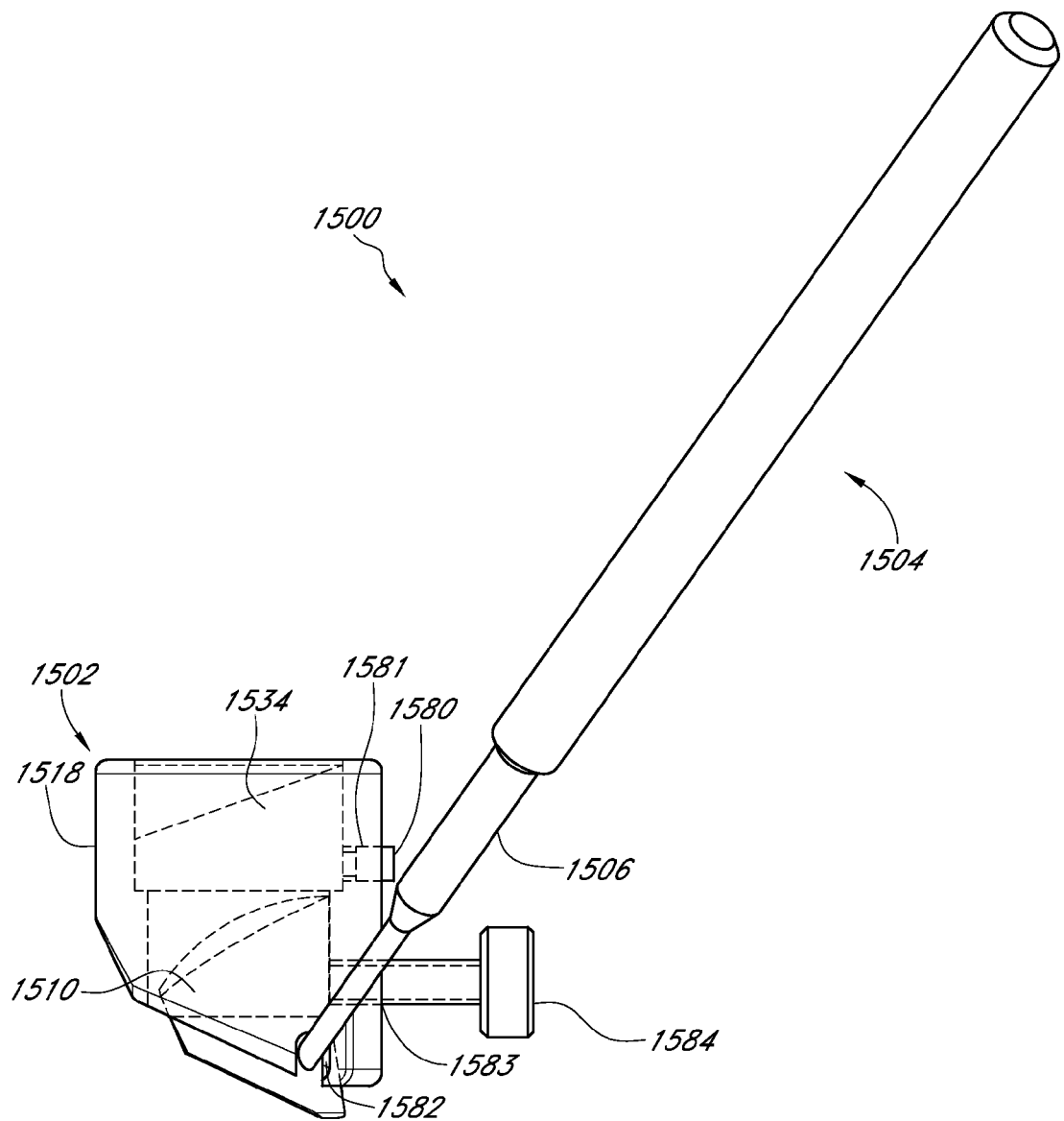
FIG. 15 schematically shows a gonioscopic optical system comprising a gonioscopic attachment that is compatible with multiple types of gonioscopes and/or gonioscopic optical elements.

Turning now to FIG. 15, a gonioscopic assembly 1500 is disclosed that is similar in some regards to the gonioscopic assembly 1300. The gonioscopic attachment 1502 can include a releasable securing mechanism for securing the second gonioscopic optical element 1534 to the housing 1518. The releasable securing mechanism 1580 can be, for example, a first screw 1580 (e.g., a nylon tipped metal screw) disposed in a first threaded bore 1581 in the housing 1518. The second gonioscopic optical element 1534 can be slidably inserted into the housing 1518, and the first screw 1580 can be tightened until it presses against the second gonioscopic optical element 1534 and frictionally holds it in place against the housing 1518. In some embodiments, the second gonioscopic optical element 1534 can include a bore (not shown) to receive the first screw to further secure the second gonioscopic optical element 1534. Other approaches can also be used to secure the second gonioscopic optical element 1534 to the housing 1518. In this embodiment, the second gonioscopic optical element 1534 can be interchangeable with other optical elements that, for example, turn the light by different amounts. Thus, different optical elements can for example be used to make the gonioscopic attachment 1502 compatible with multiple types of gonioscopes or be used for different procedures.

In some embodiments, the gonioscopic attachment 1502 can be configured to connect to multiple types of gonioscopes. The housing 1518 can include a cutout 1582 to receive the handle 1506 of a gonioscope 1504. The cutout 1582 can be wide enough to receive a variety of handle sizes. Thus, in this embodiment, the cutout 1582 does not provide a snap-fit to secure the housing 1518 to the handle 1506. The gonioscopic attachment 1502 can include a second screw 1584 disposed in a second threaded bore 1583 for securing the housing to the gonioscope 1504. The gonioscopic attachment 1502 can slidably receive at least a portion of the first gonioscopic optical element 1510 of the gonioscope 1504 into the recess defined below the second gonioscopic optical element 1534. The screw 1584 can be tightened against the first gonioscopic optical element 1510, securing the housing 1518 to the gonioscope 1504. In some embodiments, the second screw 1584 can press the first gonioscopic optical element 1510 against the inner surface of the housing 1518. In some embodiments, the screw 1582 can cause the handle 1506 to press against the side of the cutout 1582 to secure the housing 1518 to the gonioscope 1504. Other approaches can also be used to secure the first gonioscopic optical element 1510 to the housing 1518.

In some embodiments, the gonioscopic attachment 1502 can be a disposable, single-use attachment and can be made from an inexpensive material (e.g., plastic). In some embodiments, at least part of the gonioscopic attachment 1502 can be configured to be reusable. For example, the housing can be made from a metal (e.g., steel, titanium, or stainless steel) or other sterilizable (e.g., autoclavable) material. Likewise, the second gonioscopic optical element 1534 can be made from a sterilizable material (e.g., glass). In some embodiments, the housing can be reusable, but the second gonioscopic optical element 1534 can be a disposable single-use piece and can be made from an inexpensive material (e.g., plastic).

Figure 16:
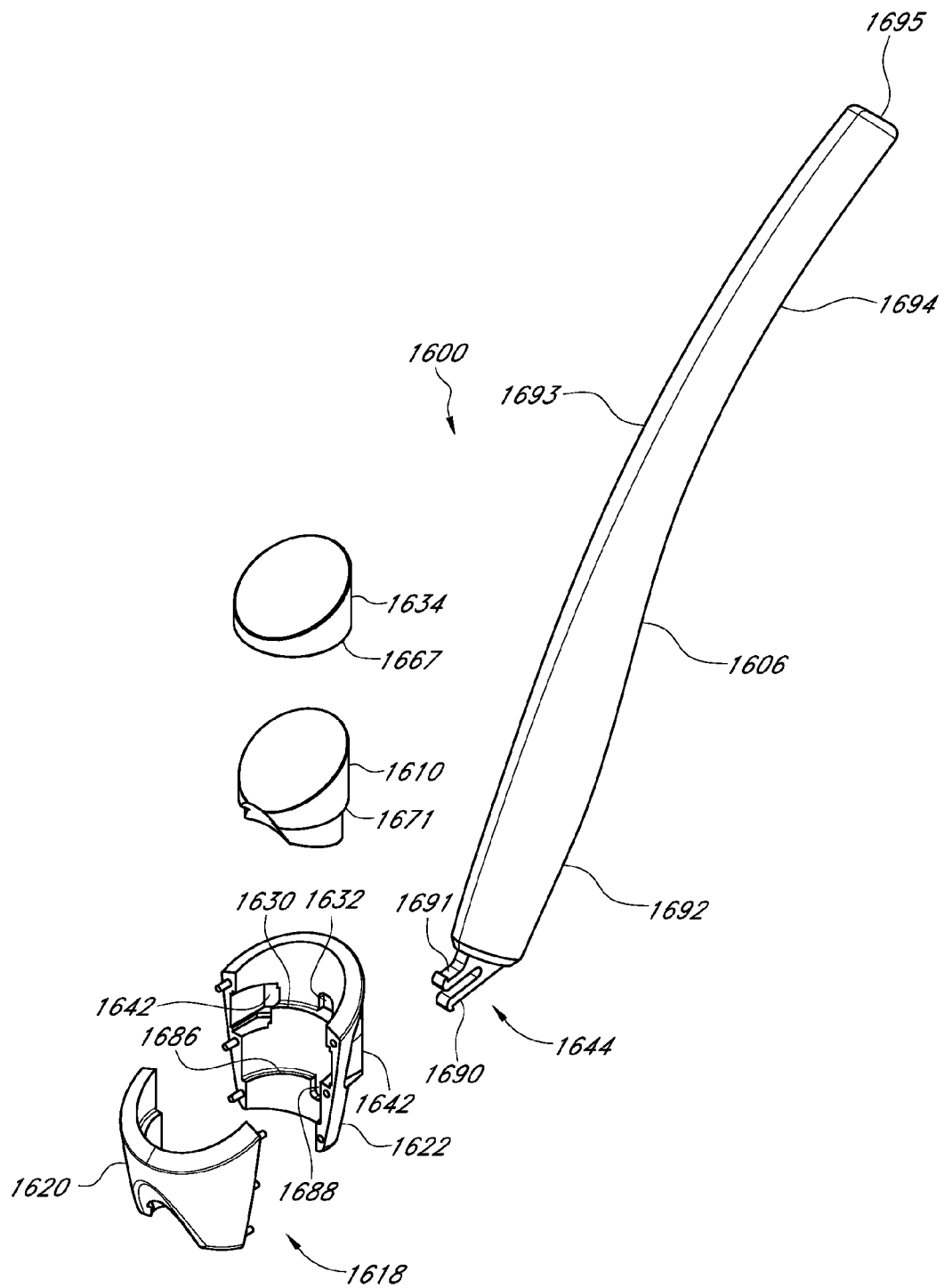
FIG. 16 schematically shows a gonioscopic optical system comprising two gonioscopic optical elements secured by a housing and an ergonomic handle.

FIG. 16 shows an embodiment of a gonioscope 1600 that includes both the first gonioscopic optical element 1610 and the second gonioscopic optical element 1634 in an integrated unit. The gonioscope 1600 can include a housing 1618, which can comprise a first piece 1620 and a second piece 1622. The housing 1618 can be made from a variety of materials, such as metal (e.g. steel, titanium, or stainless steel) or plastic (e.g., polycarbonate, polyethersulfone (PES), acrylonitrile-butadiene-styrene (ABS), or other injection moldable plastics). In some embodiments, a low cost injection moldable plastic is used. In some embodiments, the housing can be made from a textured material (e.g., matt) or dark material to reduce reflections.

The second gonioscopic optical element 1634 can be secured in the housing 1618 with its peripheral portion 1667 in contact with the shoulder 1630, and a protrusion (hidden from view) fitted into the notch 1632. The first gonioscopic optical element 1610 can also be secured in the housing 1618 with the ridge 1671 in contact with the shoulder 1686, and a protrusion (hidden from view) fitted into the notch 1688. In some embodiments, the first and second gonioscopic optical elements 1610, 1634 can be configured similar to the first and second gonioscopic optical elements 1310, 1334 as shown in FIG. 13D. In some embodiments, the first and second gonioscopic optical elements 1610, 1634 can be conjoined or integrally formed (e.g., as a single injection molded piece). For example, the gonioscopic optical elements 1610, 1634 can be conjoined or connected at an edge with the distal surface of the second gonioscopic optical element 1634 spaced apart from the proximal surface of the first gonioscopic optical element 1610. In some embodiments, the gonioscopic optical elements 1610, 1634 can be arranged similarly to the gonioscopic optical elements 1310, 1334 described above with regard to, for example, FIG. 13D.

The gonioscopic optical elements 1610, 1634 can be made from a variety of materials, such as glass, plastic, silica or other transparent materials as discussed above. In some embodiments, the gonioscopic optical elements 1610, 1634 can be made from a clear injection moldable plastic such as Polymethyl methacrylate (PMMA), styrene, or Zeonor. The gonioscopic optical elements 1610, 1634 may be made from the same material or from different materials. For example, in some embodiments, the first gonioscopic optical element 1610 can be made from glass while the second gonioscopic optical element can be made from plastic 1634 (or vise versa).

The housing 1618 can include one or more connectors 1642 configured to connect to the handle 1606. In some embodiments, the connectors 1642 can be slits or indentations in the housing 1618 configured to mate with an attachment region 1644 of the handle 1606. In some embodiments, the attachment region 1644 can include a lower barbed prong 1690 and an upper barbed prong 1691. The attachment region 1644 can be slidably inserted into the connector 1642, causing the prongs 1690, 1691 to bend toward one another. Once the barbed ends of the prongs 1690, 1691 reach the corresponding notches (not shown) of the connector 1642, the prongs 1690, 1691 snap back to their unflexed positions and the barbs engage the corresponding notches, securing the handle 1606 to the housing 1618. Other mechanisms for connecting the handle 1606 to the housing 1618 can be used.

In some embodiments, the handle 1606 is removably attachable to the housing 1618. The housing 1618 can include multiple connectors 1642 that allow the handle 1606 to be attached in different configurations. For example, the housing 1618 can include a first connector for connecting the handle 1606 in a right-handed configuration, and a second connector for connecting the handle 1606 in a left-handed configuration. In some embodiments, the handle 1606 can come preattached to the housing 1618 in a predetermined configuration. In some embodiments, the handle 1606 can come separate from the housing 1618, and the user can choose whether to connect the handle 1606 in a right-handed or left-handed configuration. In some embodiments, the handle 1606 can be attached to the housing 1618 so that it can be toggled between right-handed and left-handed configurations. For example, the gonioscope may include a hinge or swivel that allows the handle to move and a securing mechanism that can be used to lock the handle in a desired position.

The handle 1606 can be made from a variety of materials, such as metal (e.g. steel, titanium, or stainless steel) or plastic (e.g., polycarbonate, polyethersulfone (PES), acrylonitrile-butadiene-styrene (ABS), or other injection moldable plastics). In some embodiments, a low cost injection moldable plastic is used. In some embodiments, the handle can be made from a textured (e.g., matt) or dark material.

The handle 1606 can be ergonomically designed. For example, the handle 1606 can be configured to fit the shape of the user's hand. For example, the top surface 1693 of the handle 1606 can have a radius of curvature of at least about 200 mm and/or no more than about 400 mm so as to fit the curvature of the user's index finger. The handle 1606 can include a thick portion 1692 and a thin portion 1694. In some embodiments, the top surface 1693 can be more curved near the thin portion 1694 than near the thick portion 1692. In some embodiments, the thin portion 1694 can be configured to rest on the user's hand between the index finger and thumb and have a thickness of at least about 6 mm and/or no more than about 15 mm. In some embodiments the handle 1606 can include counterweight 1695 at the end of the handle to counterbalance the weight of the housing 1618 and the gonioscopic optical elements 1610, 1634. In some embodiments, the handle does not include a counterweight, so as to reduce the overall weight of the gonioscope 1600. The surface of the handle 1606 can be generally smooth (as shown) or it can include grooves on its top side and/or its bottom side to provide a better gripping surface for the user of the gonioscope.

The gonioscope 1600 can be made from low cost materials (as discussed above) and can be a disposable, single-use tool. The gonioscope 1600 can be pre-sterilized (e.g., gamma sterilized) and furnished in a sealed package (e.g., a blister pack). The gonioscope 1600 can be removed from its packaging before surgery and discarded after used. The handle 1606 can be pre-attached or packaged separately. Similarly, other gonioscope designs disclosed herein can be incorporated into a low cost, disposable, single-use gonioscope. Because a new pre-sterilized gonioscope can be used for each surgical procedure, no sterilization of the gonioscope is performed by the user prior to use. Sterilization methods such as autoclave, ethylene oxide, or soaking in glutaraldehyde can be messy and time consuming. In some embodiments, a pre-sterilized disposable gonioscope can be kitted with surgical tools to create procedure trays. For example, disposable gonioscopes can be packaged with a stent, aqueous shunt, and/or applicators for inserting a device into the trabecular meshwork for treatment of glaucoma.

In some embodiments, the gonioscope 1600 can be made from light weight materials (e.g., plastic). Because the user holds the gonioscope 1600 into contact with the patient's eye during use, a light weight gonioscope can be desirable to reduce the effort required to operate the gonioscope. In some embodiments, the gonioscope 1600 weighs at least about 5 grams and/or no more than about 25 grams.

Figure 17B:
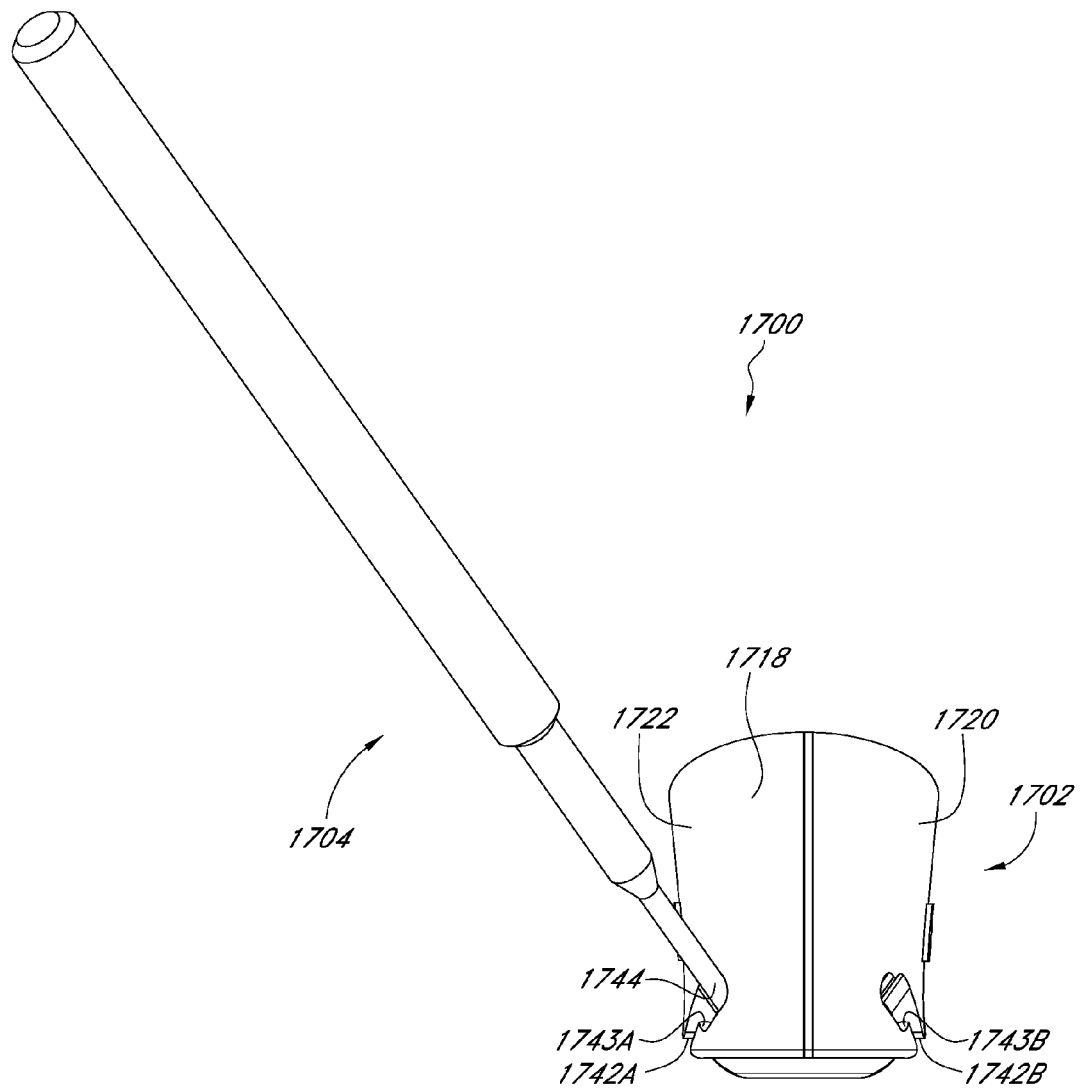
Figure 17C:
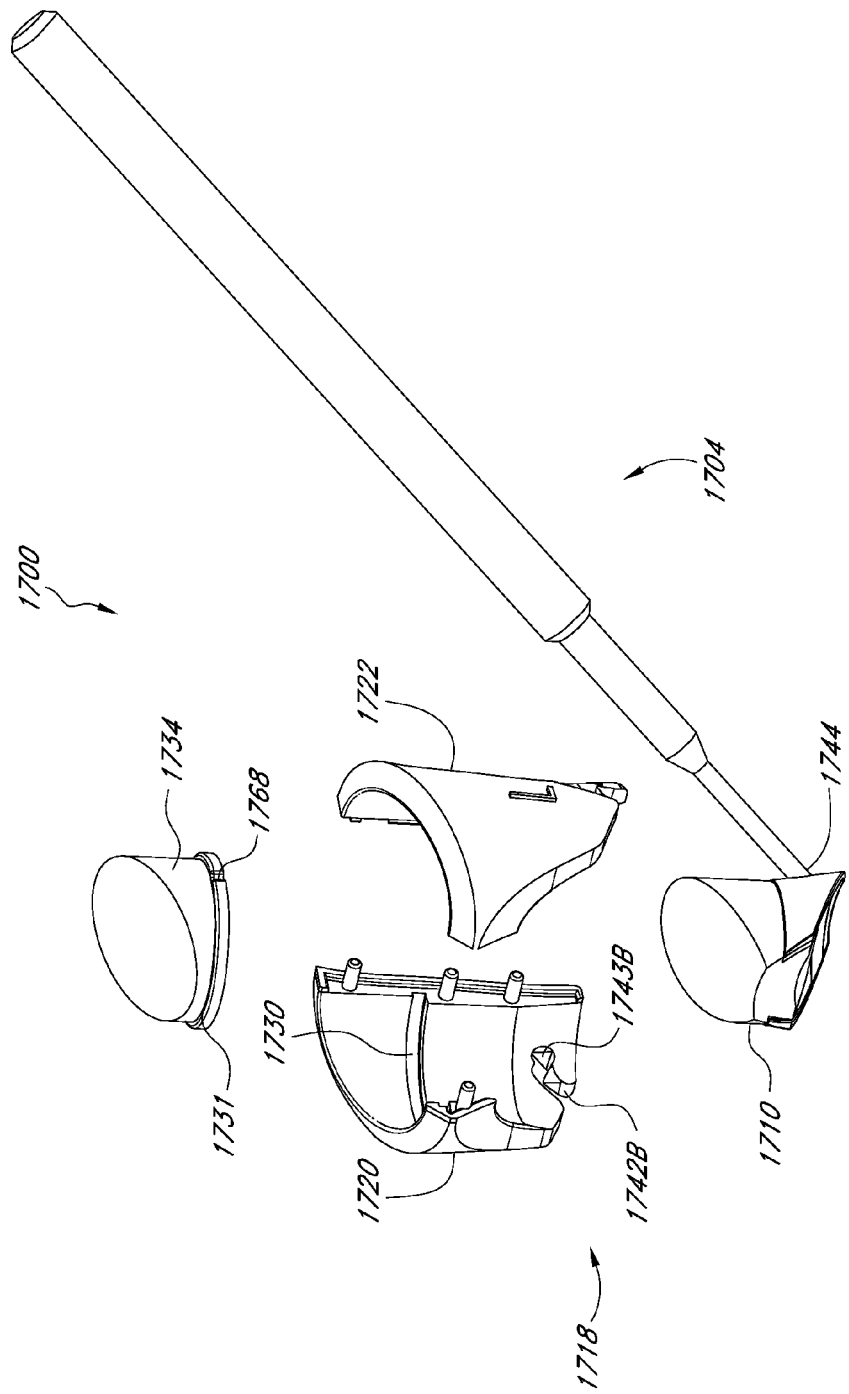
Figure 17D:
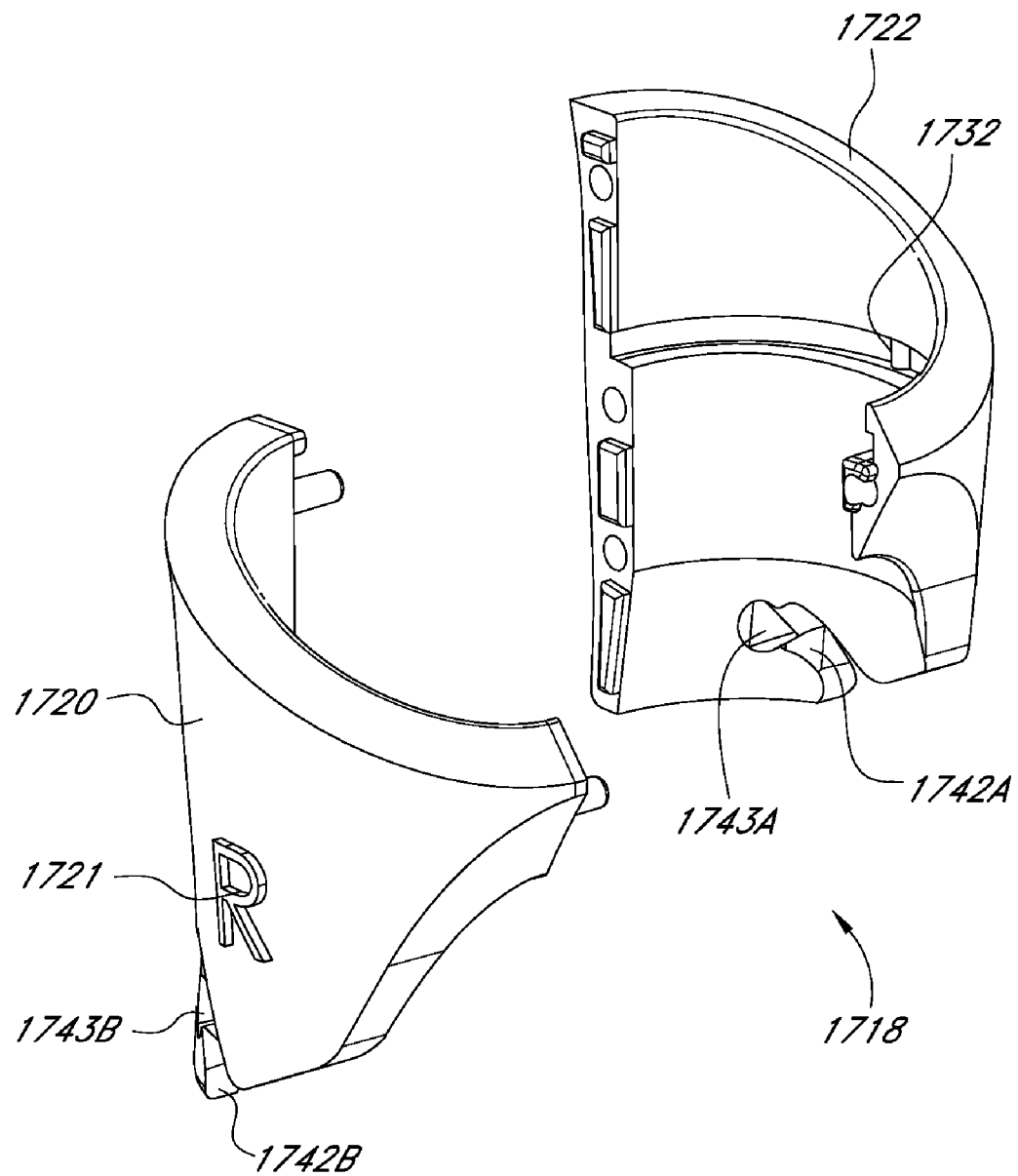
Figure 17E:
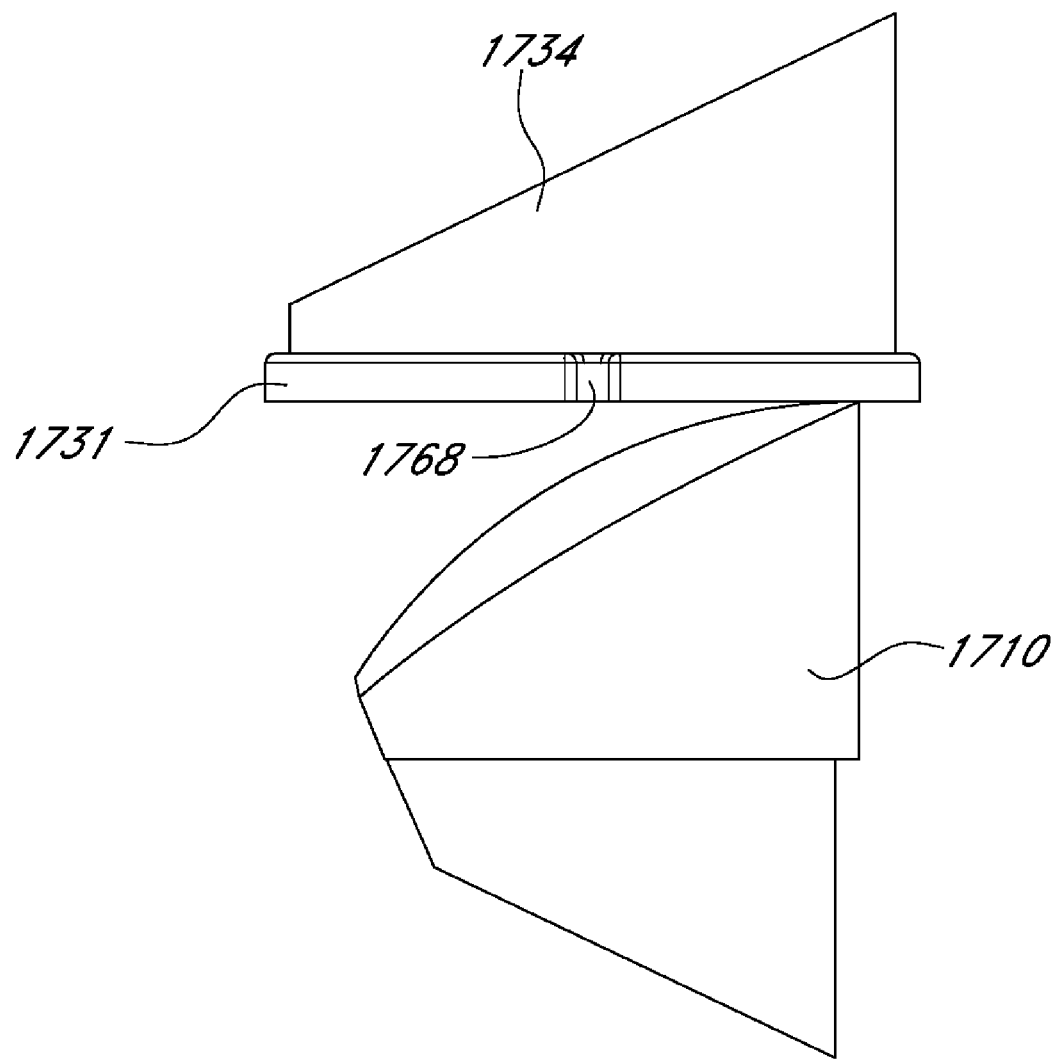

A variety of other designs are possible. For example, FIGS. 17A-17B show an embodiment of a gonioscopic assembly 1700 that includes a gonioscopic attachment 1702 attached to a gonioscope 1704. FIG. 17C is an exploded perspective view of the gonioscopic assembly 1700. FIG. 17D is an exploded perspective view of the housing 1718. FIG. 17E is a side view of the first and second gonioscopic optical elements 1710, 1734 of the gonioscopic assembly 1700. Many aspects of the gonioscope 1704 and the gonioscopic attachment 1702 can be similar to the gonioscope 1304 and the gonioscopic attachment 1302 (or other embodiments) discussed above, some of the disclosure of which can also be applied to the gonioscope 1704 and gonioscopic attachment 1702, but may include differences such as those identified below.

The gonioscopic attachment 1702 can include a housing 1718, that can be a two-part assembly having a right side piece 1720 and a left side piece 1722. The right side piece 1720 can include a right side label 1721, which can be, for example, the letter R. Similarly, the left side piece 1722 can include a left side label 1723, which can be, for example, the letter L. The labels 1721, 1723 can be used to indicate to the user which side of the gonioscopic attachment 1702 is compatible with a right-handed gonioscope and which side is compatible with a left-handed gonioscope. The gonioscopic attachment 1702 can include two connectors 1742A, 1742B configured to attached to an attachment region 1744 of the gonioscope 1704. In some embodiments, the connectors 1742A, 1742B can be cutouts each having a step 1743A, 1743B that facilitates the securing of the gonioscopic attachment 1702 to the gonioscope 1704. For example, as the attachment region 1744 of the gonioscope 1704 is pressed into one of the connectors 1742A, 1742B the corresponding step 1743A or 1743B can interfere slightly, causing the attachment region 1744 to snap into a retained position.

The gonioscopic attachment 1702 includes a second gonioscopic optical element 1734 secured within the housing 1718. The inner surface of the housing 1718 can include an annular ridge 1730, and the second gonioscopic optical element 1734 can include an annular ring 1731 configured to fit into the annular ridge 1730. When assembled, the top surface of the annular ridge 1730 can prevent the second gonioscopic optical element 1734 from moving longitudinally toward the top of the gonioscopic attachment 1702, and the bottom surface of the annular ridge 1730 can prevent the second gonioscopic optical element 1734 from moving longitudinally toward the bottom of the gonioscopic attachment 1702. The annular ridge 1730 can include a protrusion 1732 (shown in FIG. 17D) that is configured to insert into a notch 1768 in the annular ring 1731 to prevent the second gonioscopic optical element 1734 from rotating within the housing 1718.

When the gonioscopic attachment 1702 is attached to the gonioscope 1704, the first gonioscopic optical element 1710 can be received into the recess formed inside the housing 1718 below the second gonioscopic optical element 1734. During use, the first and second gonioscopic optical elements 1710, 1734 can be positioned as shown in FIG. 17E. The first and second gonioscopic optical elements 1710, 1734 can have optical properties that are similar to those of the first and second gonioscopic optical elements 1310, 1334 discussed above, and can be used to form an upright virtual image in a manner similar to the ray trace shown in FIG. 13D. Various configurations other than those shown in FIG. 17E are also possible. For example, in some embodiments, the proximal surface of the first gonioscopic optical element 1710 can be flat, or can have a variety of other shapes, as discussed above.

Figure 18A:
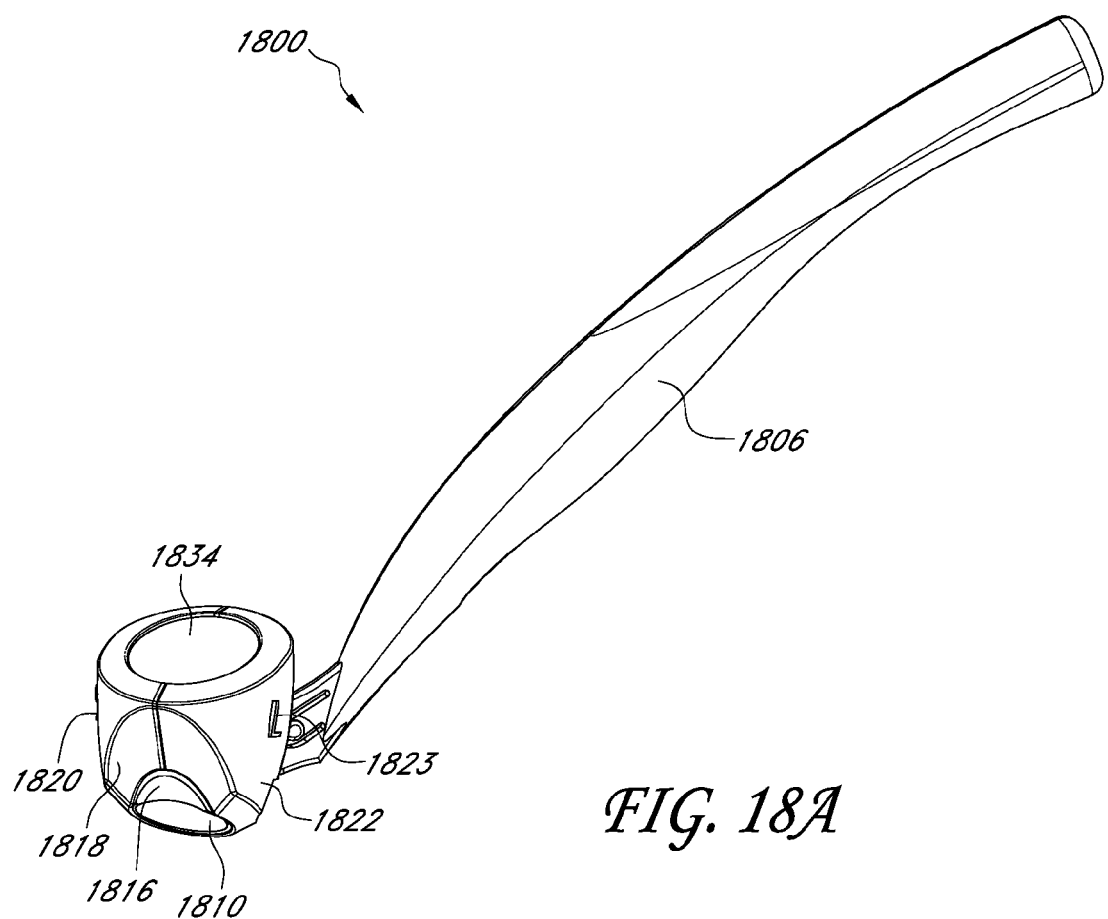
Figure 18C:
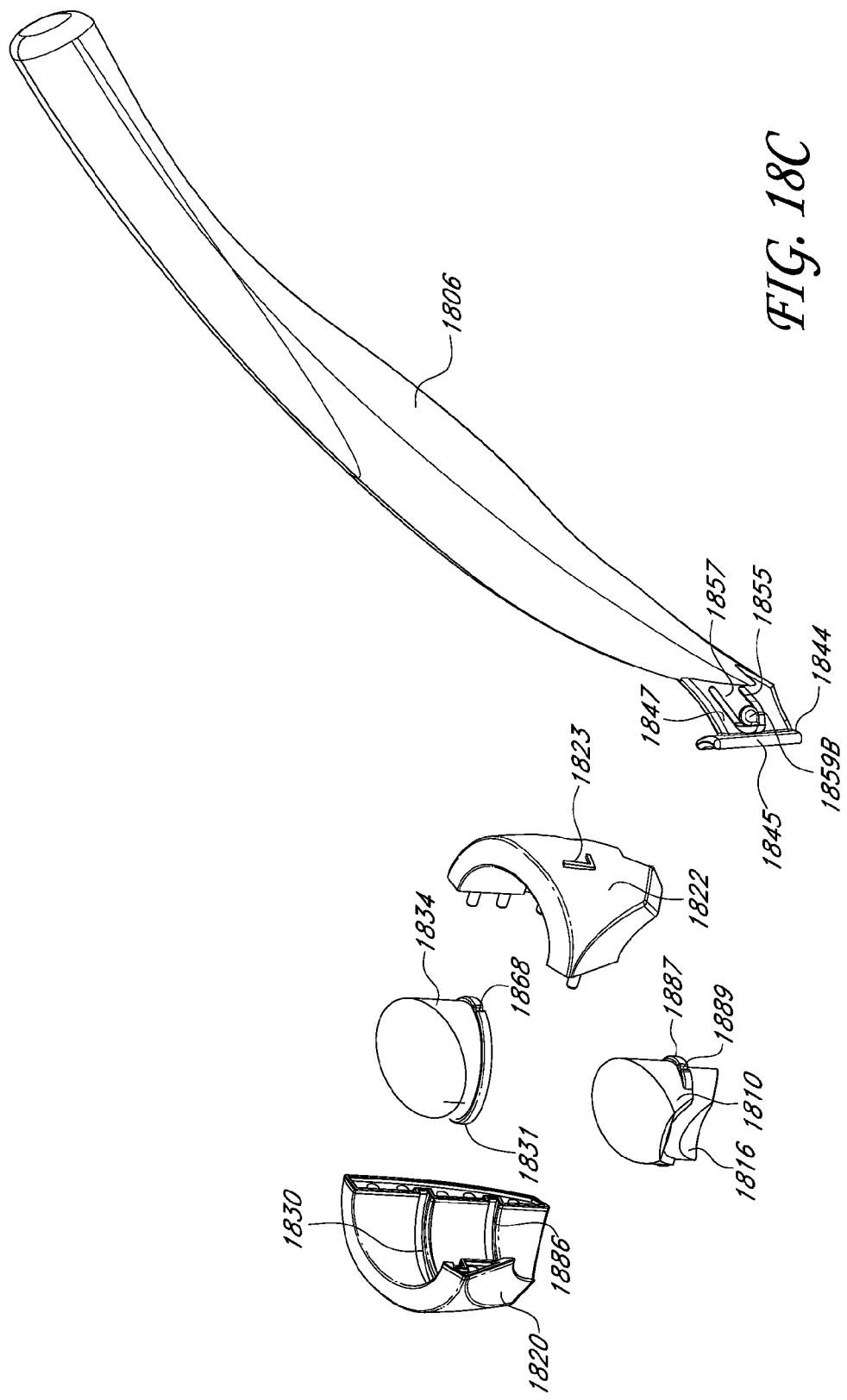
Figure 18D:
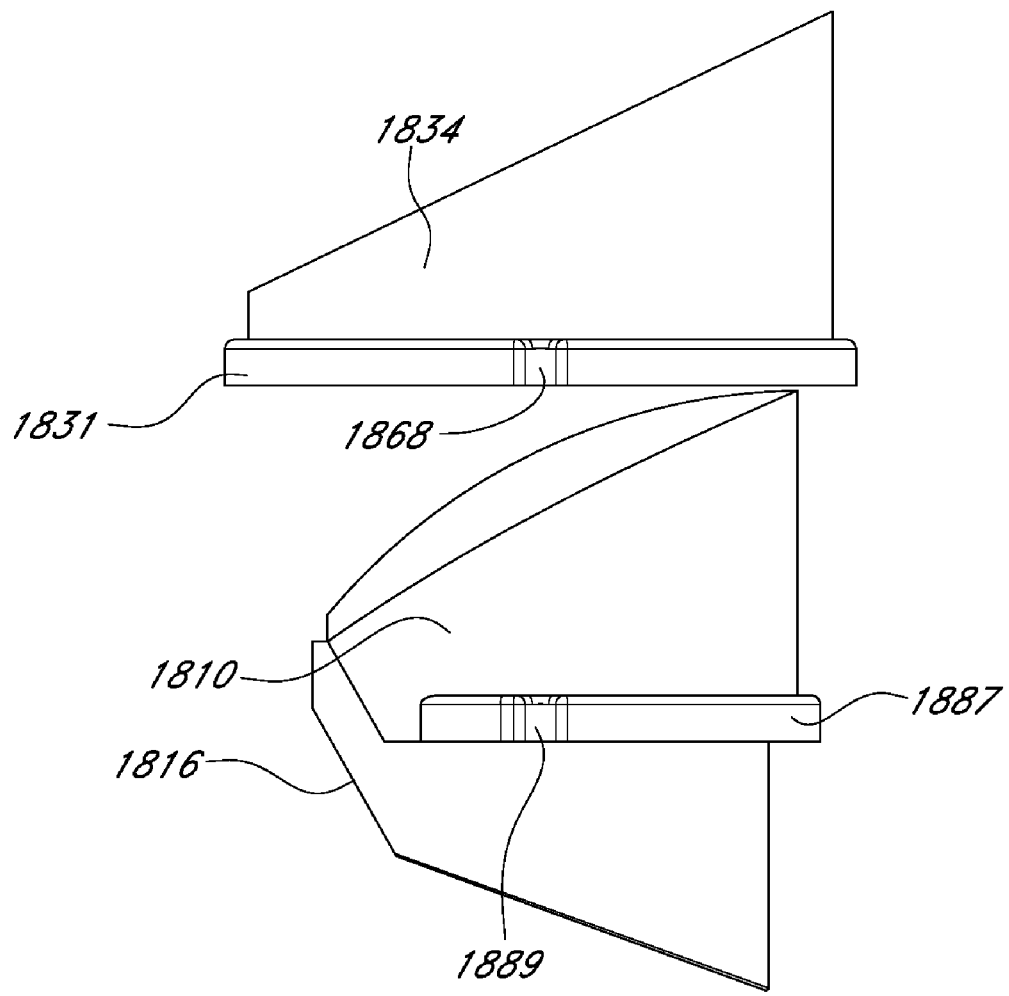
Figure 18E:
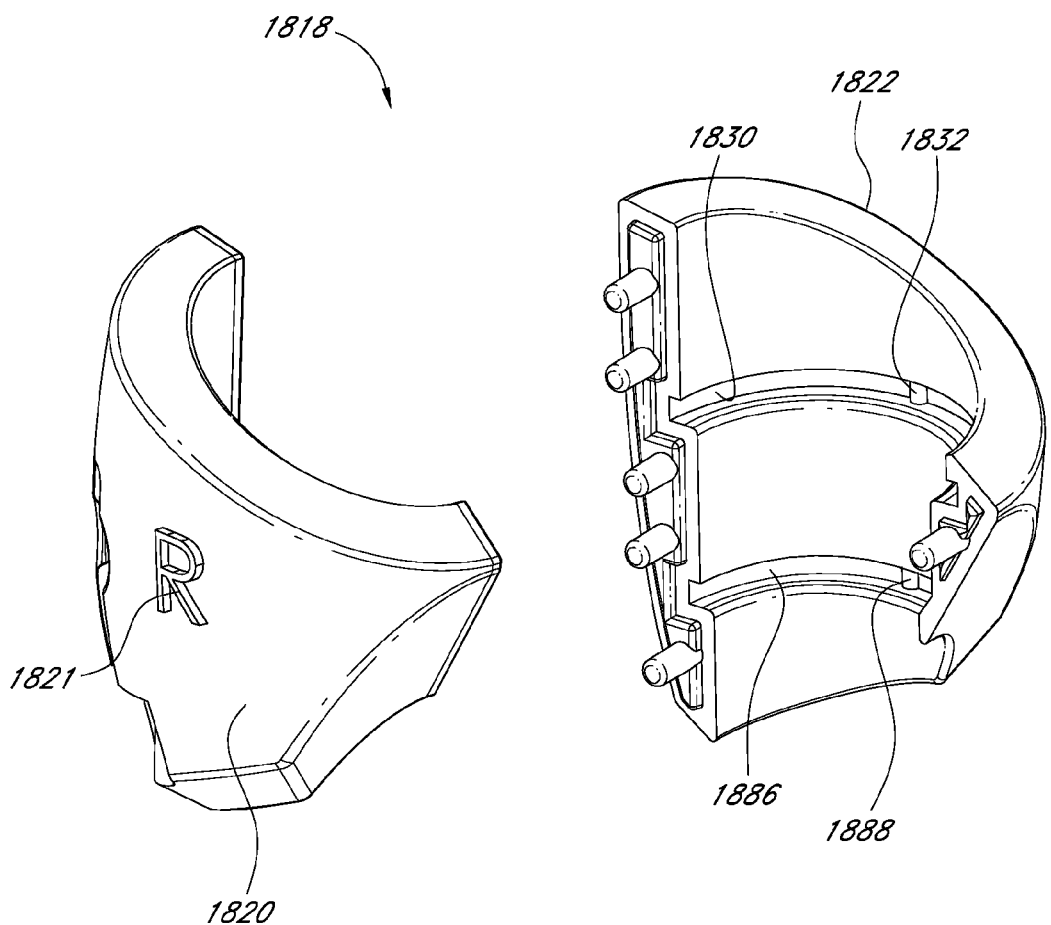
Figure 18F:
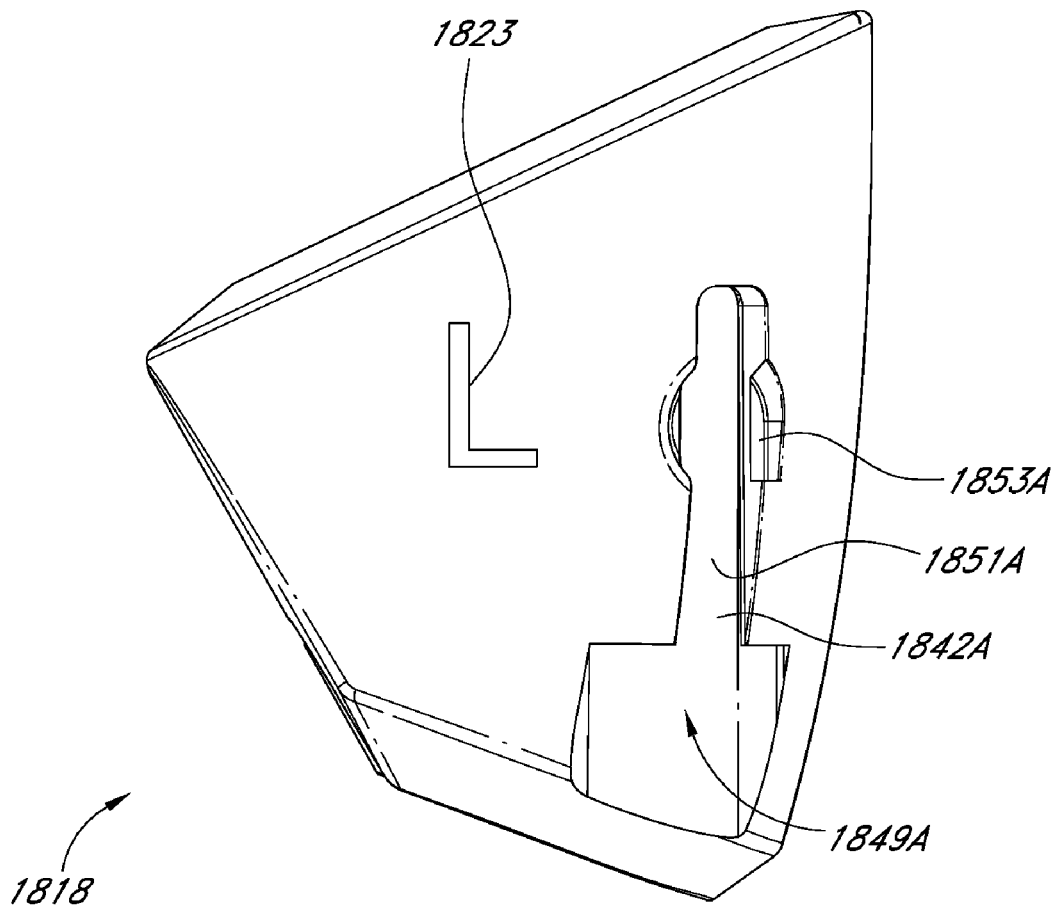

Turning now to FIGS. 18A-18F, FIG. 18A shows an embodiment of a gonioscope 1800, which can be similar in some regards to the gonioscope 1600 (or other embodiments) disclosed above, some of the disclosure of which can be applied to the gonioscope 1800, but may include differences such as those identified below. FIG. 18B shows the gonioscope 1800 with the handle 1806 unattached from the housing 1818. FIG. 18C is an exploded perspective view of the gonioscope 1800. FIG. 18D is a side view of the first and second gonioscopic optical elements 1810 and 1834. FIG. 18E is an exploded perspective view of the housing 1818. FIG. 18F is a side view of the housing 1818.

The gonioscope 1800 can include a housing 1818, which can be a two-part assembly having a right side piece 1820 and a left side piece 1822. The housing 1818 can have two connectors 1842A and 1842B, each capable of attaching the housing 1818 to the attachment region 1844 of the handle 1806. The attachment region 1844 can include an insert portion 1845 and an extender 1847. As shown in FIGS. 18B and 18C, the extender 1847 can include a curved cutout 1855 that defines a tab 1857 having a pair of protrusions 1859A, 1859B, one on each side of the tab 1857. In some embodiments, the protrusions 1859A, 1859B can be teardrop shaped having a pointed end at the lower end nearest the insert portion 1845. The connectors 1842A, 1842B can each include a slot 1849A, 1849B configured to slidably receive the insert portion 1845 therein, and an elongate opening 1851A, 1851B configured to receive the extender 1847. In some embodiments, the connectors 1842A, 1842B include indentations 1853A, 1853B in the outer surface of the housing 1818 positioned on both sides of the elongate openings 1851A, 1851B. In some embodiments, the indentations 1853A, 1853B can define a step at the lower end thereof. The indentations 1853A, 1853B can be configured to receive the protrusions 1859A, 1859B in a snap fit engagement. As the insert portion 1845 is inserted into one of the slots 1849A, 1849B, the protrusions 1859A, 1859B slide up the outside surface of the housing 1818, and the curved cutout 1855 allows the tab 1857 to flex away from the housing 1818. When the protrusions 1859A, 1859B reach the corresponding indentation 1853A or 1853B, the tab 1857 can return to its unflexed position causing the protrusions 1859A, 1859B to engage the corresponding indentation 1853A or 1853B. In some embodiments, the pointed ends on the teardrop shaped protrusions 1859A, 1859B can engage the step on the lower end of the indentation 1853A or 1853B to prevent the handle 1806 from disengaging from the connector 1842A or 1842B. Many variations are possible. For example, in some embodiments, the indentations 1853A, 1853B can be generally circular in shape. In some embodiments, the slots 1849A, 1849B can be tapered, so that the handle 1806 can be secured to the housing 1818 by inserting the insert portion 1845 into one of the slots 1849A, 1849B with enough force to wedge the insert portion 1845 into the tapered slot 1849A or 1849B. In some embodiments, the attachment region 1844 and connectors 1842A, 1842B can be configured so that the handle 1806 can be removed from the housing 1818 after it has been attached. In some embodiments, the attachment region 1844 and connectors 1842A, 1842B can be configured so that the handle 1806 cannot be easily removed from the housing 1818 after it has been attached.

In some embodiments, the right side piece 1820 can include a right side label 1821, which can be, for example, the letter R. Similarly, the left side piece 1822 can include a left side label 1823, which can be, for example, the letter L. The labels 1821, 1823 can be used to indicate to the user where the handle 1806 should be attached for a right-handed configuration and where the handle 1806 should be attached for a left-handed configuration.

In some embodiments, the handle 1806 can be ergonomically shaped, similarly to the handle 1606 discussed above. The handle 1806 can include a carved out area 1807, which can be positioned, for example, on the underside of the handle 1806. The carved out area 1807 can reduce the overall weight of the handle 1806. The other handles of the gonioscopic systems disclosed herein can also include a similar carved out area to reduce the overall weight of the system.

The gonioscope 1800 can include a first gonioscopic optical element 1810 and a second gonioscopic optical element 1834. The first gonioscopic optical element 1810 can include an annular ring 1887 that is configured to fit into a lower annular ridge 1886 on the inner surface of the housing 1818 to prevent the first gonioscopic optical element 1810 from moving longitudinally within the housing 1818. In some embodiments, the annular ring 1887 of the first gonioscopic optical element 1810 does not extend onto the recess, relief, or undercut 1816, so that the annular ring 1887 does not extend around the full circumference of the first gonioscopic optical element 1810. Similarly, in some embodiments, the lower annular ridge 1886 does not extend around the full circumference of the inner surface of the housing 1818. The lower annular ridge 1886 can include a protrusion 1888 that can be configured to fit into a notch 1889 in the annular ring 1887, to prevent the first gonioscopic optical element 1810 from rotating within the housing 1818.

The second gonioscopic optical element 1834 can include an annular ring 1831 configured to fit into an upper annular ridge 1830 formed in the inner surface of the housing 1818 for preventing the second gonioscopic optical element 1834 from moving longitudinally within the housing. The upper annular ridge 1830 can include a protrusion 1832 configured to fit into a notch 1868 in the annular ring 1831 to prevent the second gonioscopic optical element 1834 from rotating within the housing 1818.

When assembled, the first and second gonioscopic optical elements 1810, 1834 can be positioned as shown in FIG. 18D. The first and second gonioscopic optical elements 1810, 1834 can have optical properties that are similar to those of the first and second gonioscopic optical elements 1310, 1334 discussed above, and can be used to form an upright virtual image in a manner similar to the ray trace shown in FIG. 13D. Various other configurations are possible. For example, in some embodiments, the proximal surface of the first gonioscopic optical element 1810 can be flat, or can have a variety of other shapes, as discussed above.

Figure 19A:
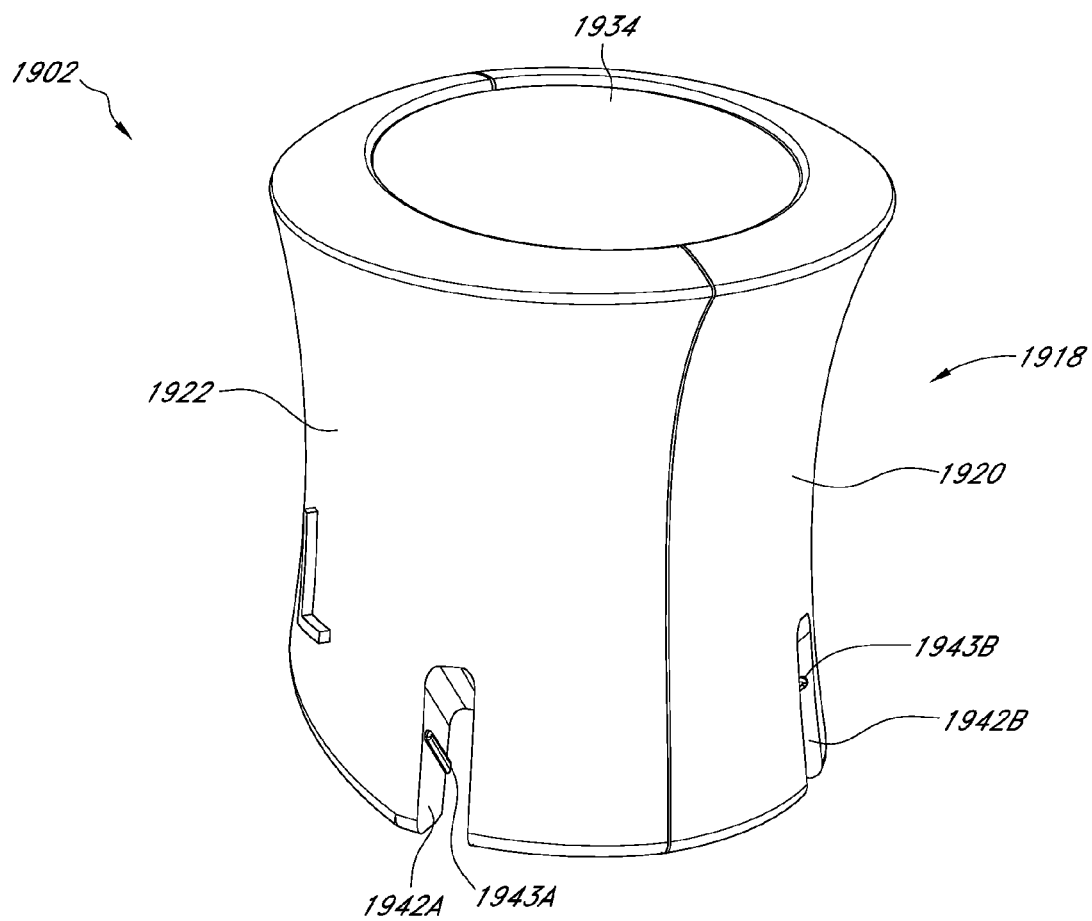
FIG. 19A schematically illustrates an embodiment of a gonioscopic attachment.

FIG. 19A is a perspective view of another embodiment of a gonioscopic attachment 1902, which can be similar to, or the same as, the gonioscopic attachment 1702 or any other gonioscopic attachment described herein. The gonioscopic attachment 1902 can include a housing 1918, which can be a two-part assembly having a right side piece 1920 and a left side piece 1922. The gonioscopic attachment 1902 can include two connectors 1942A, 1942B configured to attach to a gonioscope (not shown), which can be similar to the gonioscope 1704 disclosed above. The connectors 1942A, 1942B can be cutouts formed in the base portion of the housing 1918 with protrusions 1943A, 1943B extending into the cutouts. An attachment portion of the gonioscope can be inserted into one of the connectors 1942A, 1942B and past the protrusions 1943A, 1943B so that the housing 1918 snaps into a retained positions on the gonioscope. A second gonioscopic optical element 1934 can be supported within the housing 1918 in a manner similar to that discussed above in connection with the gonioscopic attachment 1702.

Figure 19B:
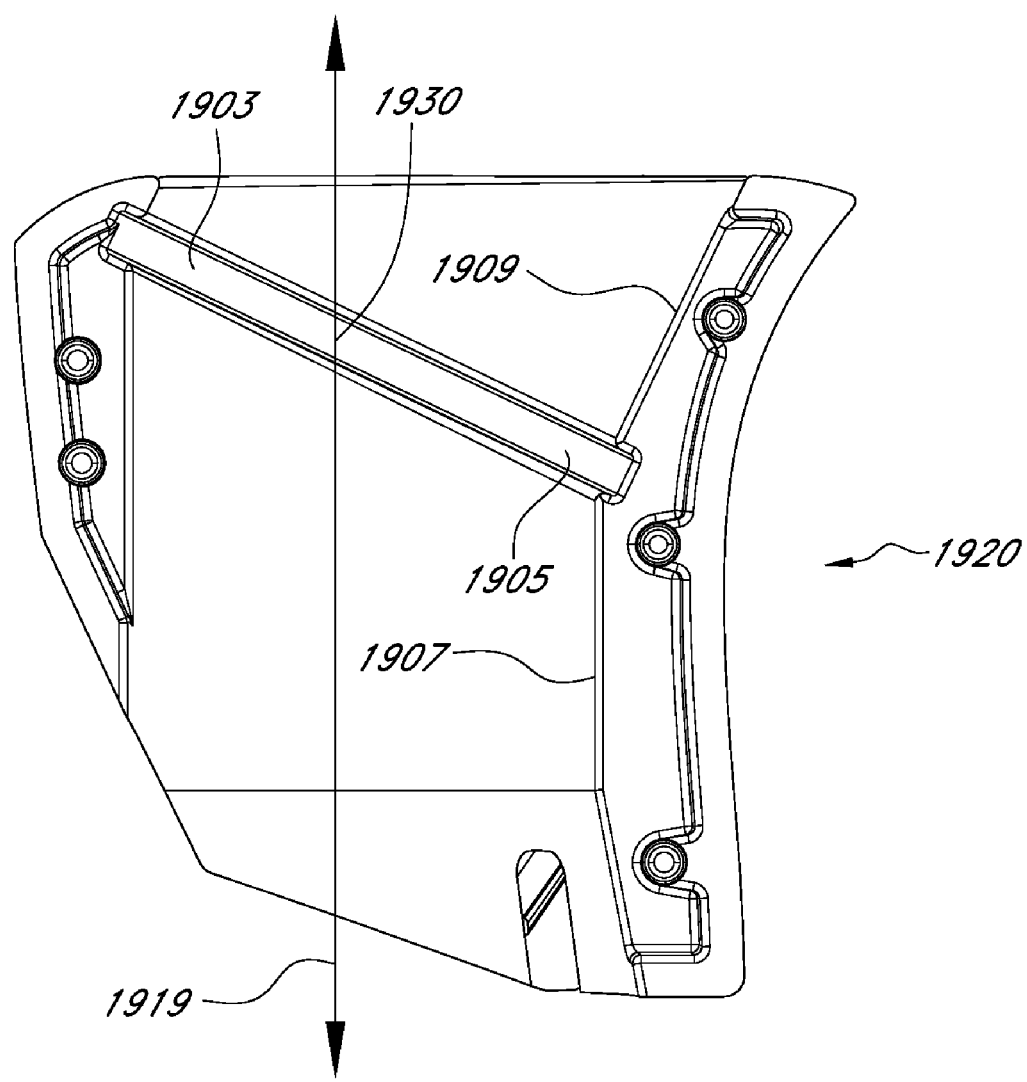
FIG. 19B schematically illustrates a portion of the housing of the gonioscopic attachment of FIG. 19A.

FIG. 19B is a side view of the right side piece 1920 of the housing 1918 shown in FIG. 19A. The inside surface of the housing 1918 can include an annular ridge 1930 configured to receive a corresponding annular protrusion 1931 (shown in FIG. 19C) on the second gonioscopic optical element 1934. In some embodiments, the annular ridge 1930 can be angled such that the portion 1903 of the annular ridge that is on the front side of the housing 1918 is nearer to the top of the housing 1918 than the portion 1905 of the annular ridge that is on the back side of the housing 1918. In some embodiments, the back wall of the housing can include a lower portion 1907 below the annular ridge 1930 and an upper portion 1909 above the annular ridge 1930. In some embodiments, the lower portion 1907 of the back wall can be substantially parallel to the longitudinal axis 1919 of the housing 1918, while the top portion 1909 of the back wall can deviate from the longitudinal axis 1919 of the housing 1918 by an angle of at least about 10° and/or no more than about 45°, although angles outside these ranges can also be used. In some embodiments, the angle between the top portion 1909 of the back wall and the longitudinal axis 1919 can be at least about 10°, 20°, 30°, or 40'; or no more than about 45°, 35°, 25°, or 15'; or any combination thereof; or any other suitable angle configured to accommodate the positioning of the second gonioscopic optical element 1934 in the housing 1918. Also, in some embodiments, the top portion 1909 of the back wall of the housing can deviate away from the lower portion 1907 of the back wall of the housing 1918 by and angle of at least 10°, 20°, 30°, or 40'; or no more than about 45°, 35°, 25°, or 15°; or any combination thereof; or any other suitable angle configured to accommodate the positioning of the second gonioscopic optical element 1934 in the housing 1918.

Figure 19C:
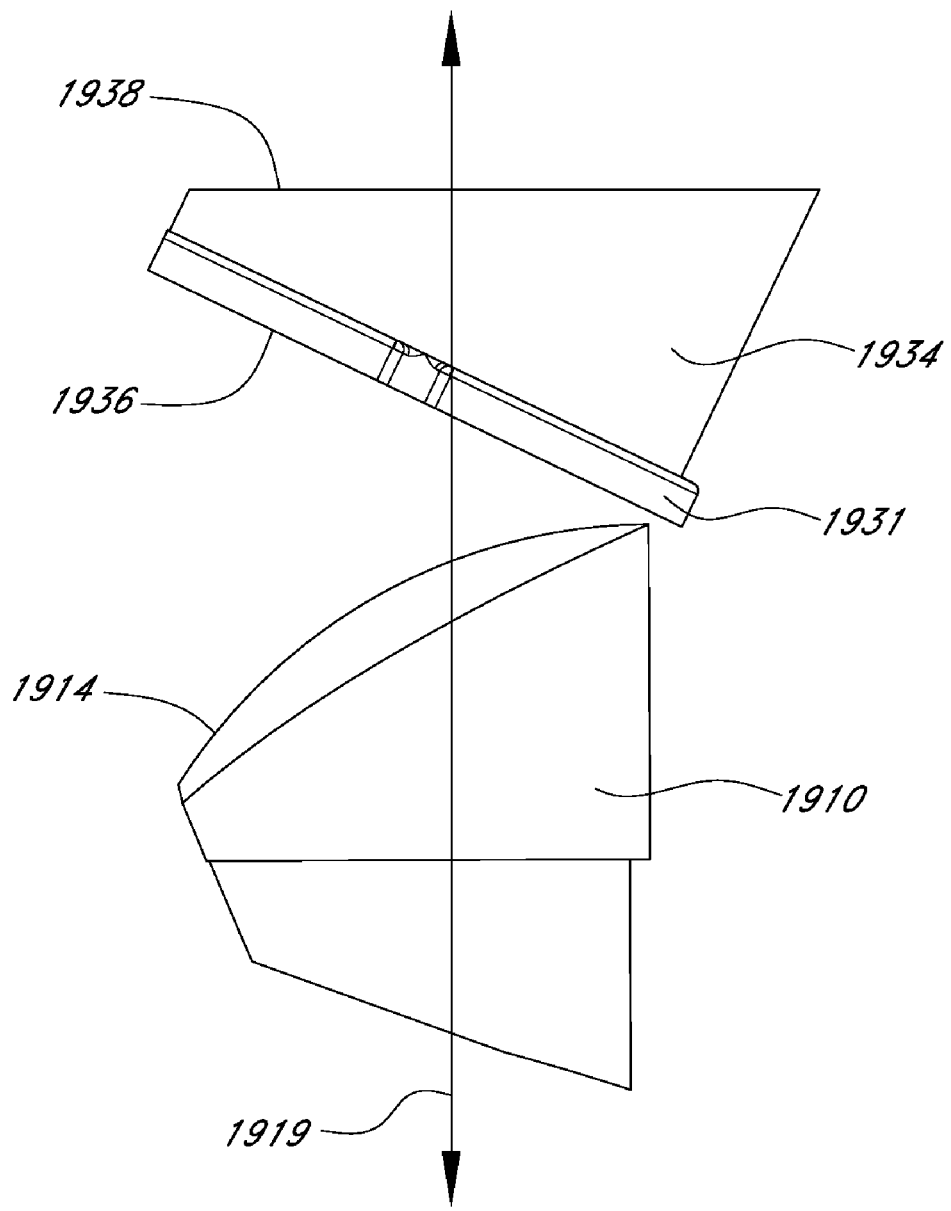
FIG. 19C schematically illustrates a gonioscopic optical system including two gonioscopic optical elements.

FIG. 19C shows a side view of the first gonioscopic optical element 1910 and second gonioscopic optical element 1934 as oriented during use. The first gonioscopic optical element 1910 can be a portion of the gonioscope that is inserted into the recess formed in the housing 1918 below the second gonioscopic optical element 1934, in a manner similar to that discussed above in connection with the gonioscopic assembly 1700. As can be seen by a comparison of FIGS. 17E and 19C, the angle between the first and second gonioscopic optical elements 1910, 1934 can be increased thereby increasing the space between the gonioscopic optical elements 1910, 1934. In some embodiments, the angle between the proximal surface 1914 of the first gonioscopic optical element 1910 and the distal surface 1936 of the second gonioscopic optical element 1934 can be at least about 30° and/or less than about 60°, although angles outside these ranges can also be used. In some embodiments, the angle between the proximal surface 1914 of the first gonioscopic optical element 1910 and the distal surface 1936 of the second gonioscopic optical element 1934 can be at least about 30°, 40°, 50°, or 60°; or no more than about 60°, 50°, 40°, or 30°; or any combination thereof; or any other angle suitable for redirecting the light to form a suitable image of the internal structure of the patient's eye. In some embodiments, the proximal surface 1938 of the second gonioscopic optical element 1934 can be substantially perpendicular to the longitudinal axis 1919 of the housing 1918. In some embodiment, the increased angle between the first and second gonioscopic optical elements 1910, 1934 can increase the field of view of the optical system created by the gonioscopic optical elements 1910, 1934.

While the invention has been discussed in terms of certain embodiments, it should be appreciated that the invention is not so limited. The embodiments are explained herein by way of example, and there are numerous modifications, variations and other embodiments that may be employed that would still be within the scope of the present invention. Components can be added, removed, and/or rearranged. Additionally, processing steps may be added, removed, or reordered. A wide variety of designs and approaches are possible. Where numerical values and/or ranges are disclosed, other numerical values can also be used. For example, some embodiments can use numerical values that are outside the disclosed ranges.

For purposes of this disclosure, certain aspects, advantages, and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

TABLE 1A

Lens Prescription
ldable Glass NFk5-PLaSF47

|  |  | RDY |  | THI |  | RMD | GLA | CCY | THC | GLC |
|---|---|---|---|---|---|---|---|---|---|---|
| BJ: |  | INFINITY |  | 0.000000 |  |  | 337400.613000 | 100 | 100 | 100 |
| 1: |  | INFINITY |  | 3.050000 |  |  | 337400.613000 | 100 | 100 | 100 |
|  | SLB: | "aq_humor" |  |  |  |  |  |  |  |  |
|  | XDE: | 0.000000 | YDE: | −4.500000 | ZDE: | 0.000000 |  |  |  |  |
|  | XDC: | 100 | YDC: | 100 | ZDC: | 100 |  |  |  |  |
|  | ADE: | 0.000000 | BDE: | 0.000000 | CDE: | 0.000000 |  |  |  |  |
|  | ADC: | 100 | BDC: | 100 | CDC: | 100 |  |  |  |  |
| 2: |  | −6.50000 |  | 0.550000 |  |  | 377100.571000 | 100 | 100 | 100 |
|  | SLB: | "cornea_pos" |  |  |  |  |  |  |  |  |
| 3: |  | −7.80000 |  | 0.100000 |  |  | WATER_SPECIAL | 100 | 100 |  |
|  | SLB: | "cornea_ant" |  |  |  |  |  |  |  |  |
| 4: |  | −7.80000 |  | 0.000000 |  |  | WATER_SPECIAL | PIK | 100 |  |
| 5: |  | −7.80000 |  | 5.000000 |  |  | PLASF47_SCHOTT | PIK | 100 |  |
|  | SLB: | "s1" |  |  |  |  |  |  |  |  |
| 6: |  | −60.69391 |  | 3.686433 |  |  |  | 0 | 0 |  |
|  | SLB: | "s2" |  |  |  |  |  |  |  |  |
|  | XDE: | 0.000000 | YDE: | 0.000000 | ZDE: | 0.000000 |  |  |  |  |
|  | XDC: | 100 | YDC: | 100 | ZDC: | 100 |  |  |  |  |
|  | ADE: | −25.000000 | BDE: | 0.000000 | CDE: | 0.000000 |  |  |  |  |
|  | ADC: | 100 | BDC: | 100 | CDC: | 100 |  |  |  |  |
| 7: |  | −10.00000 |  | 7.000000 |  |  | NFK5_SCHOTT | 100 | 100 |  |
|  | SLB: | "s3" |  |  |  |  |  |  |  |  |
|  | XDE: | 0.000000 | YDE: | 0.000000 | ZDE: | 0.000000 |  |  |  |  |
|  | XDC: | 100 | YDC: | 100 | ZDC: | 100 |  |  |  |  |
|  | ADE: | 20.000000 | BDE: | 0.000000 | CDE: | 0.000000 |  |  |  |  |
|  | ADC: | 100 | BDC: | 100 | CDC: | 100 |  |  |  |  |
| 8: |  | −13.69109 |  | 0.000000 |  |  |  | 0 | 100 |  |
|  | SLB: | "s4" |  |  |  |  |  |  |  |  |
|  | XDE: | 0.000000 | YDE: | 0.000000 | ZDE: | 0.000000 |  |  |  |  |
|  | XDC: | 100 | YDC: | 100 | ZDC: | 100 |  |  |  |  |
|  | ADE: | −27.645879 | BDE: | 0.000000 | CDE: | 0.000000 |  |  |  |  |
|  | ADC: | 0 | BDC: | 100 | CDC: | 100 |  |  |  |  |
| TO: |  | −13.69109 |  | −18.227722 |  |  |  | PIK | PIM |  |
|  | SLB: | "stop" |  |  |  |  |  |  |  |  |
| MG: |  | INFINITY |  | −6.220280 |  |  |  | 100 | 0 |  |
|  | XDE: | 0.000000 | YDE: | 0.000000 | ZDE: | 0.000000 |  | DAR |  |  |
|  | XDC: | 100 | YDC: | 100 | ZDC: | 100 |  |  |  |  |
|  | ADE: | 33.606693 | BDE: | 0.000000 | CDE: | 0.000000 |  |  |  |  |
|  | ADC: | 0 | BDC: | 100 | CDC: | 100 |  |  |  |  |

TABLE 1B

Lens Prescription: continued

SPECIFICATION DATA

| NA | 0.50000 |  |  |  |  |
|---|---|---|---|---|---|
| DIM | MM |  |  |  |  |
| WL | 642.73 | 590.86 | 542.02 | 500.48 | 465.61 |
| REF | 3 |  |  |  |  |
| WTW | 7 | 36 | 42 | 13 | 2 |
| XOB | 0.00000 | −1.00000 | 1.00000 | 0.00000 | 0.00000 |
| YOB | 0.00000 | 0.00000 | 0.00000 | −1.00000 | 1.00000 |
| WTF | 1.00000 | 1.00000 | 1.00000 | 1.00000 | 1.00000 |
| VUX | −0.15952 | −0.17155 | −0.15090 | −0.12488 | −0.22289 |
| VLX | −0.15952 | −0.15090 | −0.17155 | −0.12488 | −0.22289 |
| VUY | −0.04504 | −0.04563 | −0.04563 | 0.03192 | 0.21865 |
| VLY | −0.51624 | −0.51299 | −0.51299 | −0.45973 | −0.42105 |
| POL | N |  |  |  |  |

APERTURE DATA/EDGE DEFINITIONS

| CA |  |  |
|---|---|---|
| CIR S1 |  | 6.500000 |
| CIR S2 |  | 6.500000 |
| CIR S3 |  | 6.500000 |
| CIR S4 |  | 6.500000 |

TABLE 1B-continued

Lens Prescription: continued

| | | |
|---|---|---|
| CIR S5 | | 4.500000 |
| ADY S5 | | 0.380000 |
| CIR S6 | | 4.214129 |
| CIR S7 | | 5.458587 |
| CIR S8 | | 8.755432 |
| CIR S9 | | 8.755432 |
| CIR S10 | | 2.000000 |
| ADY S10 | | −8.500000 |

REFRACTIVE INDICES

| GLASS CODE | 642.73 | 590.86 | 542.02 | 500.48 | 465.61 |
|---|---|---|---|---|---|
| 337400.613000 | 1.336011 | 1.337307 | 1.338857 | 1.340538 | 1.342313 |
| 337400.613000 | 1.336011 | 1.337307 | 1.338857 | 1.340538 | 1.342313 |
| 377100.571000 | 1.375444 | 1.376989 | 1.378847 | 1.380873 | 1.383022 |
| WATER_SPECIAL | 1.331488 | 1.332938 | 1.334623 | 1.336410 | 1.338269 |
| PLASF47_SCHOTT | 1.801245 | 1.805771 | 1.811302 | 1.817422 | 1.824012 |
| NFK5_SCHOTT | 1.485722 | 1.487372 | 1.489324 | 1.491421 | 1.493620 |

SOLVES

PIM

PICKUPS

| PIK | RDY | S5 | Z1 | RDY | S3 | Z1 |
|---|---|---|---|---|---|---|
| PIK | RDY | S9 | Z1 | RDY | S8 | Z1 |
| PIK | RDY | S4 | Z1 | RDY | S3 | Z1 |

TABLE 1C

Lens Prescription: continued

| | POS 1 | POS 2 |
|---|---|---|
| ZOOM DATA | | |
| NA | 0.50000 | 0.02500 |
| VUY F1 | −0.04504 | −7.09774 |
| VLY F1 | −0.51624 | −8.03292 |
| VUY F2 | −0.04563 | −7.08544 |
| VLY F2 | −0.51299 | −8.01000 |
| VUY F3 | −0.04563 | −7.08544 |
| VLY F3 | −0.51299 | −8.01000 |
| VUY F4 | 0.03192 | −6.64203 |
| VLY F4 | −0.45973 | −7.65618 |
| VUY F5 | 0.21865 | −5.44682 |
| VLY F5 | −0.42105 | −6.88317 |
| VUX F1 | −0.15952 | −7.04185 |
| VLX F1 | −0.15952 | −7.04185 |
| VUX F2 | −0.17155 | −7.08547 |
| VLX F2 | −0.15090 | −7.03024 |
| VUX F3 | −0.15090 | −7.03024 |
| VLX F3 | −0.17155 | −7.08547 |
| VUX F4 | −0.12488 | −6.79332 |
| VLX F4 | −0.12488 | −6.79332 |
| VUX F5 | −0.22289 | −7.51140 |
| VLX F5 | −0.22289 | −7.51140 |
| CIR S9 | 8.75543 | 3.21363 |

This is a non-symmetric system. If elements with power are decentered or tilted, the first order properties are probably inadequate in describing the system characteristics.

TABLE 1C-continued

Lens Prescription: continued

| | POS 1 | POS 2 |
|---|---|---|
| INFINITE CONJUGATES | | |
| EFL | −22.2248 | −22.2248 |
| BFL | −41.5148 | −41.5148 |
| FFL | 28.3986 | 28.3986 |
| FNO | −2.0960 | −45.5425 |
| AT USED CONJUGATES | | |
| RED | −1.0478 | −1.0478 |
| FNO | −1.0000 | −20.0000 |
| OBJ DIS | 0.0000 | 0.0000 |
| TT | −5.0616 | −5.0616 |
| IMG DIS | −24.4480 | −24.4480 |
| OAL | 19.3864 | 19.3864 |
| PARAXIAL IMAGE | | |
| HT | 1.0478 | 1.0478 |
| THI | −18.2277 | −18.2277 |
| ANG | 44.3941 | 44.3941 |
| ENTRANCE PUPIL | | |
| DIA | 10.6037 | 0.4880 |
| THI | 12.4689 | 12.4689 |
| EXIT PUPIL | | |
| DIA | 19.8071 | 0.9116 |
| THI | 0.0000 | 0.0000 |
| STO DIA | 17.5109 | 6.4273 |

TABLE 2A

Lens Prescription
Acrylic Toroidal

| | | RDY | | THI | | RMD | | GLA | CCY | THC | GLC |
|---|---|---|---|---|---|---|---|---|---|---|---|
| OBJ: | | INFINITY | | 0.000000 | | | | 337400.613000 | 100 | 100 | 100 |
| 1: | | INFINITY | | 3.050000 | | | | 337400.613000 | 100 | 100 | 100 |
| | SLB: | "aq_humor" | | | | | | | | | |
| | XDE: | 0.000000 | YDE: | −4.500000 | ZDE: | 0.000000 | | | | | |
| | XDC: | 100 | YDC: | 100 | ZDC: | 100 | | | | | |
| | ADE: | 0.000000 | BDE: | 0.000000 | CDE: | 0.000000 | | | | | |
| | ADC: | 100 | BDC: | 100 | CDC: | 100 | | | | | |
| 2: | | −6.50000 | | 0.550000 | | | | 377100.571000 | 100 | 100 | 100 |
| | SLB: | "cornea_pos" | | | | | | | | | |
| 3: | | −7.80000 | | 0.100000 | | | | WATER_SPECIAL | 100 | 100 | |
| | SLB: | "cornea_ant" | | | | | | | | | |
| 4: | | −7.80000 | | 0.000000 | | | | WATER_SPECIAL | PIK | 100 | |
| 5: | | −7.80000 | | 5.000000 | | | | 'PMMAO' | PIK | 100 | |
| | SLB: | "s1" | | | | | | | | | |
| 6: | | −15.00000 | | 4.420310 | | | | | 100 | 0 | |
| | SLB: | "s2" | | | | | | | | | |
| | YTO: | | | | | | | | | | |
| | RDX: | −14.31507 | CCX: | 0 | | | | | | | |
| | K: | 1.423521 | KC: | 0 | IC: | YES | | | | | |
| | A: | 0.000000E+00 | B: | 0.000000E+00 | C: | 0.000000E+00 | D: | 0.000000E+00 | | | |
| | AC: | 100 | BC: | 100 | CC: | 100 | DC: | 100 | | | |
| | XDE: | 0.000000 | YDE: | 0.000000 | ZDE: | 0.000000 | | | | | |
| | XDC: | 100 | YDC: | 100 | ZDC: | 100 | | | | | |
| | ADE: | −25.000000 | BDE: | 0.000000 | CDE: | 0.000000 | | | | | |
| | ADC: | 100 | BDC: | 100 | CDC: | 100 | | | | | |
| 7: | | −8.04307 | | 6.403095 | | | | 'PMMAO' | 0 | 0 | |
| | SLB: | "s3" | | | | | | | | | |
| | XDE: | 0.000000 | YDE: | 0.000000 | ZDE: | 0.000000 | | | | | |
| | XDC: | 100 | YDC: | 100 | ZDC: | 100 | | | | | |
| | ADE: | 20.000000 | BDE: | 0.000000 | CDE: | 0.000000 | | | | | |
| | ADC: | 100 | BDC: | 100 | CDC: | 100 | | | | | |
| 8: | | −16.45206 | | 0.000000 | | | | | 0 | 100 | |
| | SLB: | "s4" | | | | | | | | | |
| | YTO: | | | | | | | | | | |
| | RDX: | −18.72123 | CCX: | 0 | | | | | | | |
| | K: | 0.000000 | KC: | 100 | IC: | YES | | | | | |
| | A: | 0.000000E+00 | B: | 0.000000E+00 | C: | 0.000000E+00 | D: | 0.000000E+00 | | | |
| | AC: | 100 | BC: | 100 | CC: | 100 | DC: | 100 | | | |
| | XDE: | 0.000000 | YDE: | 0.000000 | ZDE: | 0.000000 | | | | | |
| | XDC: | 100 | YDC: | 100 | ZDC: | 100 | | | | | |
| | ADE: | −31.238582 | BDE: | 0.000000 | CDE: | 0.000000 | | | | | |
| | ADC: | 0 | BDC: | 100 | CDC: | 100 | | | | | |
| STO: | | −16.45206 | | −16.737964 | | | | | PIK | PIM | |
| | SLB: | "stop" | | | | | | | | | |
| IMG: | | INFINITY | | −4.409535 | | | | | 100 | 0 | |
| | XDE: | 0.000000 | YDE: | 0.000000 | ZDE: | 0.000000 | | | DAR | | |
| | XDC: | 100 | YDC: | 100 | ZDC: | 100 | | | | | |
| | ADE: | 35.673815 | BDE: | 0.000000 | CDE: | 0.000000 | | | | | |
| | ADC: | 0 | BDC: | 100 | CDC: | 100 | | | | | |

TABLE 2B

Lens Prescription: continued

SPECIFICATION DATA

| | | | | | |
|---|---|---|---|---|---|
| NA | 0.50000 | | | | |
| DIM | MM | | | | |
| WL | 642.73 | 590.86 | 542.02 | 500.48 | 465.61 |
| REF | 3 | | | | |
| WTW | 7 | 36 | 42 | 13 | 2 |
| XOB | 0.00000 | −1.00000 | 1.00000 | 0.00000 | 0.00000 |
| YOB | 0.00000 | 0.00000 | 0.00000 | −1.00000 | 1.00000 |
| WTF | 1.00000 | 1.00000 | 1.00000 | 1.00000 | 1.00000 |
| VUX | −0.52691 | −0.57845 | −0.57845 | −0.52165 | −0.60441 |
| VLX | −0.52691 | −0.47944 | −0.57845 | −0.52165 | −0.60441 |
| VUY | −0.14090 | −0.14452 | −0.14452 | −0.11441 | −0.37026 |
| VLY | −1.34026 | −1.33731 | −1.33731 | −1.23578 | −1.14887 |
| POL | N | | | | |

TABLE 2B-continued

Lens Prescription: continued

APERTURE DATA/EDGE DEFINITIONS

|  |  |
|---|---|
| CA |  |
| CIR S1 | 6.500000 |
| CIR S2 | 6.500000 |
| CIR S3 | 6.500000 |
| CIR S4 | 6.500000 |
| CIR S5 | 4.500000 |
| ADY S5 | 0.380000 |
| CIR S6 | 5.260933 |
| CIR S7 | 6.442766 |
| CIR S8 | 10.992268 |
| CIR S9 | 10.579671 |
| CIR S10 | 2.000000 |
| ADY S10 | −12.300000 |

PRIVATE CATALOG

| PWL | 1013.98 | 852.11 | 706.52 | 656.27 | 643.85 | 589.29 | 587.56 |
|---|---|---|---|---|---|---|---|
|  | 546.07 | 486.13 | 479.99 | 435.84 | 404.66 | 365.01 |  |
| 'PMMAO' | 1.483115 | 1.484965 | 1.487787 | 1.489201 | 1.489603 | 1.491681 | 1.491757 |
|  | 1.493795 | 1.497760 | 1.498258 | 1.502557 | 1.506607 | 1.513613 |  |

REFRACTIVE INDICES

| GLASS CODE | 642.73 | 590.86 | 542.02 | 500.48 | 465.61 |
|---|---|---|---|---|---|
| 337400.613000 | 1.336011 | 1.337307 | 1.338857 | 1.340538 | 1.342313 |
| 337400.613000 | 1.336011 | 1.337307 | 1.338857 | 1.340538 | 1.342313 |
| 377100.571000 | 1.375444 | 1.376989 | 1.378847 | 1.380873 | 1.383022 |
| WATER_SPECIAL | 1.331488 | 1.332938 | 1.334623 | 1.336410 | 1.338269 |
| 'PMMAO' | 1.489640 | 1.491613 | 1.494020 | 1.496671 | 1.499510 |

SOLVES

PIM

PICKUPS

| PIK | RDY | S5 | Z1 | RDY | S3 | Z1 |
|---|---|---|---|---|---|---|
| PIK | RDY | S9 | Z1 | RDY | S8 | Z1 |
| PIK | RDY | S4 | Z1 | RDY | S3 | Z1 |

TABLE 2C

Lens Prescription: continued

|  | POS 1 | POS 2 |
|---|---|---|
| ZOOM DATA |  |  |
| NA | 0.50000 | 0.02500 |
| CIR S9 | 10.57967 | 2.75888 |
| This is a non-symmetric system. If elements with power are decentered or tilted, the first order properties are probably inadequate in describing the system characteristics. |  |  |
| INFINITE CONJUGATES |  |  |
| EFL | −89.4363 | −89.4363 |
| BFL | −108.4985 | −108.4985 |
| FFL | 116.7095 | 116.7095 |
| FNO | −5.9875 | −129.6198 |
| AT USED CONJUGATES |  |  |
| RED | −1.0260 | −1.0260 |
| FNO | −1.0000 | −20.0000 |
| OBJ DIS | 0.0000 | 0.0000 |
| TT | −1.6241 | −1.6241 |
| IMG DIS | −21.1475 | −21.1475 |
| OAL | 19.5234 | 19.5234 |
| PARAXIAL IMAGE |  |  |
| HT | 1.0260 | 1.0260 |
| THI | −16.7380 | −16.7380 |
| ANG | 38.2816 | 38.2816 |
| ENTRANCE PUPIL |  |  |
| DIA | 14.9372 | 0.6900 |
| THI | 18.0047 | 18.0047 |
| EXIT PUPIL |  |  |
| DIA | 18.1209 | 0.8371 |
| THI | 0.0000 | 0.0000 |
| STO DIA | 21.2558 | 5.5531 |

TABLE 3A

Lens Prescription
Y DOE 3rd order

|  |  | RDY | | THI | | RMD | GLA | CCY | THC | GLC |
|---|---|---|---|---|---|---|---|---|---|---|
| OBJ: |  | INFINITY | | 0.000000 | | | 337400.613000 | 100 | 100 | 100 |
| 1: |  | INFINITY | | 3.050000 | | | 337400.613000 | 100 | 100 | 100 |
|  | SLB: | "aq_humor" | | | | | | | | |
|  | XDE: | 0.000000 | YDE: | −4.500000 | ZDE: | 0.000000 | | | | |
|  | XDC: | 100 | YDC: | 100 | ZDC: | 100 | | | | |
|  | ADE: | 0.000000 | BDE: | 0.000000 | CDE: | 0.000000 | | | | |
|  | ADC: | 100 | BDC: | 100 | CDC: | 100 | | | | |
| 2: |  | −6.50000 | | 0.550000 | | | 377100.571000 | 100 | 100 | 100 |
|  | SLB: | "cornea_pos" | | | | | | | | |
| 3: |  | −7.80000 | | 0.100000 | | | WATER_SPECIAL | 100 | 100 | |
|  | SLB: | "cornea_ant" | | | | | | | | |
| 4: |  | −7.80000 | | 0.000000 | | | WATER_SPECIAL | PIK | 100 | |
| 5: |  | −7.80000 | | 4.000000 | | | SILICA_SPECIAL | PIK | 100 | |
|  | SLB: | "s1" | | | | | | | | |
| 6: |  | INFINITY | | 6.000000 | | | | 100 | 100 | Diffractive Surface Prescription |
|  | SLB: | "s2" | | | | | | | | |
|  | HOE: | | | | | | | | | |
|  | HV1: | REA | HV2: | REA | HOR: | 1.000000 | | | | |
|  | HX1: | 0.000000E+00 | HY1: | 0.000000E+00 | HZ1: | 0.100000E+01 | | | | |
|  | CX1: | 100 | CY1: | 100 | CZ1: | 100 | | | | |
|  | HX2: | 0.000000E+00 | HY2: | 0.000000E+00 | HZ2: | 0.100000E+01 | | | | |
|  | CX2: | 100 | CY2: | 100 | CZ2: | 100 | | | | |
|  | HWL: | 542.02 | | | HCT: | XY | | | | |
|  |  | | | | BLT: | IDEAL | | | | |
|  | HDC/HCC | | | | | | | | | |
|  | C2: | 5.7669E−02 | C3: | 7.5712E−04 | C5: | −1.8042E−02 | | | | |
|  | C2: | 0 | C3: | 0 | C5: | 0 | | | | |
|  | C7: | 2.4984E−03 | C9: | 2.5613E−03 | | | | | | |
|  | C7: | 0 | C9: | 0 | | | | | | |
|  | XDE: | 0.000000 | YDE: | 0.000000 | ZDE: | 0.000000 | | | | |
|  | XDC: | 100 | YDC: | 100 | ZDC: | 100 | | | | |
|  | ADE: | −15.000000 | BDE: | 0.000000 | CDE: | 0.000000 | | | | |
|  | ADC: | 100 | BDC: | 100 | CDC: | 100 | | | | |

TABLE 3B

Lens Prescription: continued

| 7: |  | −10.00000 | | 4.000000 | | | | SILICA_SPECIAL | 100 | 100 |
|---|---|---|---|---|---|---|---|---|---|---|
|  | SLB: | "s3" | | | | | | | | |
|  | YTO: | | | | | | | | | |
|  | RDX: | −8.03490 | CCX: | 0 | | | | | | |
|  | K: | 0.000000 | KC: | 100 | IC: | YES | | | | |
|  | A: | 0.000000E+00 | B: | 0.000000E+00 | C: | 0.000000E+00 | D: | 0.000000E+00 | | |
|  | AC: | 100 | BC: | 100 | CC: | 100 | DC: | 100 | | |
|  | XDE: | 0.000000 | YDE: | 0.000000 | ZDE: | 0.000000 | | | | |
|  | XDC: | 100 | YDC: | 100 | ZDC: | 100 | | | | |
|  | ADE: | 25.000000 | BDE: | 0.000000 | CDE: | 0.000000 | | | | |
|  | ADC: | 100 | BDC: | 100 | CDC: | 100 | | | | |
| 8: |  | −12.53111 | | 0.000000 | | | | | 0 | 100 |
|  | SLB: | "s4" | | | | | | | | |
|  | YTO: | | | | | | | | | |
|  | RDX: | −8.76308 | CCX: | 0 | | | | | | |
|  | K: | 0.000000 | KC: | 100 | IC: | YES | | | | |
|  | A: | 0.000000E+00 | B: | 0.000000E+00 | C: | 0.000000E+00 | D: | 0.000000E+00 | | |
|  | AC: | 100 | BC: | 100 | CC: | 100 | DC: | 100 | | |
|  | XDE: | 0.000000 | YDE: | 0.000000 | ZDE: | 0.000000 | | | | |
|  | XDC: | 100 | YDC: | 100 | ZDC: | 100 | | | | |
|  | ADE: | −16.906079 | BDE: | 0.000000 | CDE: | 0.000000 | | | | |
|  | ADC: | 0 | BDC: | 100 | CDC: | 100 | | | | |
| STO: |  | −12.53111 | | −18.200798 | | | | | PIK | 0 |
|  | XDE: | 0.000000 | YDE: | 0.000000 | ZDE: | 0.000000 | | | DAR | |
|  | XDC: | 100 | YDC: | 100 | ZDC: | 100 | | | | |
|  | ADE: | 0.000000 | BDE: | 0.000000 | CDE: | 0.000000 | | | | |
|  | ADC: | 100 | BDC: | 100 | CDC: | 100 | | | | |
| IMG: |  | INFINITY | | 0.000000 | | | | | 100 | 100 |

TABLE 3C

DOE construction parameters

H-1 Hologram formed by two point sources at (X1,Y1,Z1), (X2,Y2,Z2)

| X1 = 0.000000E+00 | Y1 = 0.000000E+00 | Z1 = 0.100000E+01 | DIVERGING |
|---|---|---|---|
| X2 = 0.000000E+00 | Y2 = 0.000000E+00 | Z2 = 0.100000E+01 | DIVERGING |

| THE CONSTRUCTION WAVELENGTH IS | 542.02 NM |
|---|---|
| THE BEAM IS DIFFRACTED INTO ORDER | 1 |
| THE GRATING FREQUENCY AT THE NODE OF THE SUBSTRATE IS | 106.40 LINES/MM |

The phase function is in the form of a sum of monomials in (X,Y), where the coordinates are on the surface of the substrate.

| Power of | | |
|---|---|---|
| X | Y | Coefficient |
| 0 | 1 | 0.576687E−01 |
| 2 | 0 | 0.757122E−03 |
| 0 | 2 | −0.180421E−01 |
| 2 | 1 | 0.249835E−02 |
| 0 | 3 | 0.256127E−02 |

TABLE 3D

Lens Prescription

No solves defined in system

PICKUPS

| PIK | RDY | S5 | Z1 | RDY | S3 | Z1 |
|---|---|---|---|---|---|---|
| PIK | RDY | S9 | Z1 | RDY | S8 | Z1 |
| PIK | RDY | S4 | Z1 | RDY | S3 | Z1 |

| | POS 1 | POS 2 |
|---|---|---|
| ZOOM DATA | | |
| NA | 0.50000 | 0.02500 |
| CIR S9 | 5.27103 | 0.50711 |

This is a non-symmetric system. If elements with power are decentered or tilted, the first order properties are probably inadequate in describing the system characteristics.

| INFINITE CONJUGATES | | |
|---|---|---|
| EFL | 67.6995 | 67.6995 |
| BFL | 66.2655 | 66.2655 |
| FFL | −73.0345 | −73.0345 |
| FNO | 3.3075 | 74.6310 |
| AT USED CONJUGATES | | |
| RED | −1.2411 | −1.2411 |
| FNO | −1.0000 | −20.0000 |
| OBJ DIS | 0.0000 | 0.0000 |
| TT | −0.5008 | −0.5008 |
| IMG DIS | −18.2008 | −18.2008 |
| OAL | 17.7000 | 17.7000 |
| PARAXIAL IMAGE | | |
| HT | 1.2411 | 1.2411 |
| THI | −17.7534 | −17.7534 |
| ANG | 35.7235 | 35.7235 |
| ENTRANCE PUPIL | | |
| DIA | 20.4688 | 0.9071 |
| THI | 19.5669 | 19.5669 |
| EXIT PUPIL | | |
| DIA | 20.0352 | 0.8879 |
| THI | 0.0000 | 0.0000 |
| STO DIA | 10.5241 | 1.0142 |

What is claimed is:

1. A gonioscopic attachment for redirecting light exiting a gonioscope, the gonioscopic attachment comprising:
    a housing defining an interior chamber, the housing comprising a connector configured to allow the housing to be removably attached to a gonioscope; and
    an attachment optical element secured by the housing, the attachment optical element being substantially wedge-shaped,
    the interior chamber comprising a recess located below the attachment optical element, the recess configured to receive at least a portion of a gonioscopic optical element of the gonioscope such that the attachment optical element is positioned with respect to the gonioscopic optical element such that light exiting the gonioscopic optical element is directed toward the attachment optical element,
    wherein the connector is configured to provide a snap-fit connection with an attachment region on a handle of the gonioscope, the attachment region having a thickness, the connector comprising a cutout located at a base portion of said housing, said cutout having a width that is wide enough to receive said attachment region of said gonioscope, said cutout comprising a narrowed region having a narrowed width that is less than the thickness of the attachment region.

2. The gonioscopic attachment of claim 1, wherein the recess is configured to receive an upper portion of the gonioscopic optical element such that a lower portion of the gonioscopic optical element extends out below the housing.

3. The gonioscopic attachment of claim 1, wherein the attachment optical element is configured such that at least a portion of the light reflected by an object within an eye and directed toward the attachment optical element is transmitted through the attachment optical element and forms an upright virtual image of the object within the eye viewable by a microscope without relying on reflection from one or more surfaces of the gonioscopic attachment.

4. A gonioscopic attachment for redirecting light exiting a gonioscope, the gonioscopic attachment comprising:
    a housing defining an interior chamber; and
    an attachment optical element secured to the housing, the attachment optical element being substantially wedge-shaped,
    wherein the housing is configured to attach to the gonioscope and position the attachment optical element with respect to a gonioscopic optical element of the gonioscope such that light exiting the gonioscopic optical element is directed toward the attachment optical element,
    wherein the housing comprises at least one right-handed connector configured to allow the housing to be removably attached to the gonioscope in a right-handed configuration and a left-handed connector configured to allow the housing to be removably attached to the gonioscope in a left-handed configuration.

5. The gonioscopic attachment of claim 4, wherein the connector is an integral portion of the housing.

6. The gonioscopic attachment of claim 5, wherein the connector comprises a cutout located at a base portion of the housing.

7. The gonioscopic attachment of claim 4, wherein the attachment optical element is configured such that at least a portion of the light reflected by a trabecular meshwork of an eye and directed toward the attachment optical element is transmitted through the attachment optical element and forms an upright virtual image of the trabecular meshwork viewable by a microscope without relying on reflection.

8. A gonioscopic attachment for redirecting light exiting a gonioscope, the gonioscopic attachment comprising:
- a housing defining an interior chamber;
- a connector configured to allow the housing to be removably attached to a gonioscope; and
- an attachment optical element secured by the housing, the attachment optical element being substantially wedge-shaped,
- wherein the housing is configured to attach to the gonioscope and position the attachment optical element with respect to a gonioscopic optical element of the gonioscope such that light exiting the gonioscopic optical element is directed toward the attachment optical element.,
- wherein the attachment optical element comprises a transparent material, a distal surface to receive the light exiting the gonioscopic optical element of the gonioscope, and a proximal surface to output light transmitted through the transparent material.

9. The gonioscopic attachment of claim 8, wherein the housing is substantially tubular in shape.

10. The gonioscopic attachment of claim 8, wherein at least one of the distal surface and the proximal surface of the attachment optical element is substantially planar.

11. The gonioscopic attachment of claim 8, wherein both the distal surface and the proximal surface of the attachment optical element are substantially planar.

12. The gonioscopic attachment of claim 8, wherein the attachment optical element is configured such that the light output by the proximal surface of the attachment optical element forms a virtual image viewable by a microscope.

13. The gonioscopic attachment of claim 8, wherein the attachment optical element is configured such that the light output by the proximal surface of the attachment optical element forms an upright image viewable by a microscope.

14. The gonioscopic attachment of claim 8, wherein the attachment optical element is configured such that at least a portion of the light is transmitted through the transparent material without internal reflection and forms an image viewable by a microscope.

15. The gonioscopic attachment of claim 8, wherein the attachment optical element is configured such that at least a portion of the light is transmitted through the transparent material directly from the distal surface to the proximal surface without striking any other surfaces of the attachment optical element and forms an image viewable by a microscope.

16. The gonioscopic attachment of claim 8, wherein the housing is configured to attach to the gonioscope such that an air gap is formed between the gonioscopic optical element and the attachment optical element.

17. The gonioscopic attachment of claim 8, wherein the attachment optical element comprises a transparent plastic material.

18. The gonioscopic attachment of claim 8, wherein the housing comprises an opaque plastic material.

19. The gonioscopic attachment of claim 8, wherein the housing comprises an interior surface, at least a portion of the interior surface configured to reduce reflections.

20. The gonioscopic attachment of claim 19, wherein the interior surface comprises a dark colored material.

21. The gonioscopic attachment of claim 8, wherein the interior chamber of the housing comprises a recess located below the attachment optical element.

22. The gonioscopic attachment of claim 8, wherein the connector is an integral portion of the housing.

23. The gonioscopic attachment of claim 22, wherein the connector comprises a cutout located at a base portion of the housing.

24. The gonioscopic attachment of claim 8, wherein the proximal surface of the attachment optical element is curved.

25. The gonioscopic attachment of claim 8, wherein the attachment optical element comprises a lens having at least one curved surface that provides optical power.

26. The gonioscopic attachment of claim 8, wherein said attachment optical element is configured to redirect the light using refraction.

27. The gonioscopic attachment of claim 8, wherein the attachment optical element is configured such that the light reflected from an object within an eye and output by the proximal surface of the attachment optical element forms a virtual image of the object within the eye viewable by a microscope.

28. The gonioscopic attachment of claim 8, wherein the attachment optical element is configured such that the light reflected from a trabecular meshwork of a subject's eye and output by the proximal surface of the attachment optical element forms an upright image of the trabecular meshwork viewable by a microscope.

29. The gonioscopic attachment of claim 8, wherein the attachment optical element is configured such that at least a portion of the light reflected from an object within an eye is transmitted through the transparent material and forms an image of the object within the eye viewable by a microscope without relying on reflection from one or more surfaces of the gonioscopic attachment.

30. The gonioscopic attachment of claim 8, wherein the attachment optical element is configured such that at least a portion of the light reflected from a trabecular meshwork of a subject's eye and is transmitted through the transparent material directly from the distal surface to the proximal surface without striking any other surfaces of the attachment optical element and forms an upright virtual image of the trabecular meshwork viewable by a microscope.

31. A gonioscopic attachment for redirecting light exiting a gonioscope, the gonioscopic attachment comprising:
- a housing defining an interior chamber;
- a connector configured to allow the housing to be removably attached to a gonioscope for use on a subject's eye, wherein the eye comprises an optical axis; and
- an attachment optical element secured by the housing, the attachment optical element being substantially wedge-shaped,
- wherein the housing is configured to attach to the gonioscope and position the attachment optical element with respect to a gonioscopic optical element of the gonioscope such that light reflected from an object within the eye, transmitted through the gonioscopic optical element, and exiting the gonioscopic optical element is directed toward the attachment optical element,
- wherein said attachment optical element is configured to receive the light exiting the gonioscopic optical element and redirect at least a portion of the light such that light reflected from the object within the eye and output by the attachment optical element is directed with an average deviation of no more than 20° from parallel to the optical axis.

32. The gonioscopic attachment of claim 31, wherein said attachment optical element is configured to receive the light reflected from the object within the eye and exiting the gonioscopic optical element and redirect at least a portion of the light such that light reflected from the object within the eye and output by the attachment optical element is directed with an average deviation of no more than 5° from parallel to the optical axis.

33. The gonioscopic attachment of claim 32, wherein the object within the eye is a trabecular meshwork of the eye.

34. The gonioscopic attachment of claim 31, wherein said attachment optical element is configured to receive the light reflected from the object within the eye and exiting the gonioscopic optical element and redirect at least a portion of the light such that light reflected from the object within the eye and output by the attachment optical element is directed with an average deviation of no more than 1° from parallel to the optical axis.

35. The gonioscopic attachment of claim 31, wherein said attachment optical element is configured to redirect the light reflected from the object within the eye so as to form an image of the object within the eye viewable by a microscope without the attachment optical element relying on reflections.

36. The gonioscopic attachment of claim 31, wherein said attachment optical element is configured to redirect the light reflected from the object within the eye and exiting the gonioscopic optical element using refraction.

37. The gonioscopic attachment of claim 31, wherein said attachment optical element is configured to receive the light reflected from a trabecular meshwork within the eye and exiting the gonioscopic optical element and redirect at least a portion of the light such that light reflected from the trabecular meshwork and output by the attachment optical element is directed with an average deviation of no more than 10° from parallel to the optical axis.

38. The gonioscopic attachment of claim 31, wherein the object within the eye is a trabecular meshwork of the eye.

39. The gonioscopic attachment of claim 31, wherein the interior chamber of the housing comprises a recess located below the attachment optical element.

40. The gonioscopic attachment of claim 31, wherein the connector is an integral portion of the housing.

41. The gonioscopic attachment of claim 31, wherein the attachment optical element comprises a lens having at least one curved surface that provides optical power.

42. The gonioscopic attachment of claim 31, wherein both a distal surface and a proximal surface of the attachment optical element are substantially planar.

43. The gonioscopic attachment of claim 31, wherein the attachment optical element is configured such that light reflected by a trabecular meshwork of the eye and output by the attachment optical element forms a virtual image of the trabecular meshwork viewable by a microscope.

44. The gonioscopic attachment of claim 31, wherein the attachment optical element is configured such that light reflected by a trabecular meshwork of the eye and output by the attachment optical element forms an upright image of the trabecular meshwork viewable by a microscope.

45. The gonioscopic attachment of claim 31, wherein the attachment optical element is configured such that at least a portion of the light reflected by a trabecular meshwork of the eye is transmitted through the attachment optical element and forms an image of the trabecular meshwork viewable by a microscope without the attachment optical element relying on reflection.

46. The gonioscopic attachment of claim 31, wherein said attachment optical element is configured to redirect the light reflected by a trabecular meshwork of the eye so as to form an upright virtual image of the trabecular meshwork viewable by a microscope without the attachment optical element relying on reflections.

47. A gonioscopic assembly for intraocular observation, the gonioscopic assembly comprising:
    a first gonioscopic optical element comprising transparent material and having a distal surface, the distal surface being concave and having a radius of curvature between about 5mm and 11mm;
    a handle supporting the first gonioscopic optical element;
    a housing attached to the handle or the first gonioscopic optical element, the housing defining an interior chamber; and
    a second gonioscopic optical element supported by the housing;
    wherein the first gonioscopic optical element is substantially wedge-shaped having a narrow end closer to a first side of the housing than to a second side of the housing and a wide end closer to the second side of the housing than to the first side of the housing, and the second gonioscopic optical element is substantially wedge-shaped having a narrow end closer to the first side of the housing than to the second side of the housing and a wide end closer to the second side of the housing than to the first side of the housing.

48. The gonioscopic assembly of claim 47, wherein the second gonioscopic optical element comprises a lens having at least one curved surface that provides optical power.

49. The gonioscopic assembly of claim 47, wherein both a distal surface and a proximal surface of the second gonioscopic optical element are substantially planar.

50. The gonioscopic assembly of claim 47, wherein the first and second gonioscopic optical elements are positioned such that light exiting the first gonioscopic optical element is directed toward the second gonioscopic optical element.

51. The gonioscopic assembly of claim 50, wherein at least a portion of the light reflected by a trabecular meshwork of an eye is transmitted through the second gonioscopic optical element and forms an upright virtual image of the trabecular meshwork viewable by a microscope without relying on reflection.

52. The gonioscopic assembly of claim 47, wherein the housing is removably attached to the handle or to the first gonioscopic optical element.

* * * * *